United States Patent
Yoshimoto

(10) Patent No.: US 11,214,591 B2
(45) Date of Patent: Jan. 4, 2022

(54) ENZYME COMPOSITIONS, STEROID DERIVATIVES, ENZYME INHIBITORS, AND METHODS OF MAKING SAME FOR PHARMACEUTICAL APPLICATIONS

(71) Applicant: BOARD OF REGENTS, THE UNIVERSITY OF TEXAS SYSTEM, Austin, TX (US)

(72) Inventor: Francis Yoshimoto, San Antonio, TX (US)

(73) Assignee: Board of Regents, the University of Texas System, Austin, TX (US)

(*) Notice: Subject to any disclaimer, the term of this patent is extended or adjusted under 35 U.S.C. 154(b) by 0 days.

(21) Appl. No.: 16/576,406

(22) Filed: Sep. 19, 2019

(65) Prior Publication Data

US 2020/0172567 A1 Jun. 4, 2020

Related U.S. Application Data

(60) Provisional application No. 62/733,179, filed on Sep. 19, 2018.

(51) Int. Cl.
| | |
|---|---|
| *C07D 221/18* | (2006.01) |
| *A61K 31/473* | (2006.01) |
| *C07J 73/00* | (2006.01) |
| *C07J 9/00* | (2006.01) |

(52) U.S. Cl.
CPC .......... *C07J 73/005* (2013.01); *C07J 9/00* (2013.01)

(58) Field of Classification Search
CPC ....... C07D 221/18; A61K 31/473; A61P 3/04; A61P 9/00
USPC .............................. 546/61; 552/553; 514/284
See application file for complete search history.

(56) References Cited

PUBLICATIONS

Malika, I-O. et al.: Synthesis of various secosteroidal macrocycles by ring-closing. Steroids, vol. 78, pp. 651-661, 2013.*
Malika, I-O. et al.: Synthesis of 12-oxa, 12-aza and 12-thia cholanetriols. Steroids, vol. 76, pp. 324-330, 2011.*

* cited by examiner

*Primary Examiner* — Charanjit Aulakh
(74) *Attorney, Agent, or Firm* — David G. Rosenbaum; Rosenbaum IP

(57) ABSTRACT

The present disclosure provides for a synthetic strategy to incorporate a C12α-hydroxy group from the methylene (—CH2-) in a steroid backbone, combining synthetic chemistry and enzymology techniques to develop a selective inhibitor for cytochrome P450 8B1, and developing a selective P450 8B1 inhibitor, which can be used as a tool to study P450 8B1 and treat health issues.

10 Claims, 96 Drawing Sheets

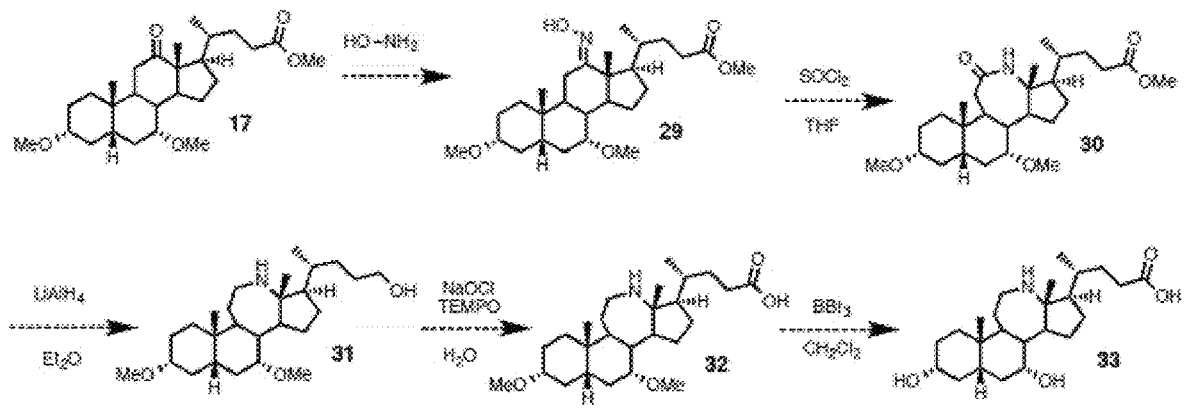
FIG. 17
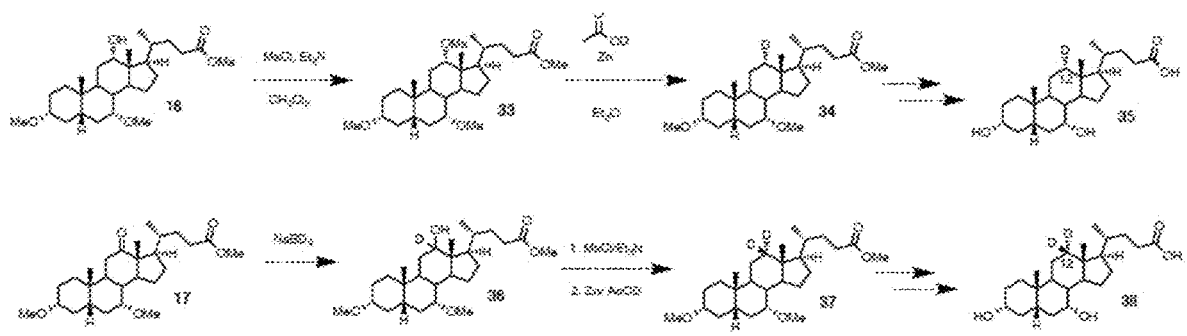
FIG. 18
FIG. 19

ENZYME COMPOSITIONS, STEROID DERIVATIVES, ENZYME INHIBITORS, AND METHODS OF MAKING SAME FOR PHARMACEUTICAL APPLICATIONS

CROSS-REFERENCE TO RELATED APPLICATIONS

This application claims priority to U.S. Provisional Application No. 62/733,179 filed Sep. 19, 2018, which is hereby incorporated by reference in its entirety.

BACKGROUND OF THE INVENTION

Cytochromes P450 8B1 and 8A1, two enzymes, are not well understood by the industry. There is little information about P450 8B1 biochemistry available to date, and there is no known reported expression and purification of this enzyme.

Cholic acid is a molecule that falls in the class of bile acids, which are an important class of compounds with various functions. Cholic acid has been shown to increase cholesterol absorption in humans through the formation of micelles. It has also been suggested from a mice feeding study that the bile acid composition of the micelles affect the micellar solubilization of cholesterol cholic acid had the highest cholesterol absorption (79%) over chenodeoxycholic acid (60%) and ursodeoxycholic acid (37%). Additionally, there are bile acid receptors, farnesoid X receptor (FXR) and G-protein coupled receptor (GPCR) TGR5, which are targets for metabolic diseases. TGR5 agonists are ligands that have the same action as cholic acid and chenodeoxycholic acid. These small molecules have been shown to induce intestinal glucagonlike peptide-1 (GLP-1) release by activating TGR5, which resulted in increased glucose tolerance in obese mice.

Humans have 57 cytochrome P450 enzymes, which belong to the superfamily of enzymes that contain an iron-containing heme prosthetic group. These enzymes are involved in the metabolism of exogenous drugs and also endogenous substrates such as sterols, steroids, lipids, vitamins, and fatty acids to produce important hormones that are essential for normal physiology. The classical P450 catalyzed reaction is the C—H hydroxylation reaction, which occurs through a nine step catalytic cycle involving activation of molecular oxygen followed by electron transfer from NADPH through cytochrome P450 reductase for microsomal P450 enzymes (and adrenodoxin for mitochondrial P450 enzymes).

Selective P450 inhibitors are used in the clinic (e.g. abiraterone is a P450 17A1 inhibitor used to treat androgen-dependent prostate cancer, exemestane is a P450 19A1 inhibitor used to treat estrogen-dependent breast cancer) because of the ability of certain P450 enzymes to produce specific hormones.

Many research efforts have been focused on the characterization of these important enzymes through the use of heterologous protein expression and purification techniques followed by in vitro experiments. However, there is no reported expression and purification of human P450 8B1 in the literature and the closest attempt towards this goal is with the expression of rabbitP450 8B1 in COS cells but without any purification; similarly, rat liver microsomes have been prepared to measure 12α-hydroxylation of cholesterol. In all reported cases, purified P450 8B1 was never used. Moreover, there is no known selective inhibitor for this enzyme.

Deleting the Cyp8b1 gene in mice resulted in a compensatory overexpression of Cyp7a1, another P450 enzyme whose activity results in the production of chenodeoxycholic acid, which is essentially 12-desoxycholic acid. However, recent studies showed that P450 8B1 knockout mice have an upregulation of brown fat genes and an improved lipid profile leading to a more favorable body weight, suggesting that P450 8B1 is a potential therapeutic target to treat obesity and cardiovascular disease.

Despite their potential physiological importance, 12α-hydroxylated steroids and sterols are underexplored. Various oxysterols are known to activate protein receptors such as the liver X receptor (LXR) and farnesoid X receptor (FXR). Access to 12α-hydroxylated steroid and sterol structures would be necessary to explore their biochemical properties and facilitate the identification of new bioactive 12α-hydroxy steroid products arising from P450 8B1 activity. However, there is no known report of the introduction of a 12α-hydroxy group from a C12-desoxy steroid. Therefore, there is a need for a synthetic strategy to incorporate a C12α-hydroxy group from the methylene (—CH2-) in the steroid backbone.

There is a need to combine synthetic chemistry and enzymology techniques to develop a selective inhibitor for cytochrome P450 8B1, and measure the biological effects of inhibition, which will uncover new processes implicated in cardiovascular disease. Particularly, there is a need to develop a selective P450 8B1 inhibitor, which can be used as a tool to study P450 8B1 and treat obesity and cardiovascular disease. P450 8B1 is an important enzyme for the production of bile acids and the 12-hydroxylated products of P450 8B1 are substrates for bacterial enzymes, which produce secondary bile acids. P450 8A1, prostacyclin synthase, is the protein with closest sequence identity to P450 8B1. Prostacyclin synthase converts prostaglandin H2 to prostacyclin, which inhibits platelet activation and functions as a vasodilator.

SUMMARY OF THE INVENTION

Cytochrome P450 8B1 (P450 8B1) is an oxysterol 12α-hydroxylase enzyme whose activity ultimately yields the 12α-hydroxy primary bile acid, cholic acid. Many metabolic disorders arise from defects in the enzymes in this pathway. The biosynthesis of cholic acid from cholesterol begins with the oxidation of the C7-position by P450 7A1 to yield 7α-hydroxycholesterol. 7α-Hydroxycholesterol is oxidized at the 3-position and the 5,6-double bond is isomerized to the 4,5-position by 3β-hydroxysteroid dehydrogenase to yield 7α-hydroxycholest-4-en-3-one, the substrate for P450 8B1. P450 8B1 introduces the 12α-hydroxy group to yield 7α-,12α-dihydroxycholest-4-en-3-one, which in turn is reduced to 5β-7α-,12α-dihydroxycholestan-3-one by 3-oxo-5β-steroid 4-dehydrogenase. The 3-keto moiety is stereoselectively reduced by 3α-hydroxy steroid dehydrogenase to afford 3α-,7α-,12α-trihydroxy-5β-cholestane, which is the substrate for P450 27A1. P450 27A1 oxidizes the C27-methyl to yield 3α-,7α-,12α-trihydroxy-5β-cholestanoic acid. Solute carrier family 27 (member 5) forms the thioester bond to furnish (25R)-3α-,7α-,12α-trihydroxy-5β-cholestanoyl CoA, and the C25-stereocenter is epimerized by α-methylacylCoA racemase to yield (25S)-3α-,7α-,12α-trihydroxy-5β-cholestanoyl CoA. The resulting C24-position is hydroxylated by 3α-,7α-,12α-trihydroxy-5β-cholestanoyl CoA 24-hydroxylase to give (25S)-3α-,7α-,12α-,24-tetrahydroxy-5β-cholestanoyl CoA, which is regioselectively oxidized at the C24 position by 3-hydroxyacyl-CoA dehydrogenase, giving (25S)-3α-,7α-,12α-trihydroxy-5β-24-oxocholestanoyl CoA. Sterol carrier protein 2 cleaves the C24-C25 bond to yield 3α-,7α-,12α-trihydroxy-5β-cholanoyl CoA, which is hydrolyzed by Acyl CoA hydrolase to yield cholic acid.

Bile acids form micelles, which regulate the intestinal absorption of lipids. In particular, cholic acid supplementation has been shown to enhance the absorption of cholesterol. Furthermore, mice lacking the CYP8B1 gene encoding for P450 8B1, showed a resistance to weight gain when fed a high-cholesterol diet. Therefore, 12α-hydroxy steroids can possibly serve as biomarkers for certain cardiovascular disease states.

From the use of P450 8B1 knockout mice (mice lacking the Cyp8b1 gene), it has been shown that the absence of this enzyme leads to a 50% decrease in cholesterol absorption, increased excretion of cholesterol, and significant upregulation of brown-fat genes. These results suggest that the inhibition of P450 8B1 is a potential therapeutic strategy for treating obesity and cardiovascular disease. Cytochrome P450 8B1 (P450 8B1, also known as 12α-hydroxylase) is the microsomal cytochrome P450 enzyme responsible for the 12α-hydroxylation of oxysterols, which is a key step in the biosynthesis of cholic acid, a bile acid with intriguing biological activity. There is little information about P450 8B1 biochemistry available to date, and there is no known reported expression and purification of this enzyme.

Recent studies showed that P450 8B1 knockout mice have an upregulation of brown fat genes and an improved lipid profile leading to a more favorable body weight.

One embodiment of the present disclosure comprises using P450 8B1 as a therapeutic target to treat obesity and cardiovascular disease.

Another embodiment of the present disclosure comprises using P450 8B1 to inhibit P450 11B2 and P450 11B1, which produce corticosteroids and mineralocorticoids, related to the stress response and hypertension.

Another embodiment of the present disclosure comprises using an inhibitor synthesis and incorporate new substituents on the C11-position.

Another embodiment of the present disclosure comprises synthesizing analogs, such as elongation of the side chain or adding substituents on the sterol ring of the synthesized analog.

Synthesis of Chemical Probes For P450 8B1

Another embodiment of the present disclosure comprises synthesis of rationally designed inhibitors and substrate analogs for P450 8B1 to use as tools to study the protein biochemistry of this enzyme. Compounds mimicking the structures of the natural substrates and also containing a nitrogen heteroatom can be synthesized and are tested as inhibitors for this enzyme. This strategy has been accomplished in inhibiting other classes of P450 enzymes (e.g. abiraterone, a P450 17A1 inhibitor). Additionally, deuterated oxysterol substrates can be synthesized as a tool to measure the kinetic isotope effect of the C—H abstraction process. 12-Desoxysterol compounds can be synthesized to test for a possible "backdoor" pathway to cholic acid.

Another embodiment of the present disclosure comprises using the inhibitor as a drug to treat obesity.

Robust Expression and Purification

Another embodiment of the present disclosure comprises expressing and purifying P450 8B1 heterologously to characterize its enzymatic activity and test for viable inhibitors. With the heterologous expression and purification, we can employ steady state and rapid kinetic methods to measure substrate and product binding and release rates. The purified protein can also be used to test for selective inhibitors for this enzyme using a medium throughput assay. We can also perform X-ray crystallography studies to obtain a 3-dimensional structure of the enzyme. Additionally, we can test other possible substrates for this enzyme to uncover any "backdoor" pathway in the biosynthesis of cholic acid.

Another embodiment of the present disclosure comprises studying the structural relationship between P450s 8B1 and 8A1 to understand the substrate recognition and electron transfer processes of P450 enzymes.

Another embodiment of the present disclosure tests the hypothesis that inhibition of P450 8B1 can result in a healthier cardiometabolic profile by measuring the biological effects of inhibiting P450 8B1 in tissues. Hepatocytes can be used and P450 8B1 enzymatic activity can be inhibited by using the novel selective inhibitors and siRNA to knockdown the Cyp8b1 gene.

Another embodiment of the present disclosure comprises performing proteomics, transcriptomics, and metabolomics assays to measure changes in protein, gene, and metabolite levels. These experiments can confirm in vivo results from P450 8B1 knockout mice and reveal other biochemical pathways linked to cholic acid biosynthesis.

Another embodiment of the present disclosure comprises developing: (a) a robust expression and purification system for this enzyme, (b) enzymatic characterization of the individual rates of the catalytic cycle, (c) inhibition studies of this enzyme, (d) an alternative biosynthetic route to cholic acid (i.e. the discovery of a "backdoor" pathway to cholic acid), and (e) identification of genes regulated by P450 8B1 inhibition. A selective P450 8B1 inhibitor can be used as a tool to study the effects of inhibiting cholic acid biosynthesis, and used as drug to treat obesity and cardiovascular diseases.

Another embodiment of the present disclosure comprises a synthetic strategy to introduce a 12α-hydroxy group from the C12-methylene in steroid derivatives was established. This route involves the coppermediated Schönecker oxidation to introduce the 12β-hydroxy group. The resulting 12β-hydroxy group can be oxidized to the C12-keto moiety, which was stereoselectively reduced to the 12α-hydroxy group using lithium tri-sec-butylborohydride (L-Selectride). These 12α-hydroxy steroids and sterols can be used as chemical tools to explore the biochemistry of cytochrome P450 8B1, the oxysterol 12α-hydroxylase enzyme implicated in cardiovascular health.

BRIEF DESCRIPTION OF THE DRAWINGS

FIG. 17 illustrates the synthesis of an azepane analog of cholic acid;

FIG. 18 illustrates the synthesis of deuterated chenodeoxycholic acid compounds as substrates for P450 8B1;

FIG. 19 illustrates the multiple sequence alignment of P450s 8A1 and 8B1;

DETAILED DESCRIPTION OF THE PREFERRED EMBODIMENTS

Figure 1:
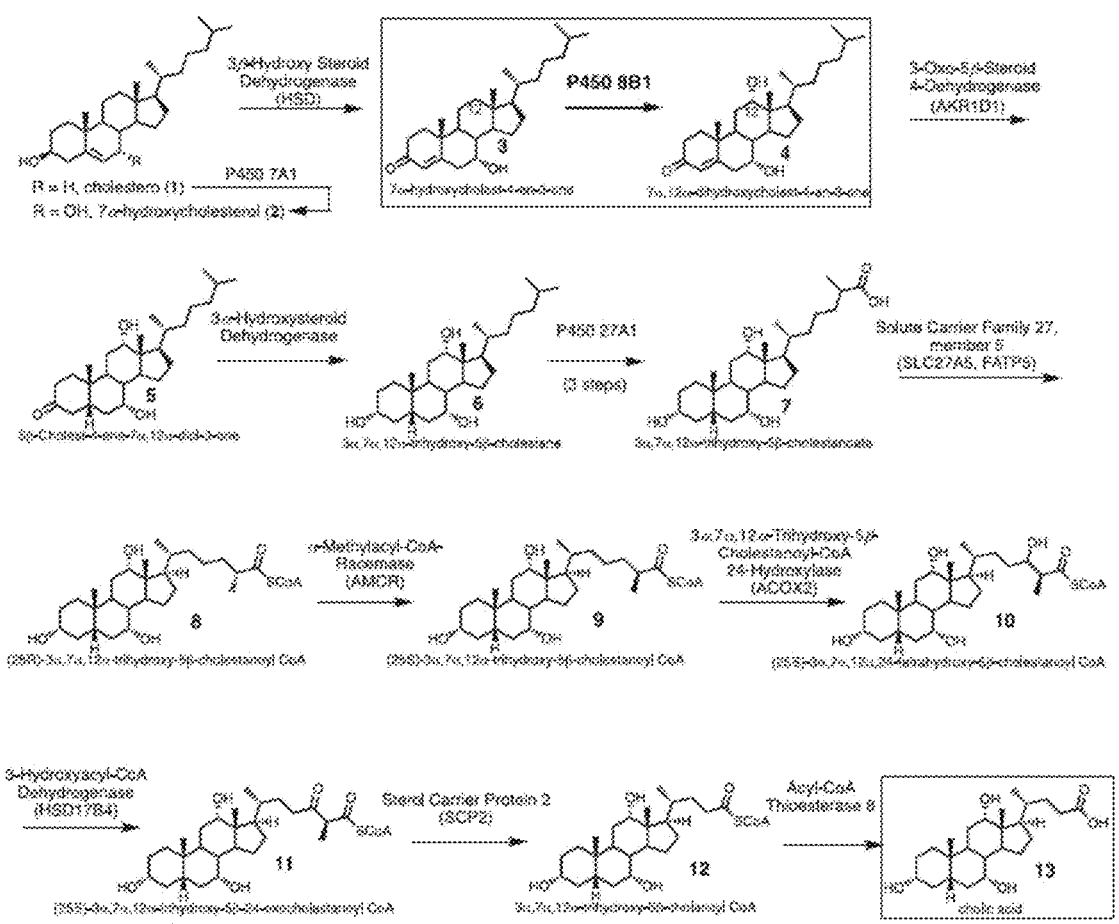
FIG. 1 illustrates the twelve step biosynthesis of Cholic acid from cholesterol.

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

Accordingly, the detailed discussion herein of one or more embodiments is not intended, nor is to be construed, to limit the metes and bounds of the patent protection afforded the present invention, in which the scope of patent protection is intended to be defined by the claims and equivalents thereof. Therefore, embodiments not specifically addressed herein, such as adaptations, variations, modifications, and equivalent arrangements, should be and are considered to be implicitly disclosed by the illustrative embodiments and claims described herein and therefore fall within the scope of the present invention.

Further, it should be understood that, although steps of various claimed methods may be shown and described as being in a sequence or temporal order, the steps of any such method are not limited to being carried out in any particular sequence or order, absent an indication otherwise. That is, the claimed method steps are considered capable of being carried out in any sequential combination or permutation order while still falling within the scope of the present invention.

Additionally, it is important to note that each term used herein refers to that which a person skilled in the relevant art would understand such term to mean based on the contextual use of such term herein. To the extent that the meaning of a term used herein, as understood by the person skilled in the relevant art based on the contextual use of such term, differs in any way from any particular dictionary definition of such term, it is intended that the meaning of the term as understood by the person skilled in the relevant art should prevail.

Furthermore, a person skilled in the art of reading claimed inventions should understand that "a" and "an" each generally denotes "at least one," but does not exclude a plurality unless the contextual use dictates otherwise. And that the term "or" denotes "at least one of the items," but does not exclude a plurality of items of the list.

Selective P450 inhibitors are used to treat cancer patients in the clinic. These inhibitors usually possess a carbon skeleton resembling the natural substrates (e.g. exemestane, a P450 19A1 inhibitor, resembles androstenedione, the substrate of P450 19A1) and most inhibitors have a nitrogen heteroatom, which coordinates to the iron active site of P450 enzymes (e.g. abiraterone, a P450 17A1 inhibitor, possesses the steroid-skeleton of pregnenolone, the substrate of P450 17A1, but also contains a pyridine moiety that coordinates to the iron center in P450 17A1).

In one embodiment of the present disclosure, a P450 8B1 inhibitor is designed to synthesize a compound with the carbon skeleton of its substrate and incorporating a nitrogen heteroatom where chemistry occurs (i.e. the 12-position of the steroid).

There is a retinoic acid orphan receptor α (RORα) response element located on the Cyp8b1 gene promoter of mice, which suggests that another mode of P450 8B1 inhibition can be through the use of RORα antagonists. However, there is only a 21% homology between the Cyp8b1 promoter regions in humans and mice indicating possible differences in transcriptional regulation between the two species. Interestingly, RORα does not seem to be related to Cyp7a1 gene expression in rats. In addition, insulin suppresses Cyp8b1 expression in rat hepatocytes.

Measurement of Different Gene Expression Targets Upon P450 8B1

In another embodiment of the present disclosure, exploration of human hepatocytes can be performed in culture because inhibition P450 8B1 is expressed in hepatocyte and the gene and protein expression effects upon P450 8B1 inhibition can be analyzed and captured.

In one embodiment of the present disclosure, the enzyme can be inhibited using a small molecule inhibitor selective for P450 8B1 where the small molecule inhibitor is designed to inhibit P450 8B1 in human hepatocytes.

In another embodiment of the present disclosure, P450 8B1 siRNA oligos can be used to knock down Cyp8b1 gene expression.

In another embodiment of the present disclosure, P450 8B1 CRISPR/Cas9 knockout plasmids can be used to shut down P450 8B1 expression. After P450 8B1 inhibition, mRNA is extracted and a transcriptome analysis is performed to measure gene expression changes. Similarly, we can extract proteins and metabolites and measure changes in protein and metabolite levels using mass spectrometry analyses.

Support for the Existence of 12α-Hydroxylated Steroids with 19 Carbons and 21 Carbons Turning to FIG. 1, Cholic acid (13) biosynthesis from cholesterol (1) involves twelve steps P450 8B1 and the oxysterol 12α-hydroxylase enzyme is the third step. The only known substrate of P450 8B1 is 7α-hydroxycholest-4-en-3-one (3), a 27-carbon containing sterol, which is converted to 7α-,12α-dihydroxycholest-4-en-3-one (4), the biosynthetic precursor of cholic acid. However, in the established biosynthesis of cholic acid, 7α-,12α-dihydroxycholest-4-en-3-one is ten steps upstream to cholic acid (13), illustrating alternative biological roles of 12α-hydroxylated sterols and steroids. An analogous situation is in the biosynthesis of glucocorticoids (21-carbon) and androgens (19-carbon) with P450 17A1 activity. P450 17A1 hydroxylates the C17-position of pregnenolone, the first 21-carbon steroid found in steroid biosynthesis, to yield 17α-hydroxypregnenolone.

The biosynthetic pathway bifurcates to yield glucocorticoids (e.g. cortisol) or androgens (e.g. testosterone), making 17α-hydroxypregnenolone, a precursor to two different classes of steroid hormones. P450 8B1 activity is found early in the biosynthesis of bile acids from cholesterol, the 12α-hydroxysterols can be precursors to bile acids and 12α-hydroxylated sterol or steroid hormones.

The isolation of other steroids with a 12α-hydroxy group has been reported. For instance, 12α-hydroxypregnenolone derivatives, named menarandrosides, have been recently isolated from plants (*Cynanchum marnierianum*). These novel 12α-hydroxylated steroids were identified from a bio-guided fractionation assay that detected the stimulation of glucagonlike peptide 1 (GLP-1) secretion, suggesting anti-diabetic activity. Other 12α-hydroxylated sterol plant natural products have been previously isolated in plants.

P450 8B1 is shown to hydroxylate the 12α-position of 7α-hydroxycholest-4-en-3-one (3) to 7α,12α,-dihydroxycholest-4-en-3-one (4). Alternative routes to cholic acid can be found by testing the ability of P450 8B1 to hydroxylate any 12-desoxy intermediates found in the pathway such as the structure of 7 (3α,7α,12α-dihydroxy-5β-cholestanoate) lacking the 12-hydroxy group (i.e. 3α,7α,-dihydroxy-5β-cholestanoate).

Synthesis of Chemical Tools to Probe P450 8B1 Mechanism

P450 8B1 inhibition may be a therapeutic strategy to treat obesity and cardiovascular diseases. The main approach to selectively inhibit P450 8B1 can be to synthesize a compound containing the carbon backbone of the P450 8B1 substrate and introducing a nitrogen heteroatom where chemistry occurs. The P450 8B1 can recognize the substrate backbone of the inhibitor, and the nitrogen atom of the inhibitor will coordinate to iron in the active site of P450 8B1 and shut down enzymatic activity. A similar strategy has been used in abiraterone, a P450 17A1 inhibitor. Competitive inhibitors for rabbit hepatic microsomal steroid 12α-hydroxylase (P450 8B1) have been reported, and these compounds did not inhibit at very effective concentrations (Ki 35-98 μM) and more importantly, these compounds do not possess a nitrogen heteroatom, which results in a Lewis acid-Lewis base interaction between the heme active site of the enzyme and the nitrogen lone pair of the inhibitor (FIG. 2).

Proposed Biosynthesis of Other 12α-Hydroxy Steroids

Figure 2:
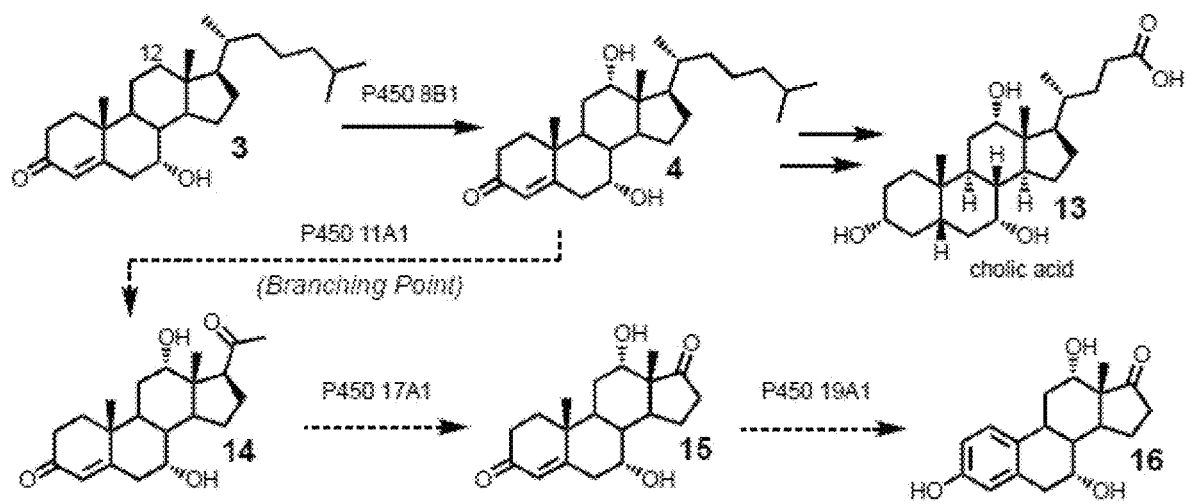
FIG. 2 illustrates biosynthesis of 12α-hydroxylated steroids through a ranching point in cholic acid biosynthesis.

Turning to FIG. 2, the biosynthesis of 12α-hydroxylated steroids through a ranching point in cholic acid biosynthesis (4 to 14) can be seen. It was known through study that 12α-hydroxylation activity of purified P450 8B1 was with the substrate, 7α-hydroxycholest-4-en-3-one, and afforded 7α-,12α-dihydroxycholest-4-en-3-one (see (3) and (4)). Okuda and co-workers first reported this reaction catalyzed by purified cytochrome P450 8B1 from rabbit liver.

Figure 14:
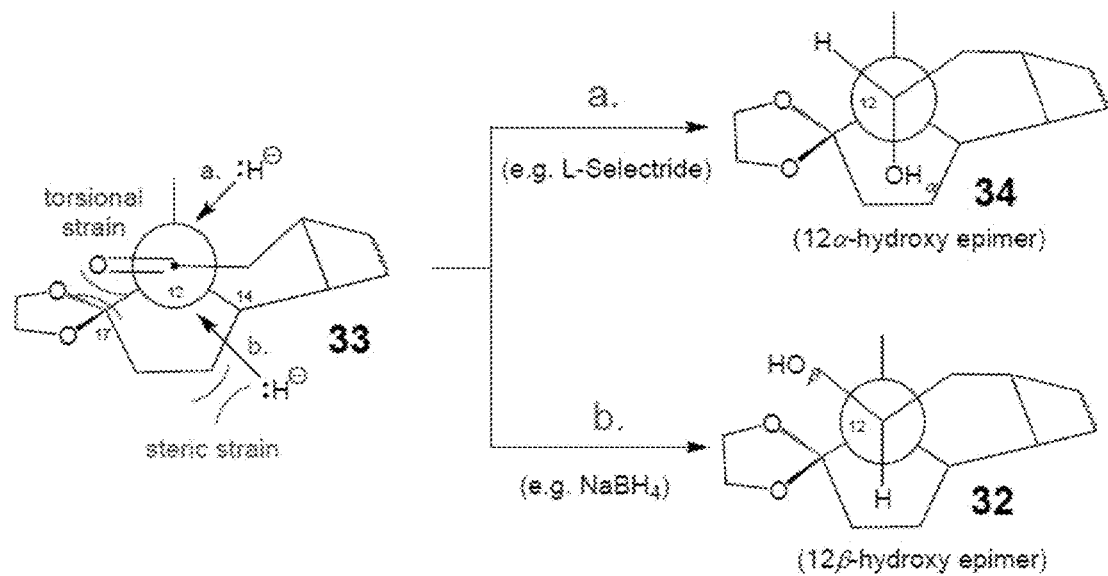
FIG. 14 illustrates the Newman projection analysis at the C12-C13 dihedral angle of intermediate 33, in order to determine the stereoselectivity in the hydride reduction at the C12-ketone.
Figure 15:
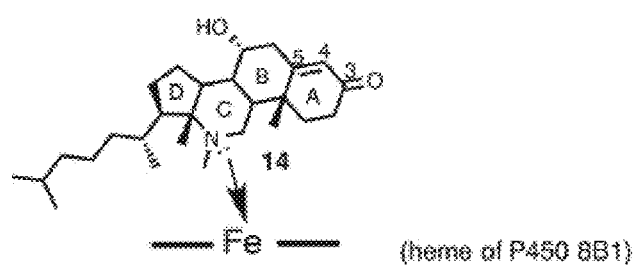
FIG. 15 illustrates one embodiment of a P450 8B1 inhibitor.

In one embodiment of the present disclosure, the 12α-hydroxylation of 7α-hydroxycholest-4-en-3-one by P450 8B1 is the third step (FIGS. 1, 3 to 4) in the 12-step biosynthesis of cholic acid from cholesterol. This product can be cleaved by P450 11A1 to yield 7α-,12α-dihydroxyprogesterone (FIGS. 2, 4 to 14), a branching point from cholic acid biosynthesis to yield other 12α-hydroxylated steroids. 7α-,12α-dihydroxyprogesterone can be processed by P450 17A1 to yield 7α-,12α-dihydroxydehydroandrostenedione (FIGS. 2, 14 to 15). The resulting 19-carbon androgen, 7α-,12α-dihydroxyandrostenedione, can be oxidized by P450 19A1, resulting in the formation of 7α-,12α-dihydroxyestrone (FIGS. 2, 14 to 16).

Potential Direct 12α-Hydroxylation of 19-Carbon and 21-Carbon Steroid Substrates by P450 8B1

In another embodiment of the present invention, the formation of 12α-hydroxylated 21-carbonpregnanes and 19-carbon-androgens can involve the direct oxidation by P450 8B1 of various steroid substrates to yield the corresponding 12α-hydroxylated steroids. The ability of a steroidogenic cytochrome P450 enzyme to recognize different steroid substrates with varying C17-alkyl substituents has been observed with other P450s. Recent studies of prostate cancer tissue suggest the physiological importance of 11-oxygenated 19-carbon androgens, which are derived from the 11β-hydroxylation of androgens from P450 11B, an enzyme classically known to only hydroxylate 21-carbon steroids. The catalytic promiscuity of P450 11B1 that results in the C11-hydroxylation of 19-carbon androgens suggests the possibility of a similar activity with P450 8B1 (i.e. C12α-hydroxylation of 19-carbon androgens by P450 8B1).

Figure 3:
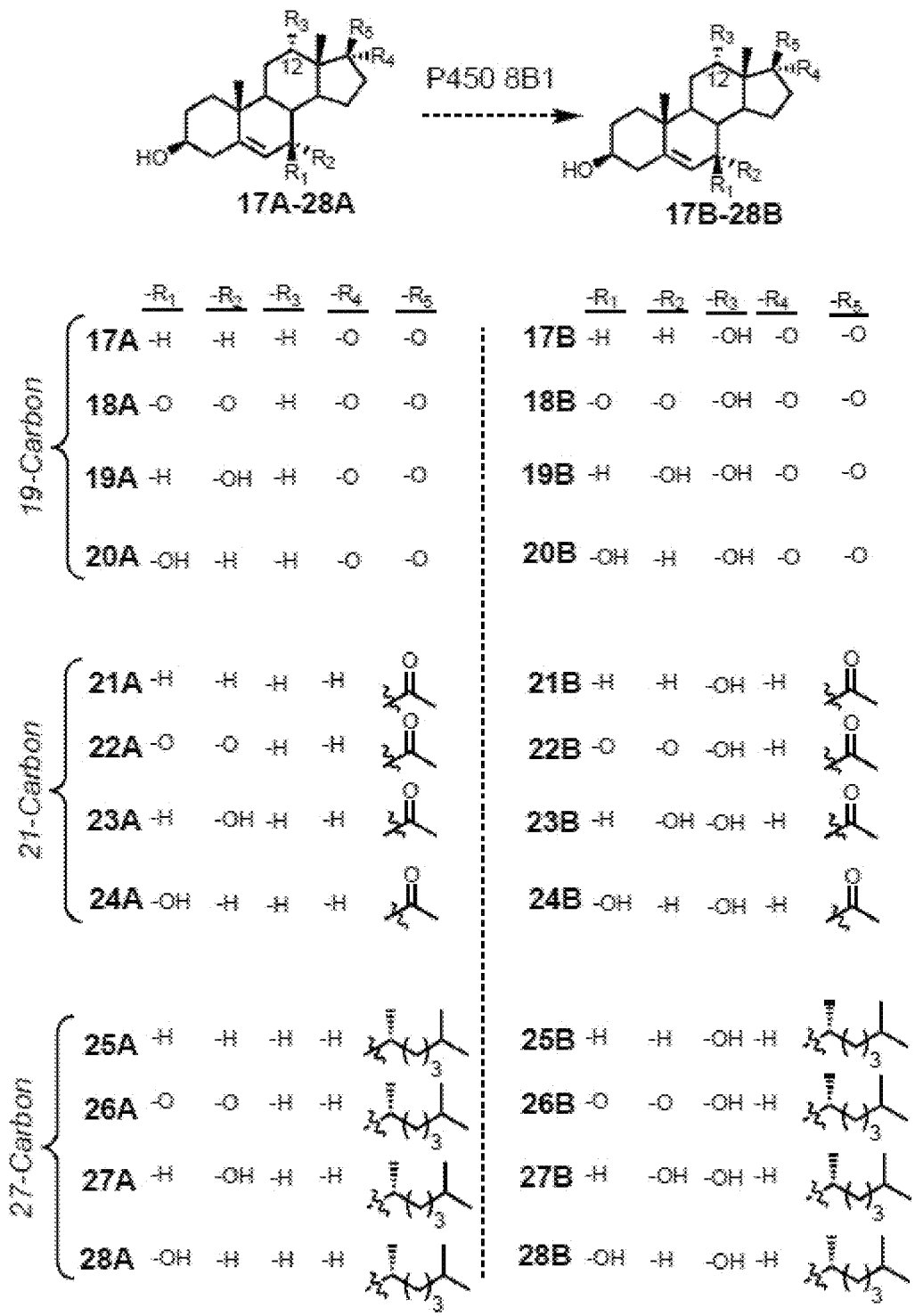
FIG. 3 illustrated the P450 8B1-catalyzed 12α-hydroxylation of various steroids and sterols to yield the corresponding 12α-hydroxylated steroids and sterols.

Turning to FIG. 3, although it is an endogenous steroid hormone, 7-keto dehydroepiandrosterone (7-keto DHEA) and its acetate form has been used to treat certain health conditions. For example, 7-keto dehydroepiandrosterone-3-acetate (7-keto DHEA-3OAc) has been shown to reduce post-traumatic stress disorder (PTSD) symptoms and also to reverse the resting metabolic rate associated with dieting. 7-Keto DHEA has also decreased voluntary intake of ethanol in male rats. The various 7-oxygenated DHEA forms (7β-hydroxy-, 7α-hydroxy, and 7-keto DHEA) are interconverted by liver 11β-hydroxysteroid dehydrogenase 1. When P450 8B1 has a flexible active site and is able to oxidize 19- and 21-carbon steroids, it can oxidize 7-oxygenated DHEA variants into 12α-hydroxylated products (17A-20A to 17B-20B). Synthesis of 12α-hydroxy dehydroepiandrosterone (FIG. 3, 17B) and its derivatives with varying oxidation states at the C7-position (i.e. 7-keto-, 7α-hydroxy-, and 7β-hydroxy) can also be seen in FIG. 3 (18B, 19B, and 20B).

19-carbon- and 21-carbon-12α-hydroxy steroids can be produced from downstream biosynthetic processes that modify 7α-,12α-dihydroxycholest-4-en-3-one, the enzymatic product of P450 8B1 (FIG. 2, 4), or directly from P450 8B1 activity (FIG. 3).

Synthetic Strategy to 12α-Hydroxy Steroids

There is no known approach to synthesize 12α-hydroxylated steroids and sterols from steroid precursors possessing a C12-methylene (—CH2-) group. However, incorporation of a 12β-hydroxy group from a DHEA-imine derivative through a copper mediated oxygenation has been reported.

Figure 4:
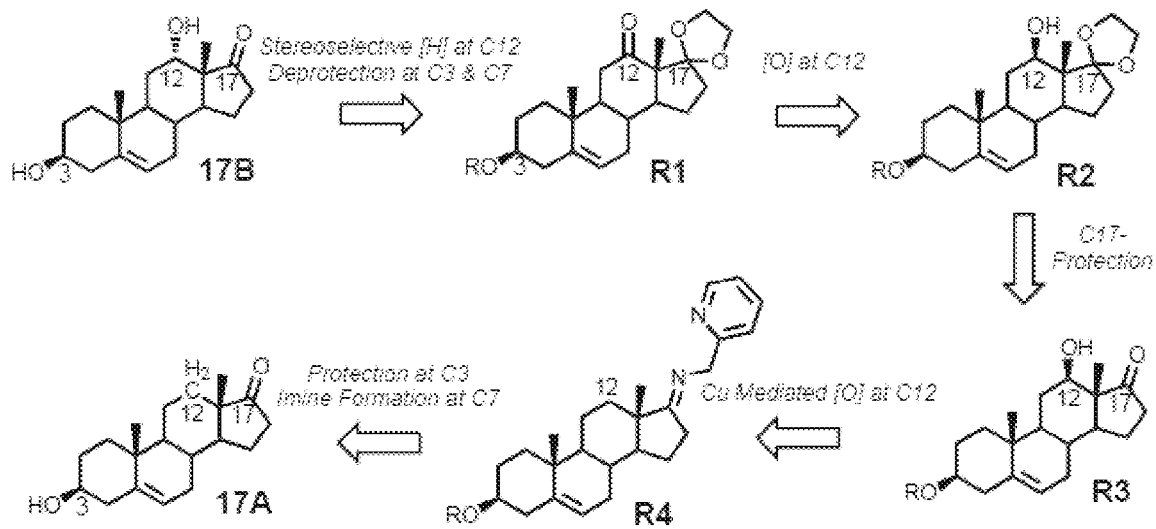
FIG. 4 illustrates the retrosynthetic analysis to introduce a 12α-hydroxy group in the steroid backbone from a C12-methylene (—CH2-) precursor.

FIG. 4 illustrates another embodiment of this disclosure, the oxidation of the C12β-hydroxy group to the C12-ketone (FIG. 4, R1), can be stereoselectively reduced to the 12α-hydroxy group. Retrosynthetic analysis introduces a 12α-hydroxy group in the steroid backbone from a C12-methylene (—CH2-) precursor (17B from 17A).

Synthesis of 12α-Hydroxy Dehydroepiandrosterone (17B)

Figure 5:
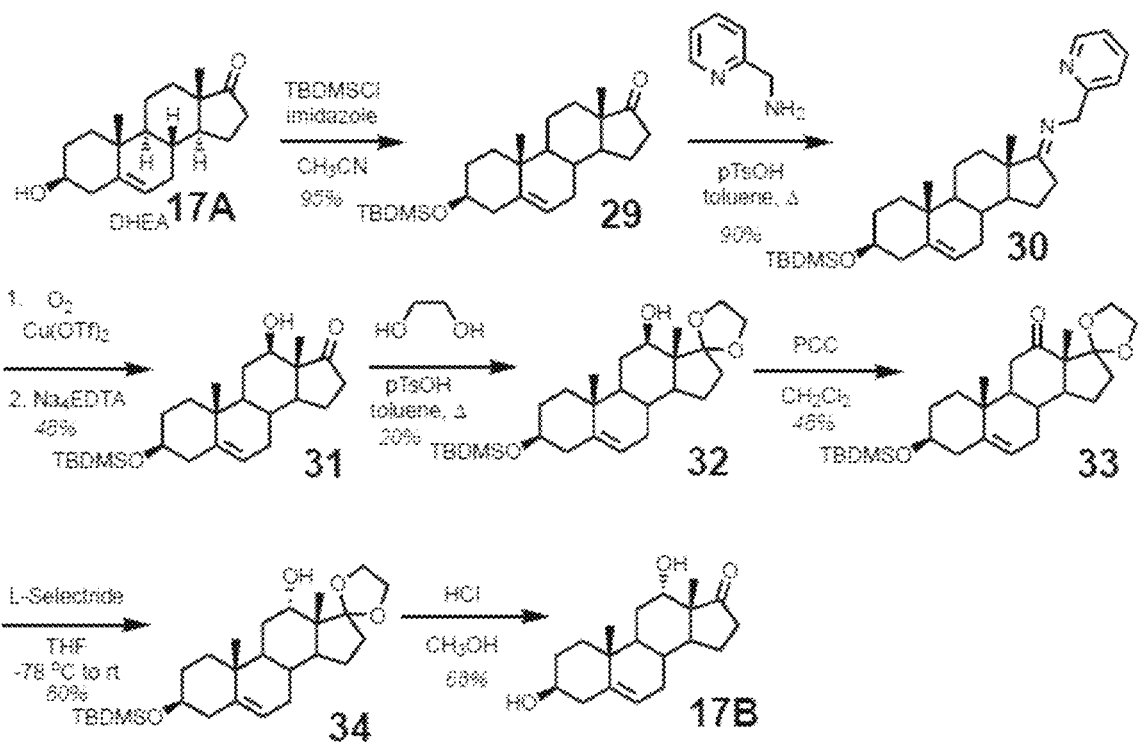
FIG. 5 illustrates the synthesis of 12α-hydroxy DHEA from DHEA.

FIG. 5 illustrates the synthesis of dehydroepiandrosterone (DHEA, 17A), protected as the DHEA-3-O-tertbutyldimethylsilyl ether 29, which can be converted to the pyridine-imine derivative at C17. The Schönecker protocol through a copper mediated oxidation resulted in the introduction of the 12β-hydroxy group to yield 12β-hydroxy DHEA-3-OT-BDMS ether 31.

The resulting C17-ketone can be protected as the ketal, allowing for the incorporation of a C12-ketone bearing intermediate 33 and subsequent stereoselective reduction at the C12-position to give the 12α-hydroxy 34. Deprotection of the TBDMS group and the C17-ketal with HCl in CH3OH yielded 12α-hydroxy DHEA (17B).

The synthesis of 12α-hydroxy-7-keto DHEA (18B) could be potentially accomplished from 12α-hydroxy DHEA through the oxidation of the C7-allylic position using a previously reported protocol using CrO3 and 3,5-dimethylpyrazole. Prior to the C7-allylic oxidation, the C3- and C12α-hydroxy groups would be protected as acetates.

Figure 6:
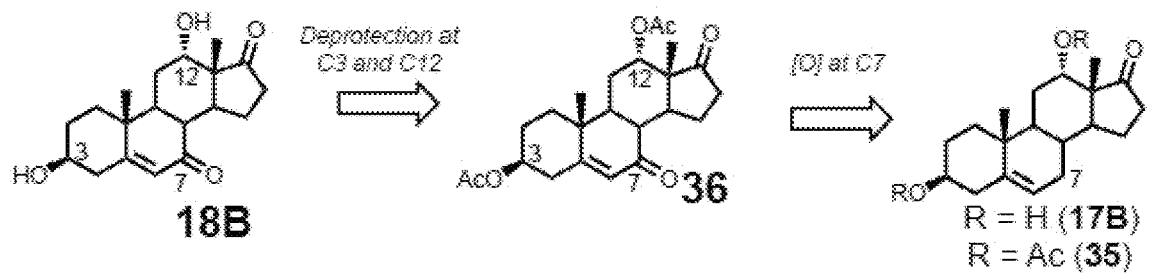
FIG. 6 illustrates the retrosynthetic analysis for the synthesis of 12α-hydroxy-7-keto DHEA.
Figure 7:
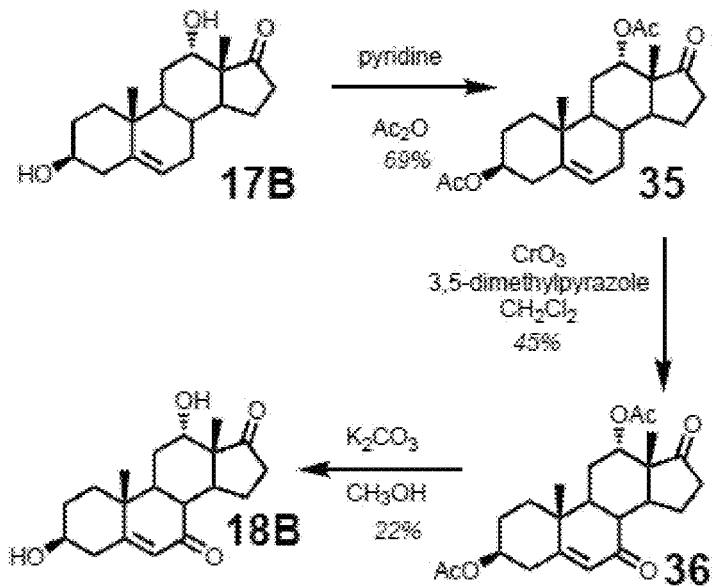
FIG. 7 illustrates the synthesis of 12α-hydroxy-7-keto dehydroepiandrosterone (18B) from 12α-hydroxy DHEA.

Turning to FIGS. 6 and 7, the retrosynthetic analysis for the synthesis of 12α-hydroxy-7-keto DHEA (18B) is illustrated in FIG. 6. FIG. 7 illustrates the synthesis of 12α-hydroxy-7-keto dehydroepiandrosterone commenced with 12α-hydroxy DHEA. The dihydroxy compound (17B) can be diacetylated using triethylamine and acetic anhydride as the solvent. When acetic anhydride is used in slight excess (up to 3 mol equivalents) with tetrahydrofuran as the solvent, the 12α-hydroxy group is not protected. The C7-position can be oxidized to the C7-keto group using CrO3 and 3,5-dimethylpyrazole in CH2Cl2 (FIG. 7). The resulting diacetate (36) is deprotected with K2CO3 in CH3OH to yield 12α-hydroxy-7-keto DHEA (18B). FIG. 7 also illustrates the synthesis of 7α-,12α-Dihydroxy-Dehydroepiandrosterone (19B).

Figure 8:
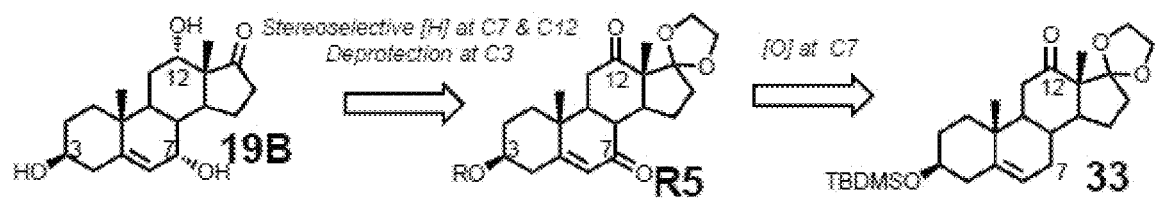
FIG. 8 illustrates retrosynthetic analysis for the synthesis of 7α-,12α-dihydroxydehydroepiandrosterone.

Turning to FIG. 8, another embodiment of the present disclosure is illustrated. In order to efficiently access 7α-,12α-dihydroxy DHEA (19B), a 7-,12-diketo steroid intermediate (R5) can be stereoselectively reduced by lithium tri-sec-butylborohydride (L-Selectride) to furnish the α-hydroxy stereochemistry at both the C7- and C12-positions. This stereoselective reduction of the ketones can be based on the observation that L-Selectride results in the delivery of the hydride onto the β-face of C7-keto steroid backbones and C12-keto backbones (vide supra, Scheme 1, 33 to 34). The synthesis of the 7α-,12α-dihydroxy DHEA (19B) commences with the oxidation of the C7-allylic position of 12-keto C17-ketal 33 with CrO3 to furnish diketone 37.

Figure 9:
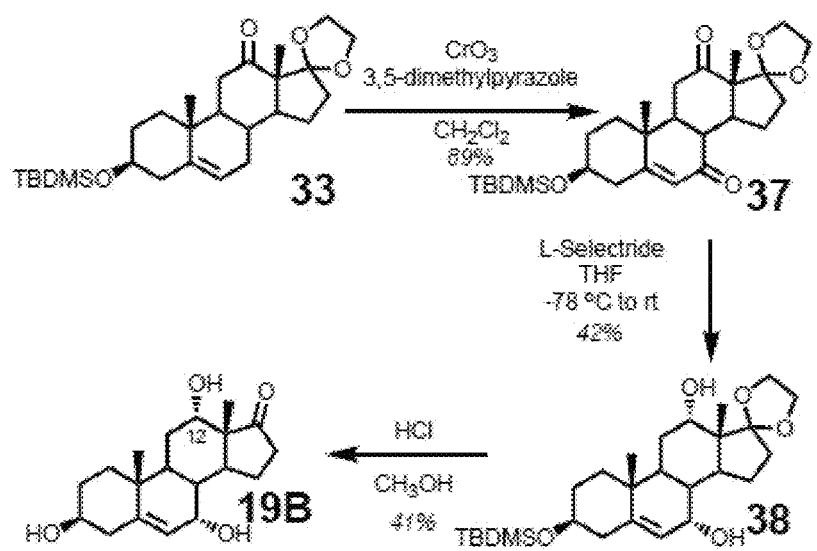
FIG. 9 illustrates the synthesis of 7α-,12α-dihydroxy DHEA.

Turning to FIG. 9, diketone 37 is being reduced with L-Selectride to afford the 7α-,12α-dihydroxy ketal 38. Treating ketal 38 with HCl in CH3OH results in the deprotection of both the C17-ketal and the C3-tertbutyldimethylsilyl ether to afford 7α-,12α-dihydroxy DHEA (19B).

Synthesis of 7β-,12α-Dihydroxy-Dehydroepiandrosterone

Figure 10:
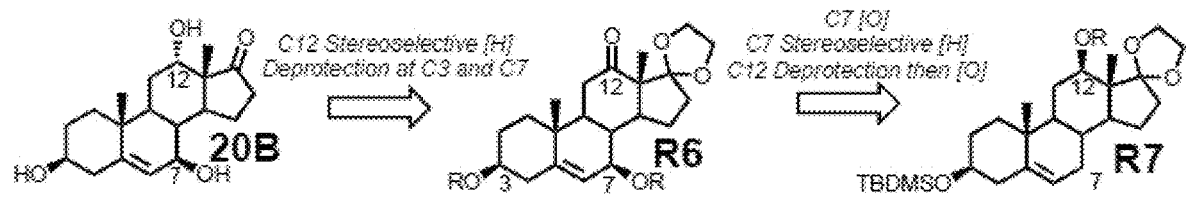
FIG. 10 illustrates the synthesis of retrosynthetic analysis of 7β-,12α-dihydroxy-dehydroepiandrosterone.

Turning to FIG. 10, another embodiment Retrosynthetic analysis of 7β-,12α-dihydroxy-dehydroepiandrosterone (20B). Among the four 12α-hydroxylated DHEA derivatives (17B-20B), 7β-,12α-dihydroxydehydroepiandrosterone (20B) comprises opposing stereochemistry of the hydroxy groups at the C7- and C12-positions (C73-hydroxy and C12α-hydroxy) and in order to achieve the C12α-hydroxy stereochemistry, L-Selectride can be employed as the hydride source. A different reducing agent is needed to introduce the β-hydroxy orientation at C7.

Figure 11:
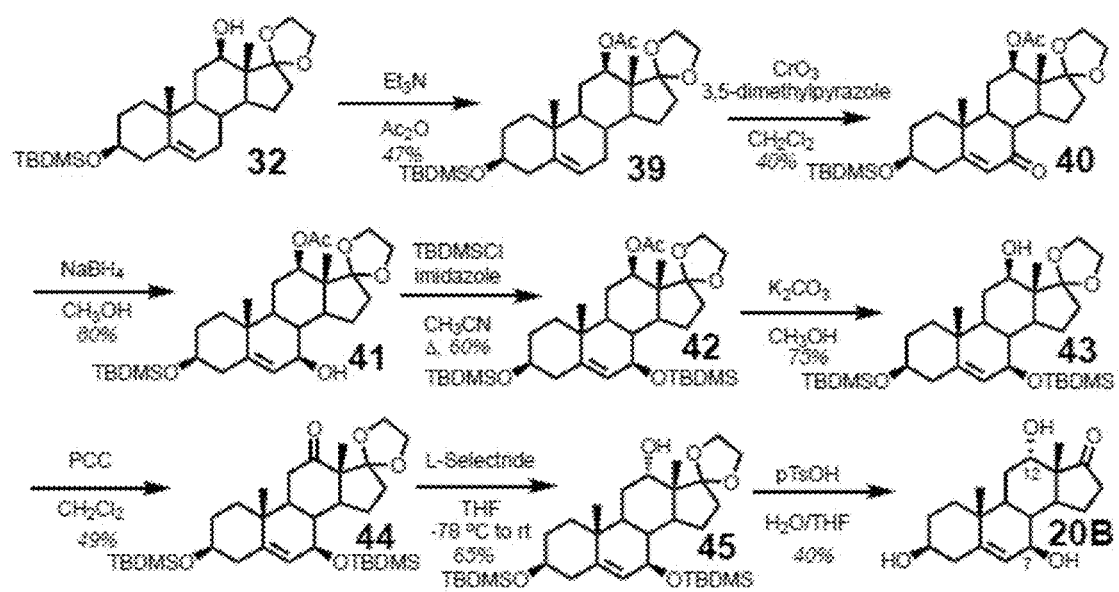
FIG. 11 illustrates the synthesis of 7β-,12α-dihydroxy DHEA.

FIG. 11 illustrates another embodiment of the present disclosure and comprises the 12β-hydroxy group of ketal 32 is protected as the acetate with triethylamine and acetic anhydride to yield 12β-acetate 39. The C7-allylic position can be oxidized with CrO3 and 3,5-dimethylpyrazole to furnish enone 40. The C7-ketone can be stereoselectively reduced with NaBH4 to yield a crude mixture of 7β-hydroxy and 7α-hydroxy epimers in a 4:1 ratio (determined by 1H NMR, Supporting Information). This mixture can be purified by silica gel column chromatography, which gives the 7β- to 7α-epimeric mixture, which is resolved over the subsequent steps towards the final product, 20B. The 7β-hydroxy group of alcohol 41 is protected as the tert-butyldimethylsilyl diether 42 by refluxing with TBDMSCl and imidazole in CH3CN. The acetate can be methanolyzed with K2CO3 in CH3OH to yield alcohol 43.

Alcohol 43 can be oxidized with pyridinium chlorochromate (PCC) to yield C12-ketone 44, which can be stereoselectively reduced with L-Selectride to give the 12α-hydroxy epimer 45. Deprotection of the two tert-butyldimethylsilyl groups and the C17-ketal with catalytic amounts of para-toluenesulfonic acid in water and THF to furnish 7β-,12α-dihydroxy DHEA 20B.

Figure 12:
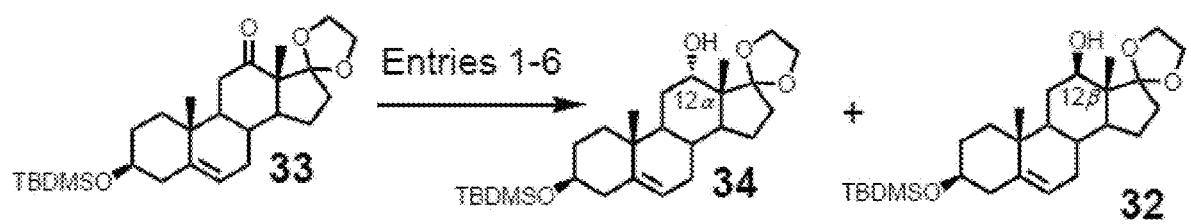
FIG. 12 illustrates the reduction of Ketone 33 with different reducing agents.

FIG. 12 illustrates another embodiment of the present disclosure which comprises the stereoselective reduction of the C12-Ketone of Intermediate 33 to the C12α-Hydroxy Group. The C12-ketone of compound 33, with an adjacent quaternary chiral carbon center at C13, is reduced with six types of reducing agents: (1) diisobutylaluminum hydride (DIBAL), (2) NaBH4, (3) NaBH4 with CeCl3, (4) LiAlH4, (5) lithium triethylborohydride (Superhydride), and (6) lithium tri-sec-butylborohydride (L-Selectride). Proton NMR analysis of the C18-methyl region (δ 0.82-0.96 ppm)

allows quantification of the stereoselectivities of each reducing agent (FIG. 8). Our previous studies with the reduction of a C7-ketone, allowed for a similar prediction in stereoselectivity in the reduction of the C12-ketone. Moreover, a Newman projection analysis predicts that the delivery of a sterically hindered hydride source at the C12-ketone is more favorable through the β-face, yielding primarily the 12α-hydroxy product as the major stereoisomer (FIG. 9, Pathway a.). Table 1 summarizes the results of the different reducing conditions. Both lithium tri-sec-butylborohydride (i.e. L-Selectride) and lithium triethylborohydride (i.e. Superhydride) were selective for the 12α-hydroxy epimer (compound 34) as the major product.

FIG. 12 illustrates the reduction of Ketone 33 with different reducing agents.

Figure 13:
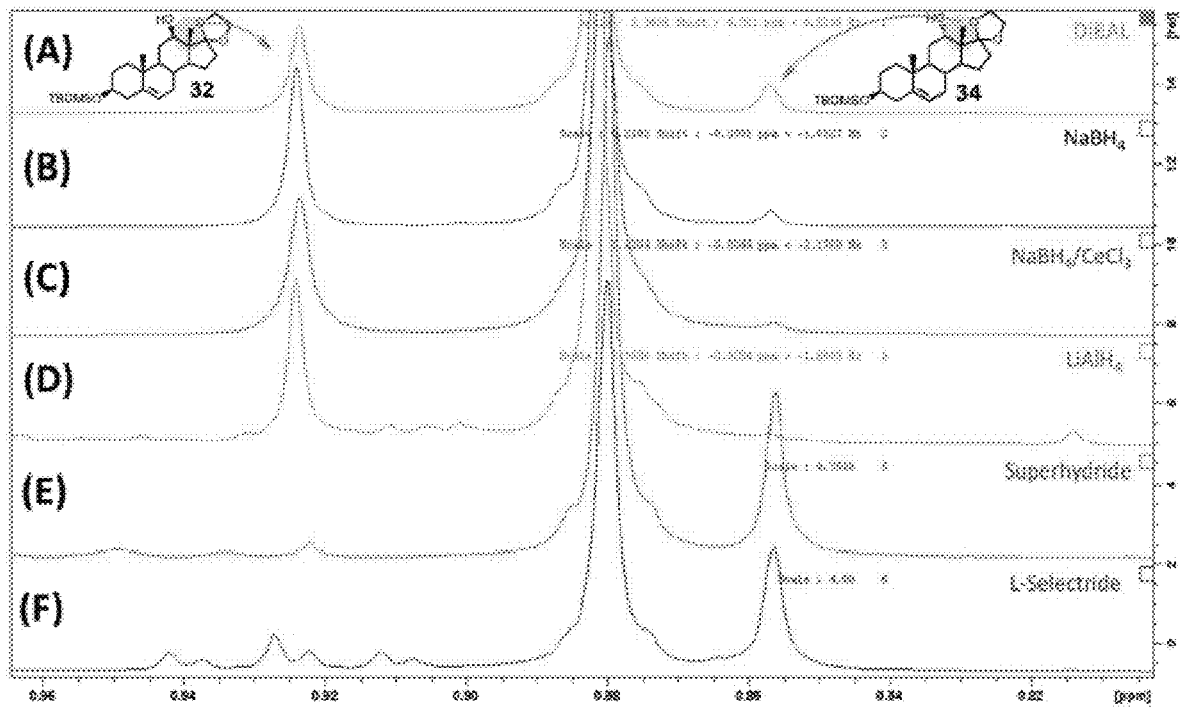
FIG. 13 illustrates the $^1$H NMR analysis of the C18-methyl region of the crude material for each entry.

Turning to FIG. 13, another embodiment of the present disclosure is illustrated. $^1$H NMR analysis of the C18-methyl region of the crude material for each entry (δ 0.86 ppm corresponds to the methyl of the 12α-hydroxy epimer (compound 34) and δ 0.92 ppm corresponds to the methyl of the 12β-hydroxy epimer (compound 32). (A) entry 1: diisobutylaluminum hydride (DIBAL), (B) entry 2: NaBH4, (C) entry 3: NaBH4 with CeCl3, (D) entry 4: LiAlH4, (E) entry 5: lithium triethylborohydride (Superhydride), and (F) entry 6: lithium tri-sec-butylborohydride (L-Selectride). NMR solvent is CDCl3.

FIG. 14 illustrates another embodiment of the present disclosure. A Newman projection analysis at the C12-C13 dihedral angle of intermediate 33, in order to determine the stereoselectivity in the hydride reduction at the C12-ketone. Pathway a. is selective for the 12α-hydroxy epimer product 34, avoiding steric strain while pathway b. is selective for the 12β-hydroxy epimer product 32, avoiding the torsional strain (eclipsing interaction) between the C17-carbon and the C12-oxygen.

Table 1 below summarizes the stereoselectivity of the different reduction conditions tested to yield the C12α-hydroxy epimer 34 or the C12β-hydroxy epimer 32 from C12-ketone 33. The ratios of the 12β-hydroxy and 12α-hydroxy products were determined by integration of the C18-methyl peak of the 1H NMR spectra of the crude reaction material (δ 0.86 ppm for the 12α-hydroxy epimer, and δ 0.92 ppm for the 12β-hydroxy epimer). THF (5 ml) was the solvent, the reaction was run at −78° C. with 30 mg of starting material (Compound 33). CH3OH (5 ml) was the solvent, the reaction was run at 0° C. with 30 mg of starting material (Compound 33). Stereoselective Reduction of the C12-Ketone (Compound 33) with Various Reducing Agents

| Entry | Hydride Source | 12β-Hydroxy (32)$^a$ | 12α-Hydroxy (34)$^a$ |
|---|---|---|---|
| 1$^b$ | DIBAL | 2.9 | 1.0 |
| 2$^c$ | NaBH$_4$ | 9.8 | 1.0 |
| 3$^c$ | NaBH$_4$/CeCl$_3$ | 12 | 1.0 |
| 4$^b$ | LiAlH$_4$ | 14 | 1.0 |
| 5$^b$ | Lithium triethylborohydride | 1.0 | 10 |
| 6$^b$ | Lithium tri-sec-butylborohydride | 1.0 | 9.2 |

Research Design and Methods

FIG. 15 illustrates one embodiment of the P450 8B1 inhibitors. The strategy to selectively inhibit P450 8B1 will involve the synthesis of compounds that mimic the carbon backbone of P450 8B1 substrates but with a nitrogen atom in the location of chemistry (i.e. the 12-position of sterols will contain a nitrogen that can coordinate to the iron active site of P450 8B1). Although the main substrate reported for P450 8B1 is 7α-hydroxycholest-4-en-3-one (see FIG. 1, 3), P450 8B1 from liver microsomes has been shown to have a broad substrate scope with varying oxidation states in the A-ring. The inhibitor structures do not have to be restricted to the 3-keto-Δ4-sterol backbone in the A-ring as shown in FIG. 15.

FIG. 15 illustrates one embodiment of the present disclosure. The P450 8B1 inhibitor introduces a nitrogen atom in the C-ring of the sterol. 12-Aza-cholanetriol compounds have been synthesized by treating a diiodo intermediate with benzylamine. The diiodo intermediate (FIG. 15, 21) can be treated with methylamine to introduce a methylated piperidine derivative in the C-ring (FIG. 15, 22) to use P450 8B1 as an inhibitor. The diiodo intermediate can be obtained from formate 20 (FIG. 15). The odoformate 20 intermediate is derived by treating lactol 19 (FIG. 15) with Suginome-Yamada hypoiodide photolysis conditions. Lactol 19 can be obtained from the chemoselective reduction of the lactone intermediate (18) using DIBAL. The lactone will be afforded from a Baeyer-Villiger oxidation product of ketone 17.

Figure 16:
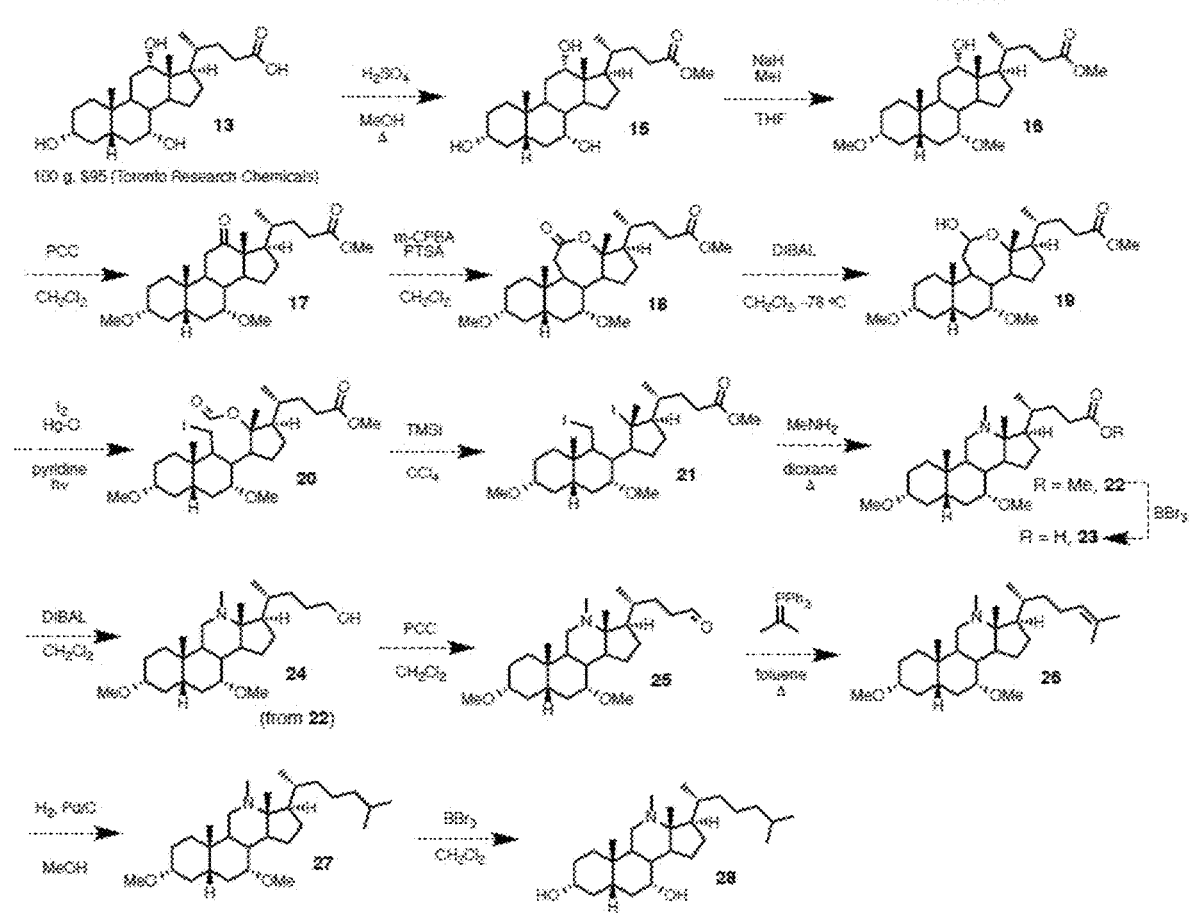
FIG. 16 illustrates the synthesis of an N-methyl piperidine sterol starting from cholic acid.

FIG. 16 illustrates the synthesis of an N-methyl piperidine sterol (28) starting from cholic acid (13) is shown. This piperidine analog can mimic a substrate of P450 8B1.

Synthesis of an Azepane P450 8B1 Inhibitor

FIG. 17 illustrates synthesis of an azepane analog of cholic acid (33), which can be a P450 8B1 inhibitor. Synthesis of lactam-analogs of 7-deoxycholic acid has been reported through a Tamura-Beckmann rearrangement of an oxime intermediate. The protocol to access the lactam (FIG. 17, 30) treats oxime 29 with SOCl2. The resulting lactam can be reduced with lithium aluminum hydride to afford a more Lewis basic azepane analog (33), which can be a stronger ligand for P450 8B1 relative to the lactam.

Water Solubility of Synthesized Inhibitor.

Inhibitors tested in cell culture can comprise water solubility issues. In one embodiment of this disclosure, the small molecule can be as a prodrug. For instance, hydroxyl groups of insoluble drugs can be functionalized as the phosphonooxymethyl, sulfate, or phosphate groups to enhance water solubility.

Synthesis of Deuterated Substrates.

Turning to FIG. 18, one embodiment of the present disclosure is illustrated. The synthesis of deuterated chenodeoxycholic acid compounds (35 and 38) as substrates for P450 8B1 is shown. Deuterated sterol substrates can be synthesized for use to measure kinetic isotope effects for the C—H abstraction step in the P450 catalytic cycle. As shown in FIG. 18, the strategy of deuterium incorporation can involve the substitution of the 12-position with a leaving group (such as a mesylate or a halogen) and treating these intermediates with zinc and deuterated acetic acid]. If the C—H abstraction step is very rate limiting (kH/kD>7), then these deuterated substrates can be used as P450 8B1 inhibitors. An interesting aspect of using a 12α-monodeuterated substrate (FIG. 18, compound 35) for P450 8B1 is that P450 8B1 can undergo metabolic switching upon deuteration of the 12α-proton. This phenomenon was observed with P450 17A1, when the 16α-position was deuterated on the substrate, and the enzyme had switched and abstracted the 16β-hydrogen atom of the substrate as determined by analysis of the products by mass spectrometry. This kind of switching does not always occur in P450 enzymes, and one example is P450 3A4 and its 6β-deuterotesosterone substrate.

Synthesis of 12-Desoxy Sterol Substrates.

P450 8B1 can have a large substrate scope, which has been illustrated with liver microsomes as the enzyme source and not with the purified P450 8B1. Synthesizing various sterol compounds along the bile acid biosynthesis pathway that lack substitution on the 12-position can create substrates for P450 8B1. Although there have been previous attempts to synthesize substrate analogs for P450 8B1, these compounds were not naturally occurring compounds found in the bile acid biosynthesis pathway. Moreover, most of these 12-desoxy compounds found in the biosynthesis of 12-desoxy bile acids are commercially available (Avanti Lipids, Inc.).

Biochemical Characterization of Cytochrome P450 8B1

P450 8B1 Heterologous Expression and Purification.

The advancement of recombinant DNA technology has facilitated the heterologous expression of human P450 enzymes in bacteria. The human P450 8B1 gene sequence with 6-histidine residues on the C-terminus with *Escherichia coli* codon optimization will be inserted in the pCW vector and ordered through Genewiz. The plasmid can be transformed into bacteria and the expression of the protein can be induced with isopropyl β-D-1-thiogalactopyranoside (IPTG). Purification steps can be followed with careful monitoring of the P450 Soret band between each step (e.g. centrifugation, cation, membrane solubilization, Ni-nitriloacetic acid affinity column chromatography then dialysis).

Testing for P450 8B1 Inhibitors

When ligands containing nitrogen heteroatoms bind to P450 enzymes, this event usually results in a shift in the UV-absorbance band of the heme center. Taking the difference between this shift in absorption of the Soret band and unperturbed enzyme is termed a "Type II" binding difference spectrum. Monitoring the relative changes in the spectra based on different ligand concentrations can be used to measure dissociation constants (Kd) to measure the affinity of the ligand onto the P450 protein. Moreover, the inhibitor constant (Ki) will also be measured for each synthesized inhibitor by running standard activity assays in the presence of varying concentrations of inhibitor. If none of the synthesized inhibitors have desired potency for P450 8B1, then High-Throughput/Content Screening (HTS) can be employed along with using the available compound library. A library of small molecules can be screened for binding based on the P450 type II binding spectra. A plate reader can be used to monitor absorbance changes upon ligand binding.

P450 8B1 Crystallography. X-ray crystallography is a common technique to understand the 3-dimensional structure of the protein. There is no current structure for P450 8B1; however, there is a reported crystal structure of P450 8A1 available, which has 43% sequence identity with P450 8B1. Similar modifications in the N-terminus of P450 8B1 can be made by replacing the first 18 amino acid residues with MAKKTSS. Microseeding, hanging and sitting drop, and vapor diffusion methods to crystallize P450 8B1 with its substrate or inhibitor bound can be employed. Also, X-ray crystallography equipped with crystal screens can be used.

P450 8B1 Kinetic Studies and Global Fitting of Rates

There has been no thorough kinetic characterization of P450 8B1, which is probably due to the lack of a heterologous expression and purification system. With purified protein available, techniques can be used to dissect individual rates in the enzymatic catalytic cycle. P450 enzymes exhibit a shift in the UV-Vis absorbance spectrum upon substrate binding and taking the subtracting the spectra obtained in the absence and presence of ligand, a difference spectrum is obtained to afford a "Type I" spectrum. Using a stopped-flow instrument, the substrate-binding rate can be measured with one syringe containing P450 8B1 enzyme and the other syringe containing substrate. In a similar fashion, the product-binding rate can be measured. The product release rate can be measured using the enzyme-product complex in one syringe and a synthesized inhibitor. If there is no successful inhibitor synthesized, the use of other P450 inhibitors that do not have selectivity such as ketoconazole can be explored.

Additionally, the rate from [ES] to [EP] can be measured and burst phase kinetics can be monitored using a rapid chemical quench apparatus.

For the rapid chemical quench experiment: one syringe can contain phospholipid, P450 8B1, P450 reductase, and substrate while the second syringe can contain NADPH. The quenching syringe can contain either acid or organic solvent to stop the reaction.

The reaction loop lengths can be varied to change the reaction time within the millisecond to minute time scale. Deuterated substrates can be used to measure kinetic isotope effects of the C—H abstraction process for P450 8B1. Steady state kinetic parameters can be measured to determine how rate limiting the C—H abstraction step is in the P450 catalytic cycle.

P450 8B1 and P450 8A1—the Electron Transfer Process

The protein with the closest sequence identity to P450 8B1 is P450 8A1 (43% sequence identity). P450 8A1 (prostacyclin synthase) is the cytochrome P450 enzyme that converts prostaglandin H2 to prostacyclin, an inhibitor of platelet aggregation and a potent vasodilator. An intriguing aspect of P450 8A1 is that it is one of only two of all human P450 enzymes that does not interact with a reducing partner (P450 5A1 is the other one) to generate Compound I. From a multiple sequence alignment, the differences between P450s 8A1 and 8B1 have been identified. Chimeric P450s (swapping sequences between P450s 8A1 and 8B1) and site directed mutants can be generated to understand what makes P450 8A1 not interact with reductase. In order to confirm P450 8A1 does not interact with P450 reductase, heterologously expression and purification of these proteins can be performed.

Human P450 reductase is available through commercial sources (Sigma Aldrich, Thermo Fisher). Understanding the ability of P450 reductase to transfer electrons to the P450 enzyme is clinically important because there are reports of P450 deficient mutations reported that may be caused by a disruption of this protein interaction.

FIG. 19 illustrates the multiple sequence alignment of P450s 8A1 and 8B1. Positively charged residues in P450 8B1 are marked with an "*", which correspond to positive charges responsible for P450 reductase interaction in P450 19A1.

From a multiple sequence alignment between P450s 8A1, 8B1, and 19A1 (P450 19A1 not shown in FIG. 19), we have noticed that P450 8A1 (but not P450 8B1) is missing two positively charged residues that have been previously identified to be important for interaction with P450 reductase and P450. P450 8A1 possesses tryptophan-88 and serine-235, which correspond to lysine-91 and arginine-234 in P450 8B1 (FIG. 19). These residues correspond to lysine residues (positions −108 and −262) in P450 19A1, which interacts with reductase through computational modeling and mutagenesis studies. Mutating these neutrally charged amino acid residues in P450 8A1 to lysine or arginine residues can enable P450 reductase interaction.

Evidence to Support Electron Transfer Between P450 and P450 Reductase

Although it is common knowledge that P450 8A1 does not interact with a reducing partner, there is no clear evidence supporting this lack of interaction.

Figure 20:
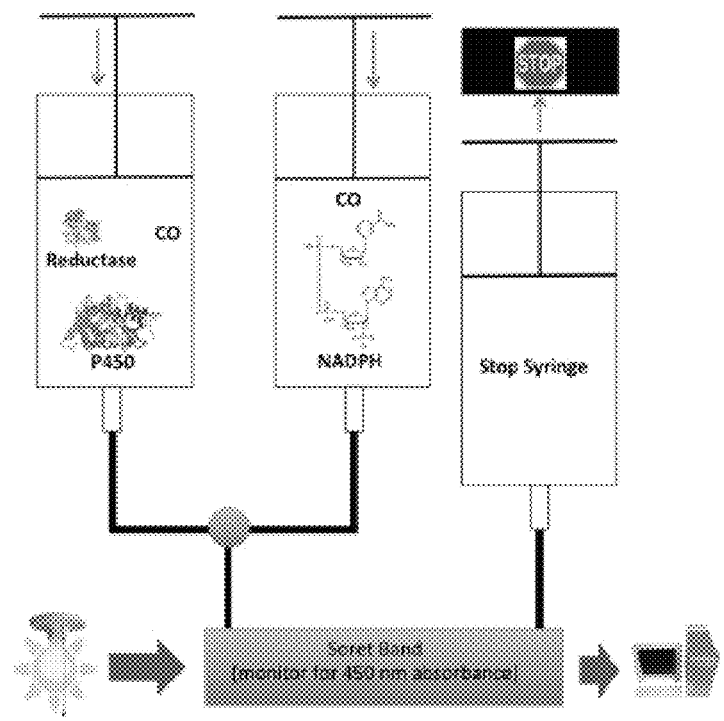
FIG. 20 illustrates the test for determining if P450 reductase will transfer electrons to P450 8A1 using a stopped-flow apparatus.

Turning to FIG. 20, one established way to show the first electron transfer between P450 reductase and the P450 enzyme is to monitor the 450 nm Soret band upon carbon monoxide (CO) binding in a stopped-flow instrument with two syringes is illustrated. CO has affinity for the reduced form of iron ($Fe^{+2}$) and not for the oxidized (non-reduced) form ($Fe^{+3}$). One syringe will contain the P450 enzyme and P450 reductase saturated with CO, and the second syringe will contain NADPH saturated with CO. P450 8A1 will not show an absorbance at 450 nm while P450 8B1 will. From various mutant proteins generated, the reductase interaction can be conferred into P450 8A1 mutants.

Figure 21:
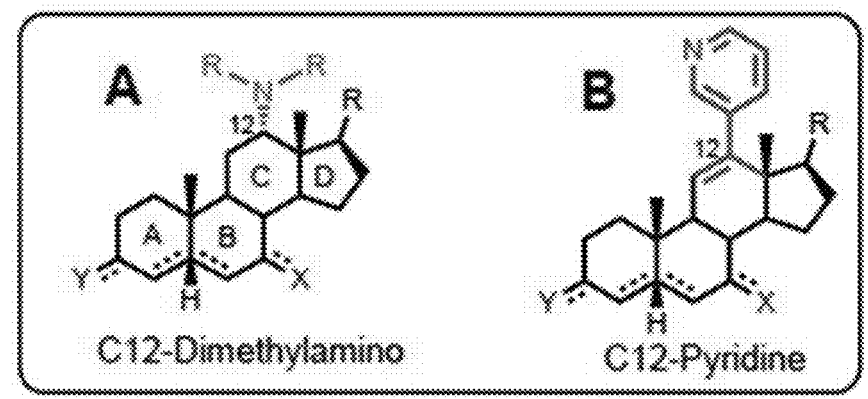
FIG. 21 illustrates the synthesis of C12-pyridine steroid anologs.
Figure 21:
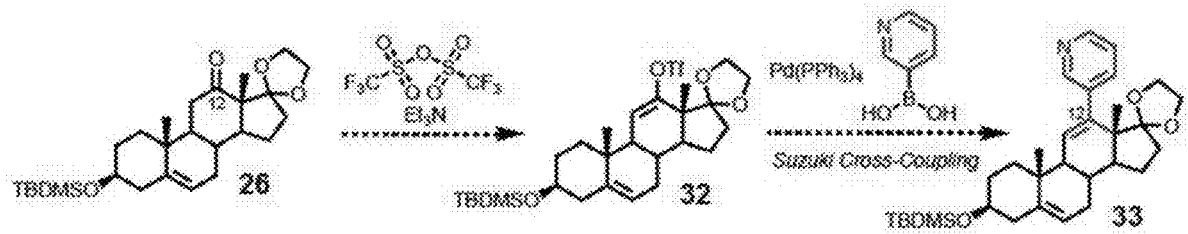

FIG. 21 illustrates the synthesis of C12-pyridine steroid analogs (26, 32, 33).

Figure 22:
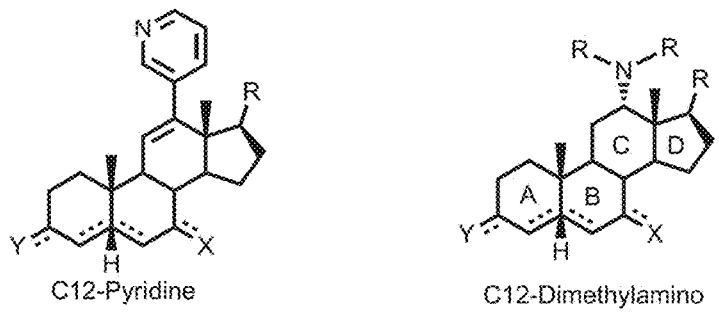
FIG. 22 illustrates the synthesis 11-oxygenated versions and C11-keto derivative that can be functionalized with a heterocycle for creation of the P450 11B2 and P450 11B1 inhibitors.
Figure 22:
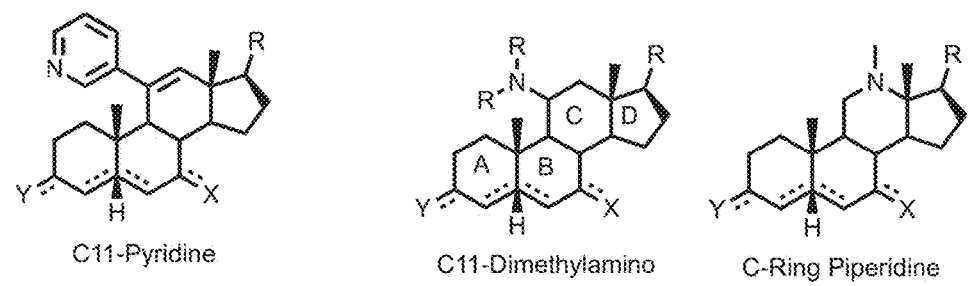
Figure 22:
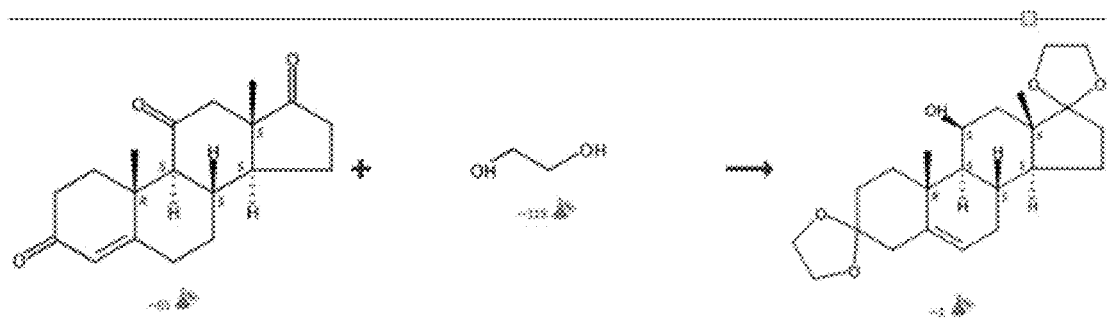

FIG. 22 illustrates the synthesis of 11-oxygenated versions and makes a C11-keto derivative that can be functionalized with a heterocycle be a P450 11B2 and P450 11B1 inhibitor.

Figure 23:
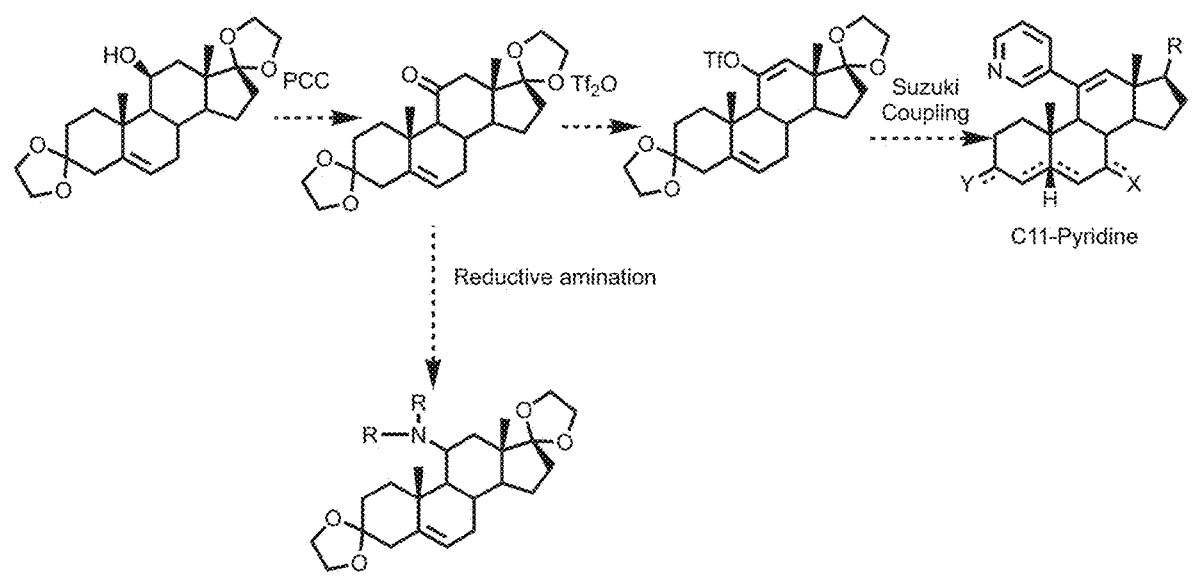
FIG. 23 illustrates the creation C11-heteroatom and C11-heterocyclic analogs.
Figure 24:
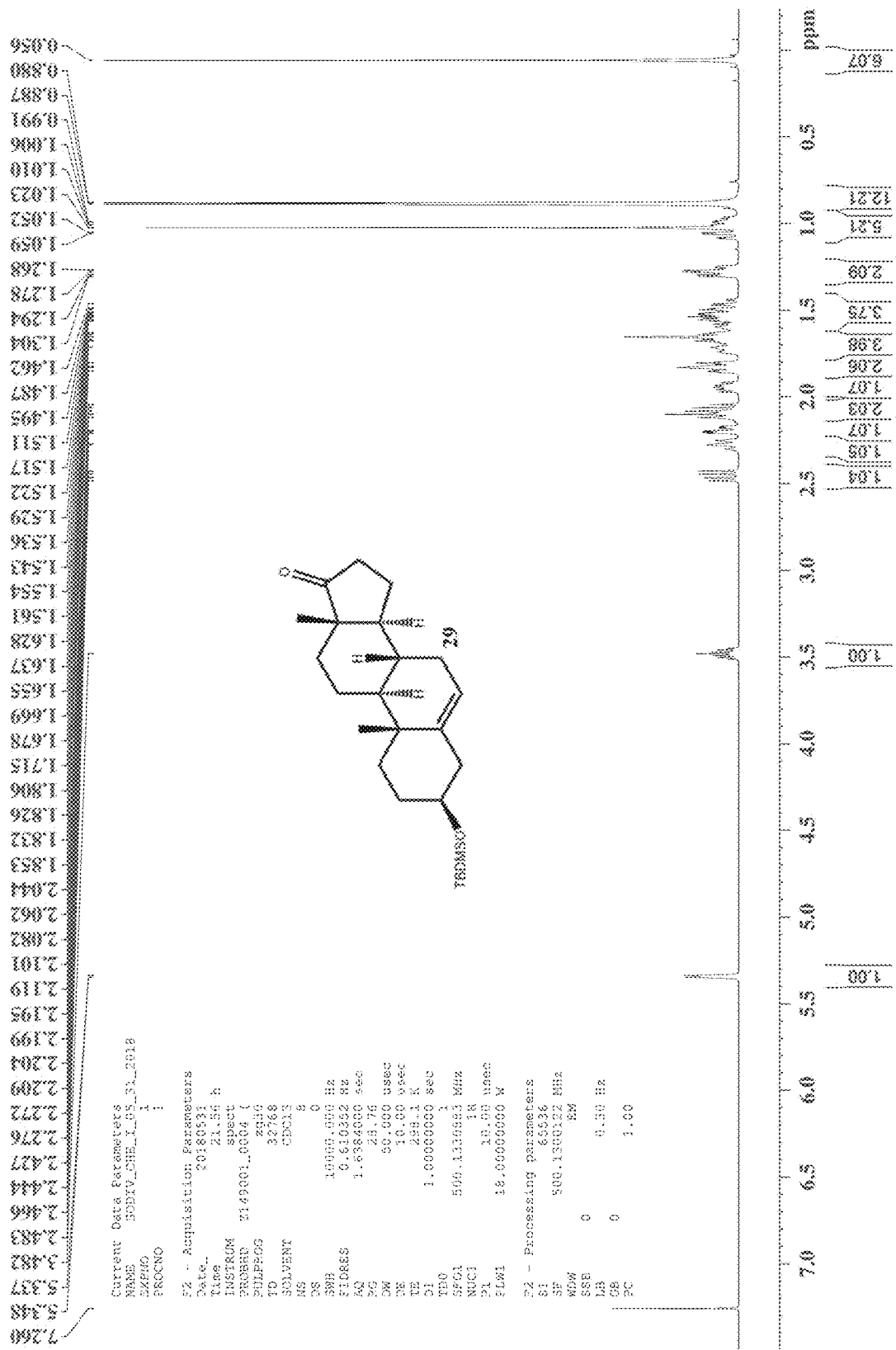
FIGS. 24-27 show $^1$H and $^{13}$C NMR, HRMS, and IR spectra of Compound 29.
Figure 25:
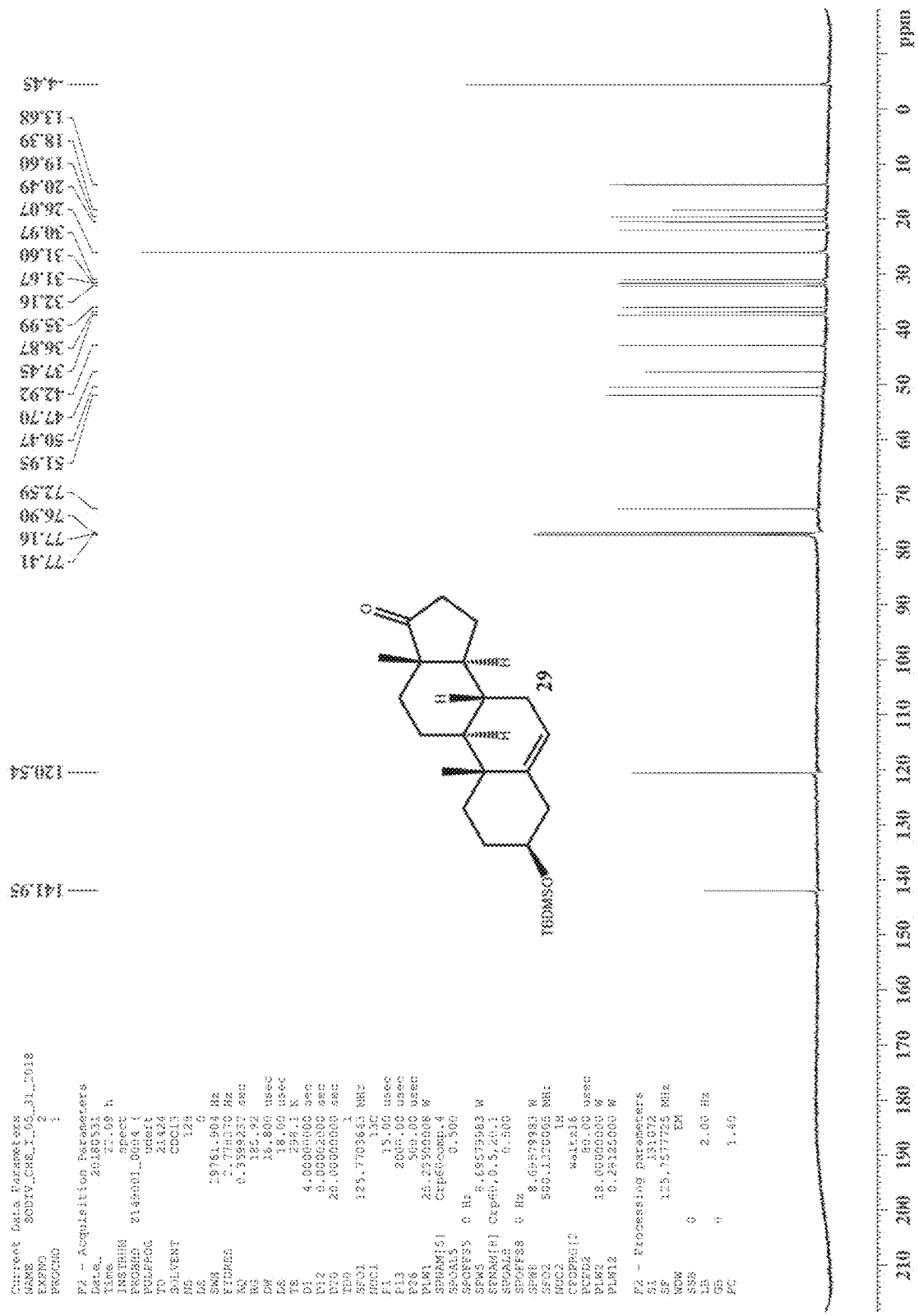
Figure 26:
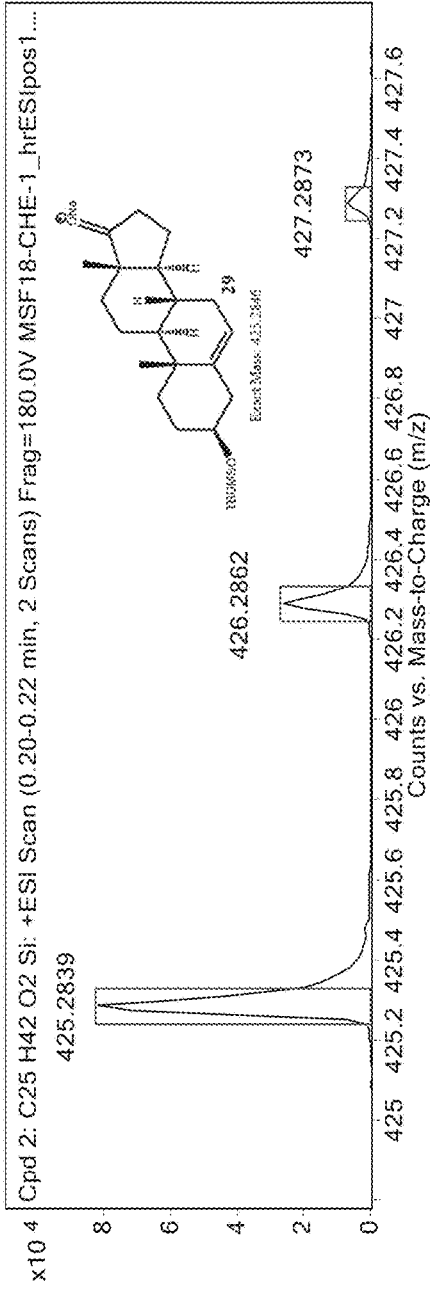
Figure 27:
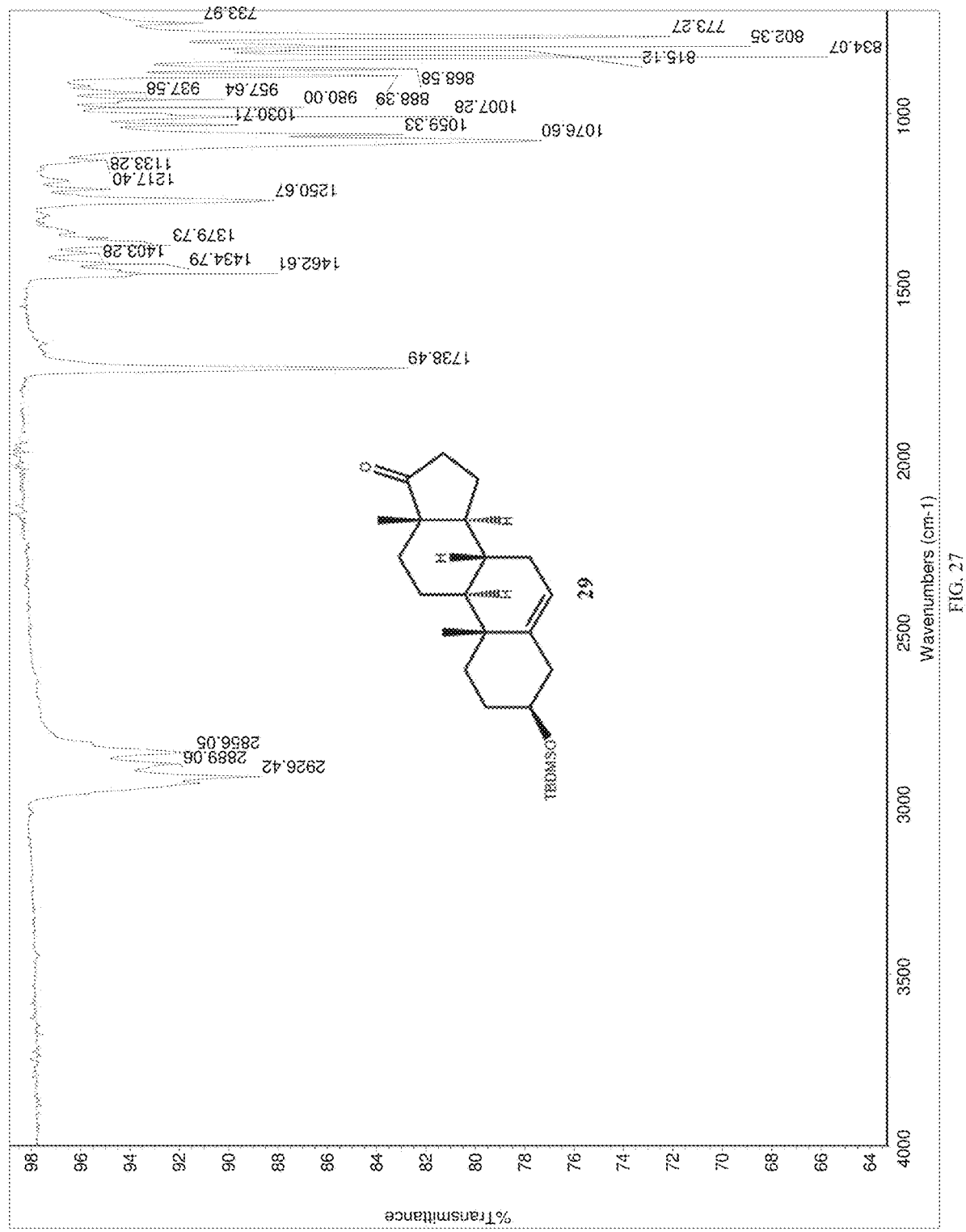
Figure 28:
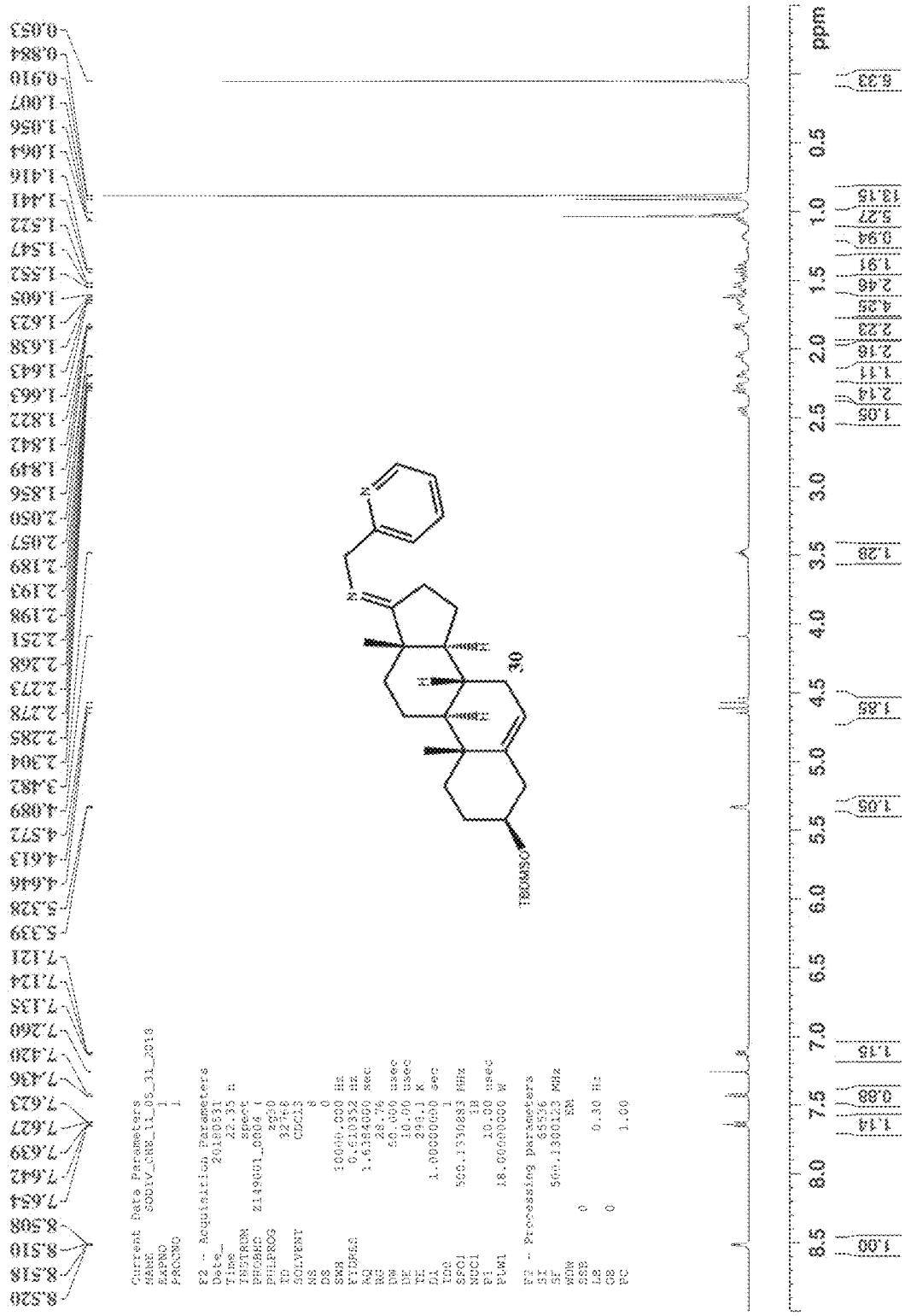
FIGS. 28-31 show $^1$H and $^{13}$C NMR, HRMS, and IR spectra of Compound 30.
Figure 29:
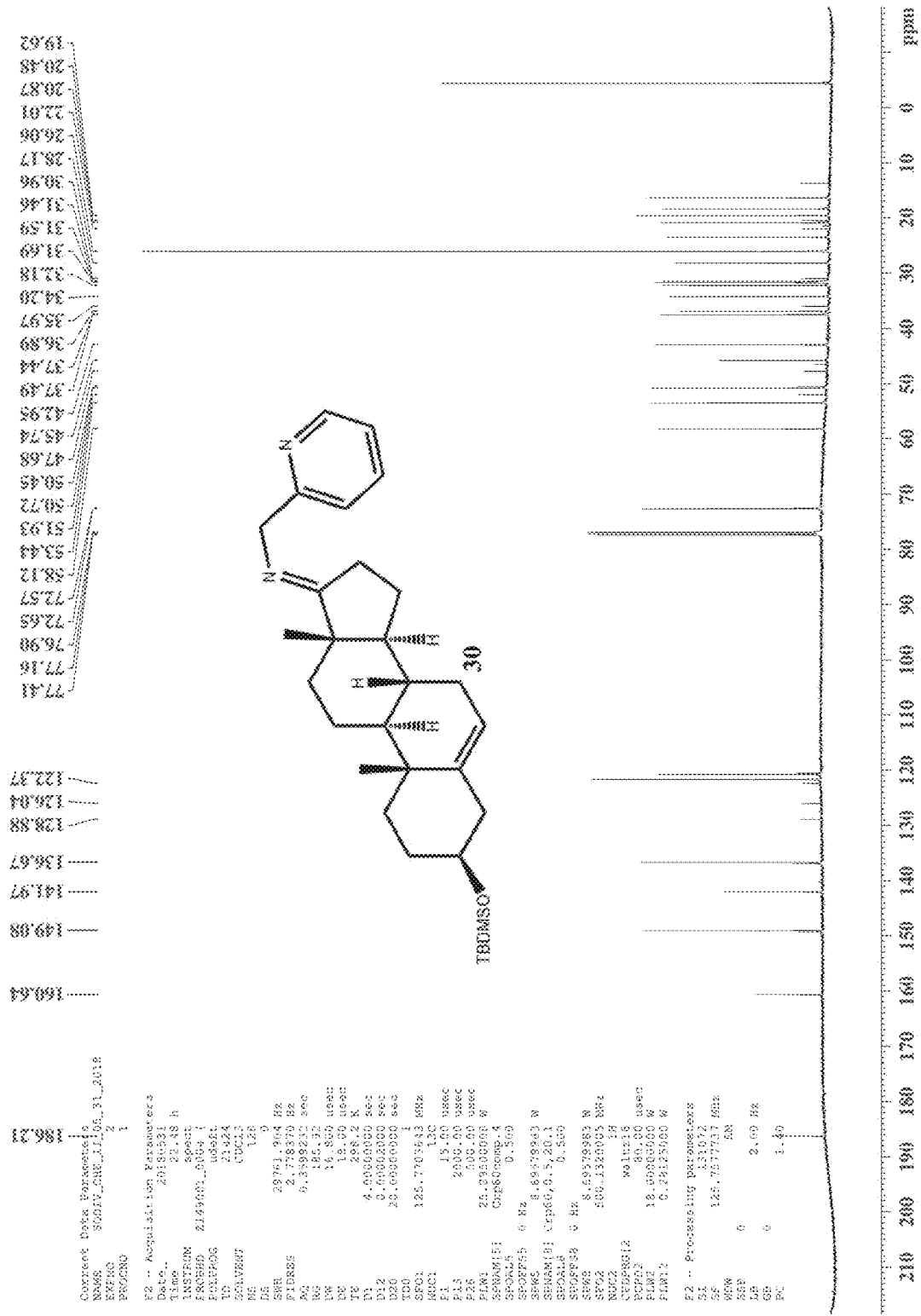
Figure 30:
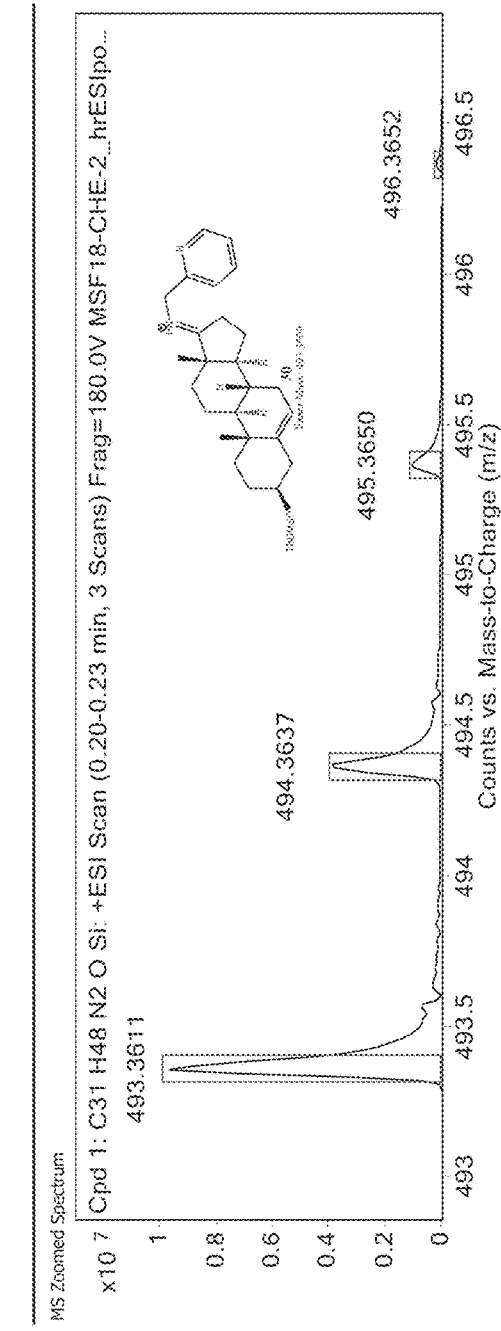
Figure 31:
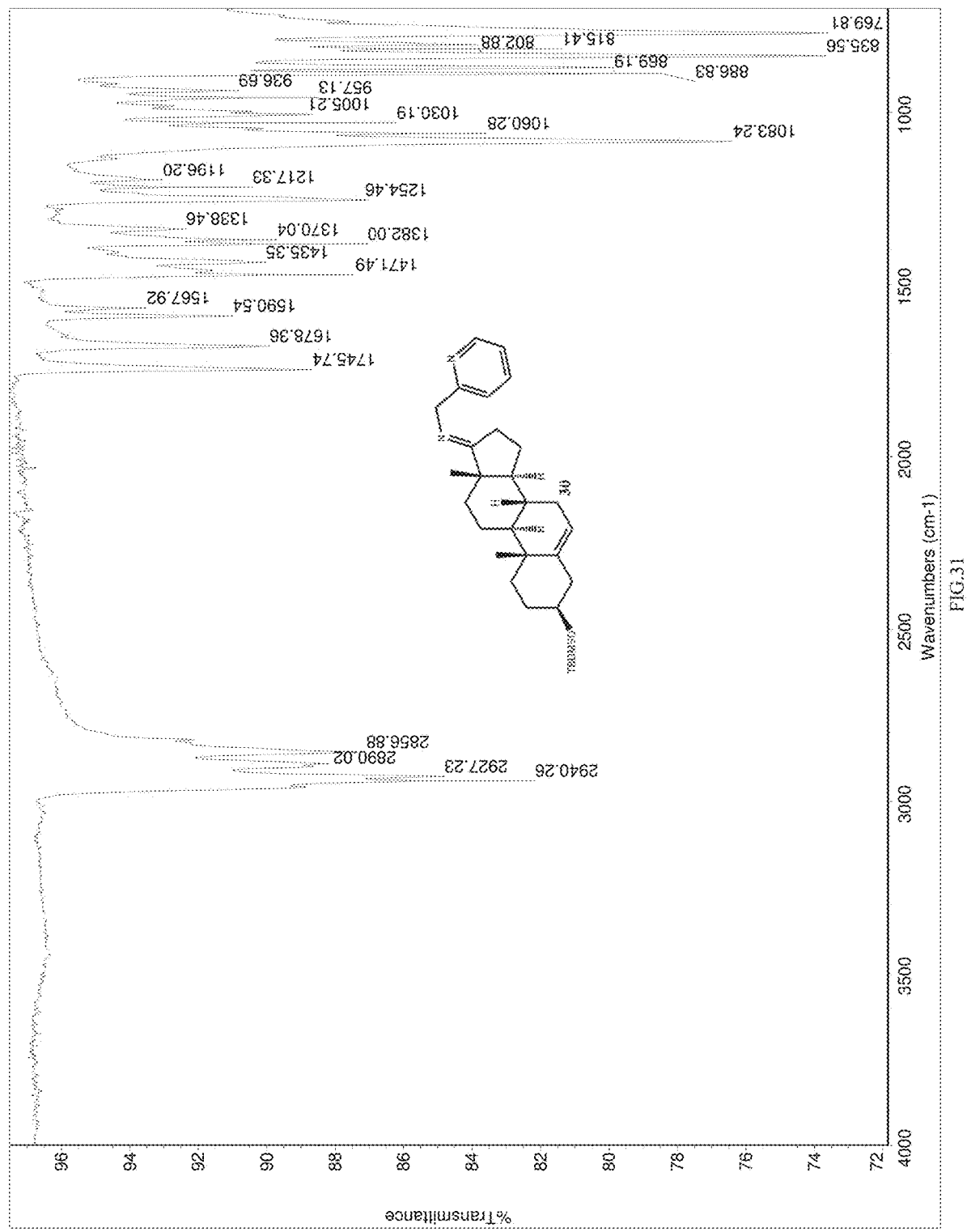
Figure 32:
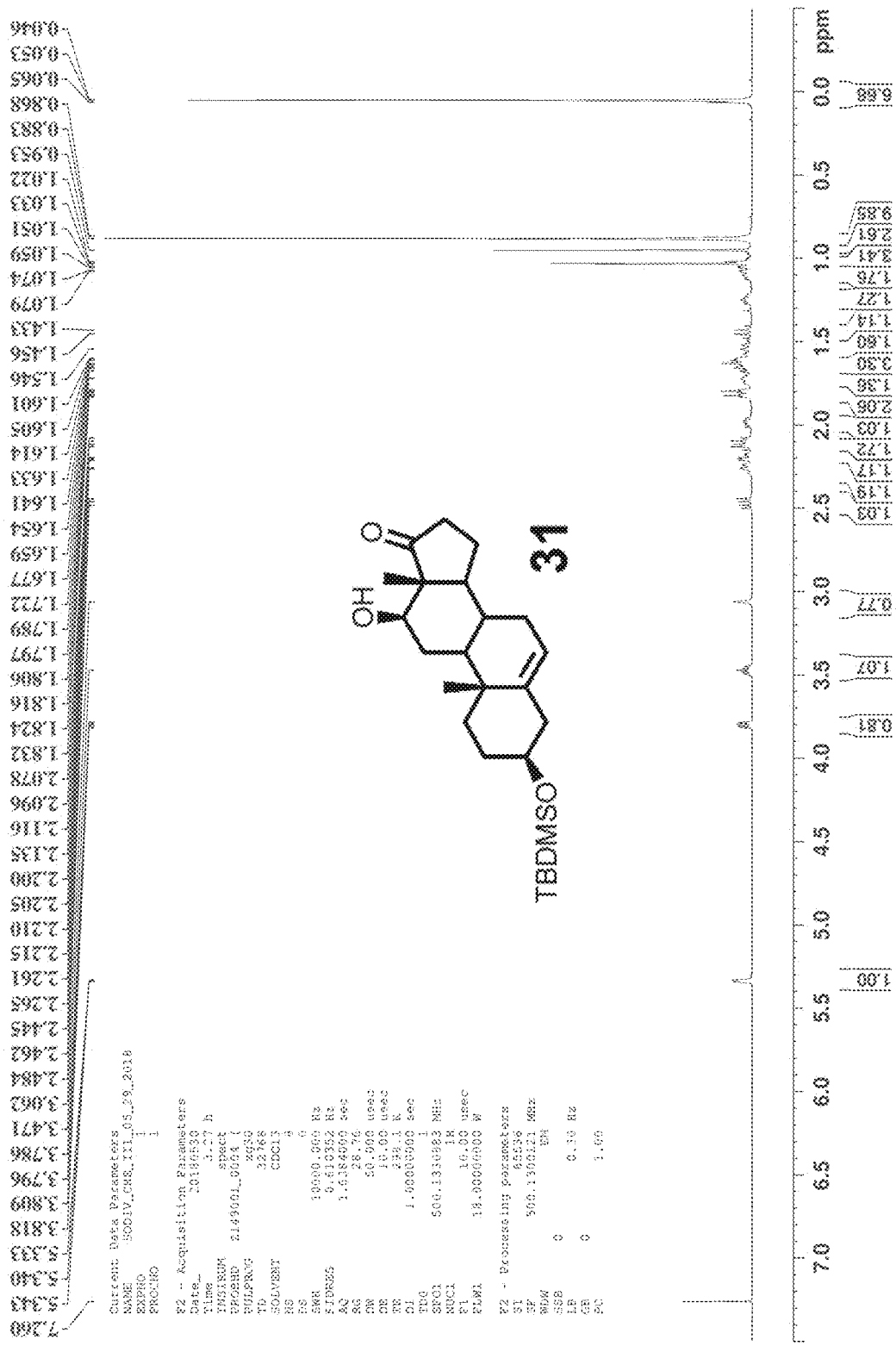
FIGS. 32-35 show $^1$H and $^{13}$C NMR, HRMS, and IR spectra of Compound 31.
Figure 33:
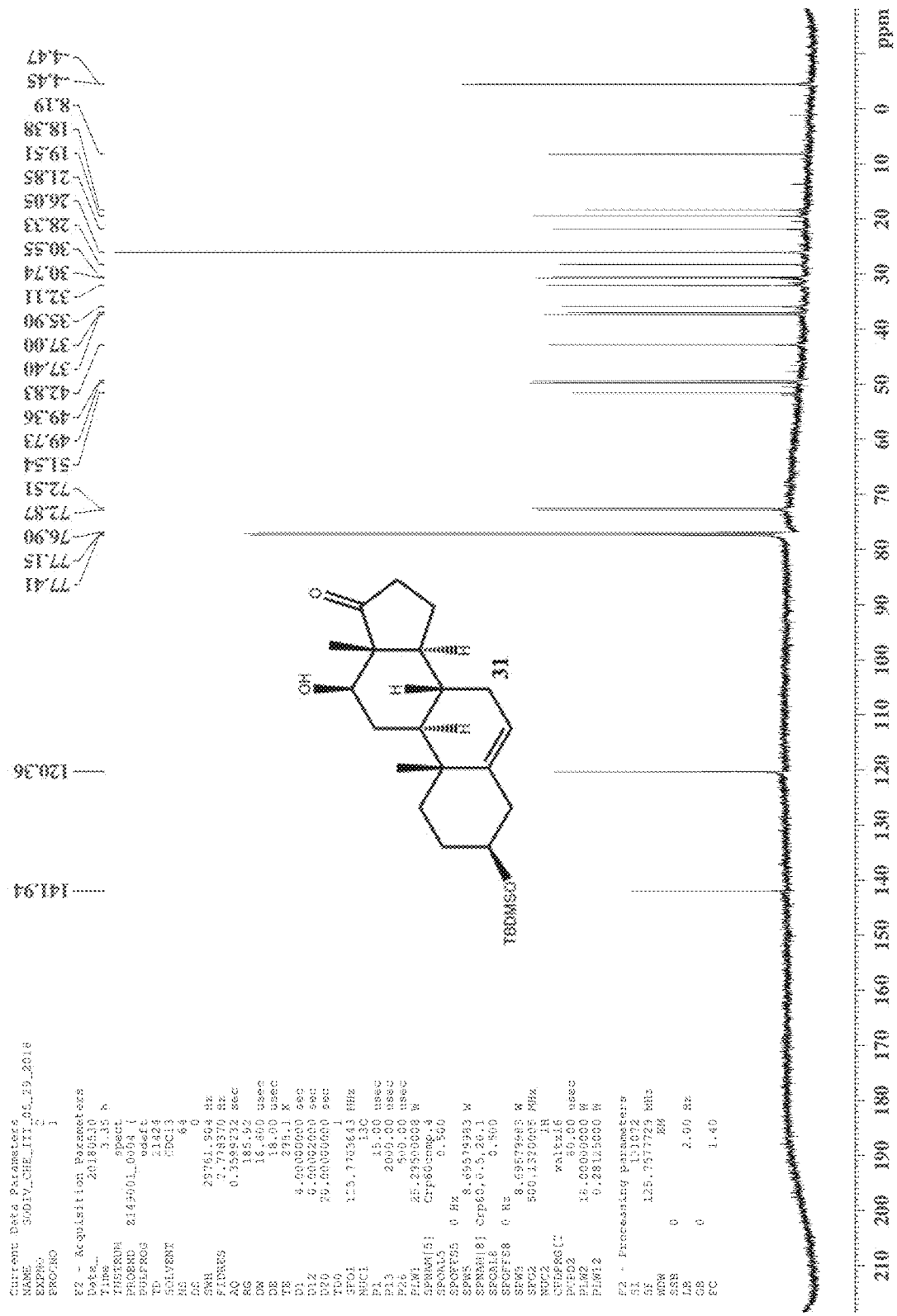
Figure 34:
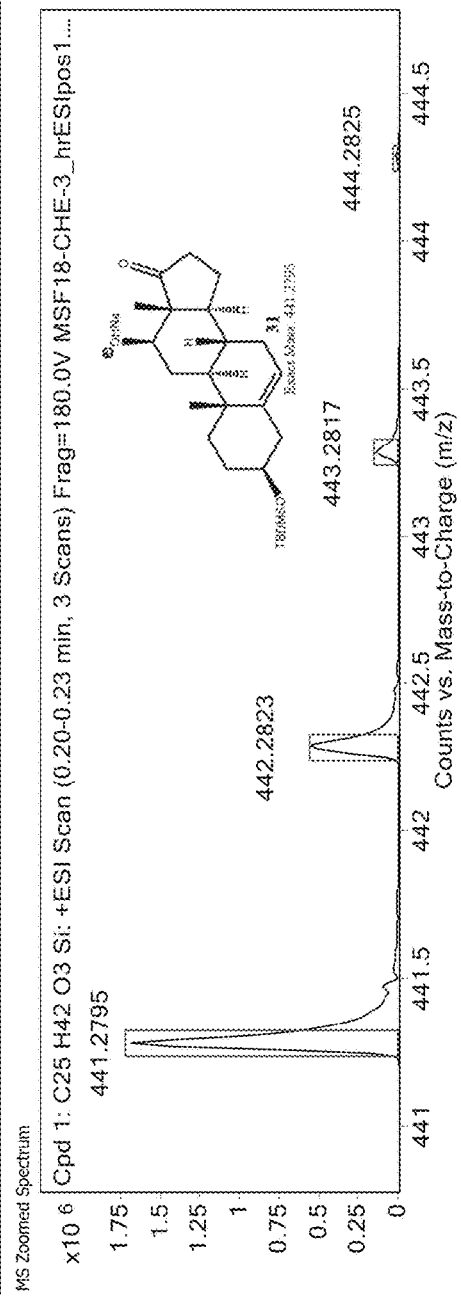
Figure 35:
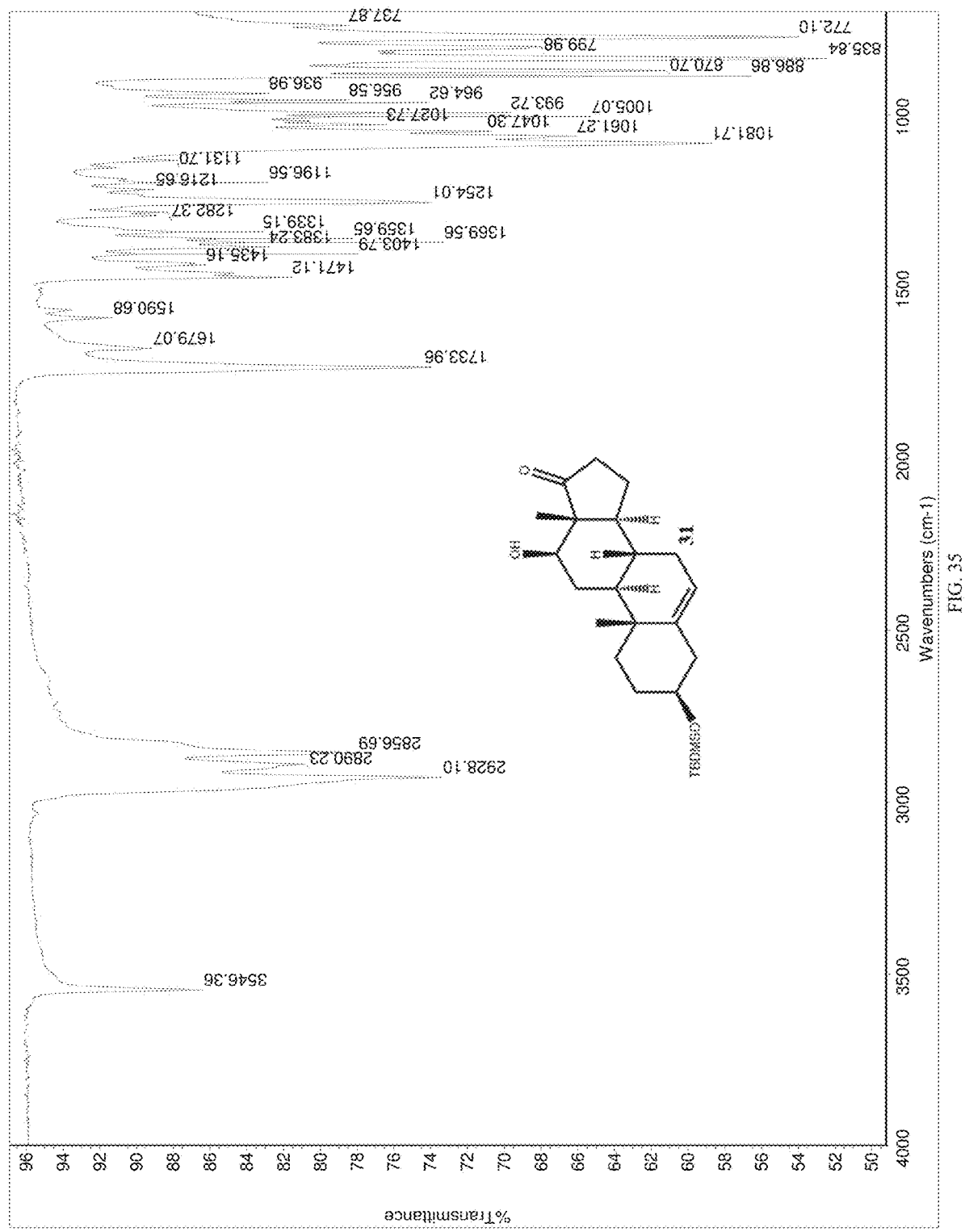
Figure 36:
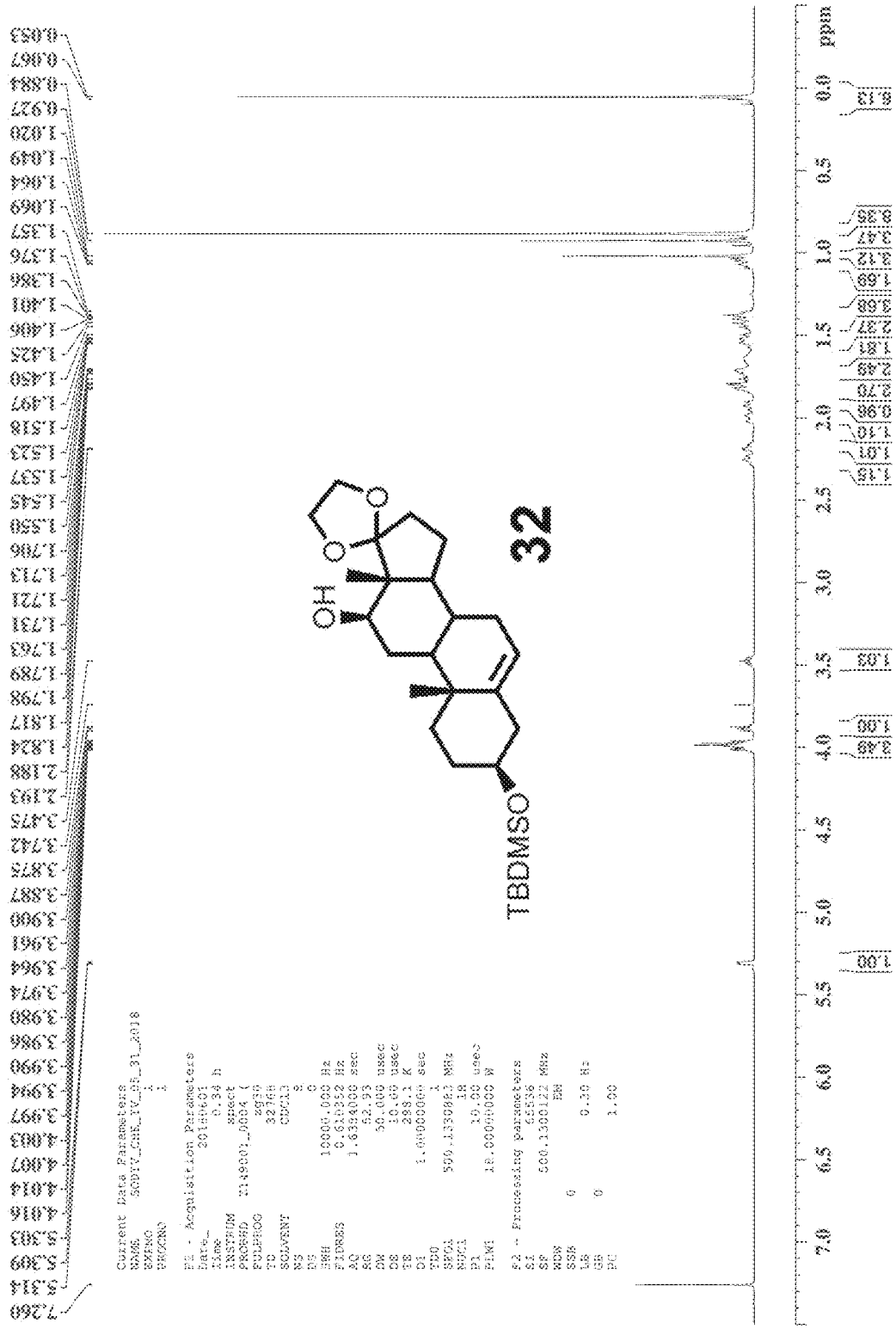
FIGS. 36-39 show $^1$H and $^{13}$C NMR, HRMS, and IR spectra of Compound 32.
Figure 37:
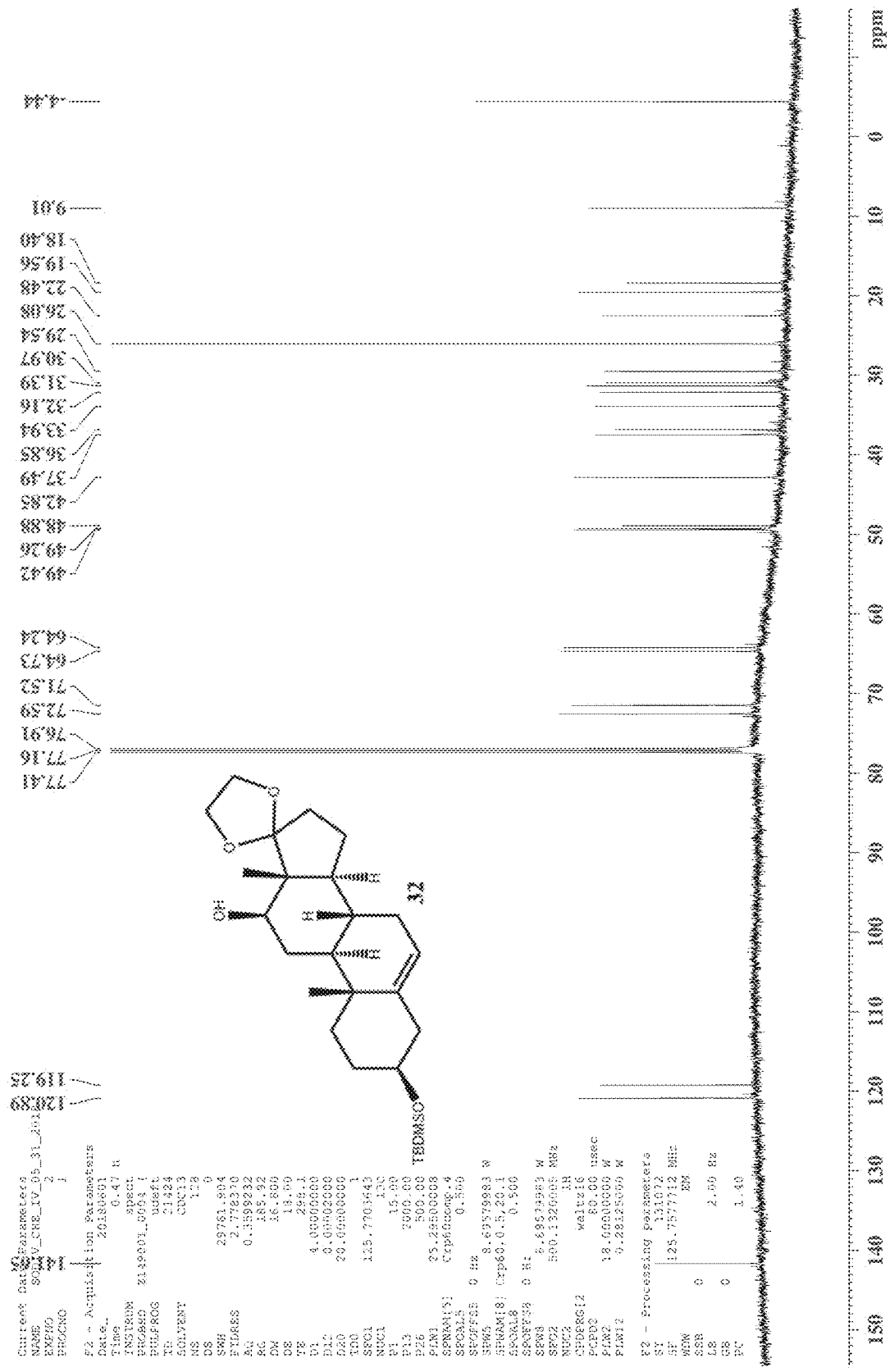
Figure 38:
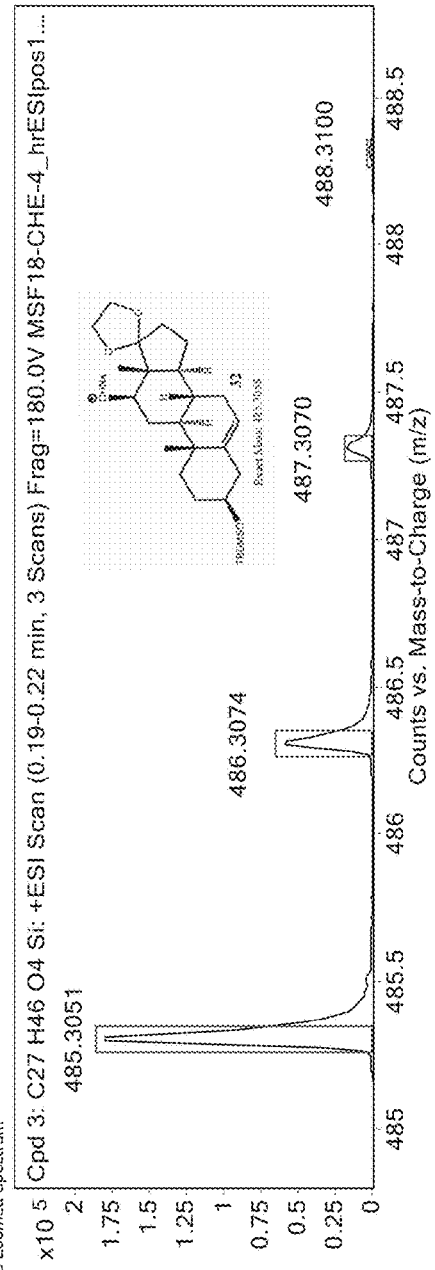
Figure 39:
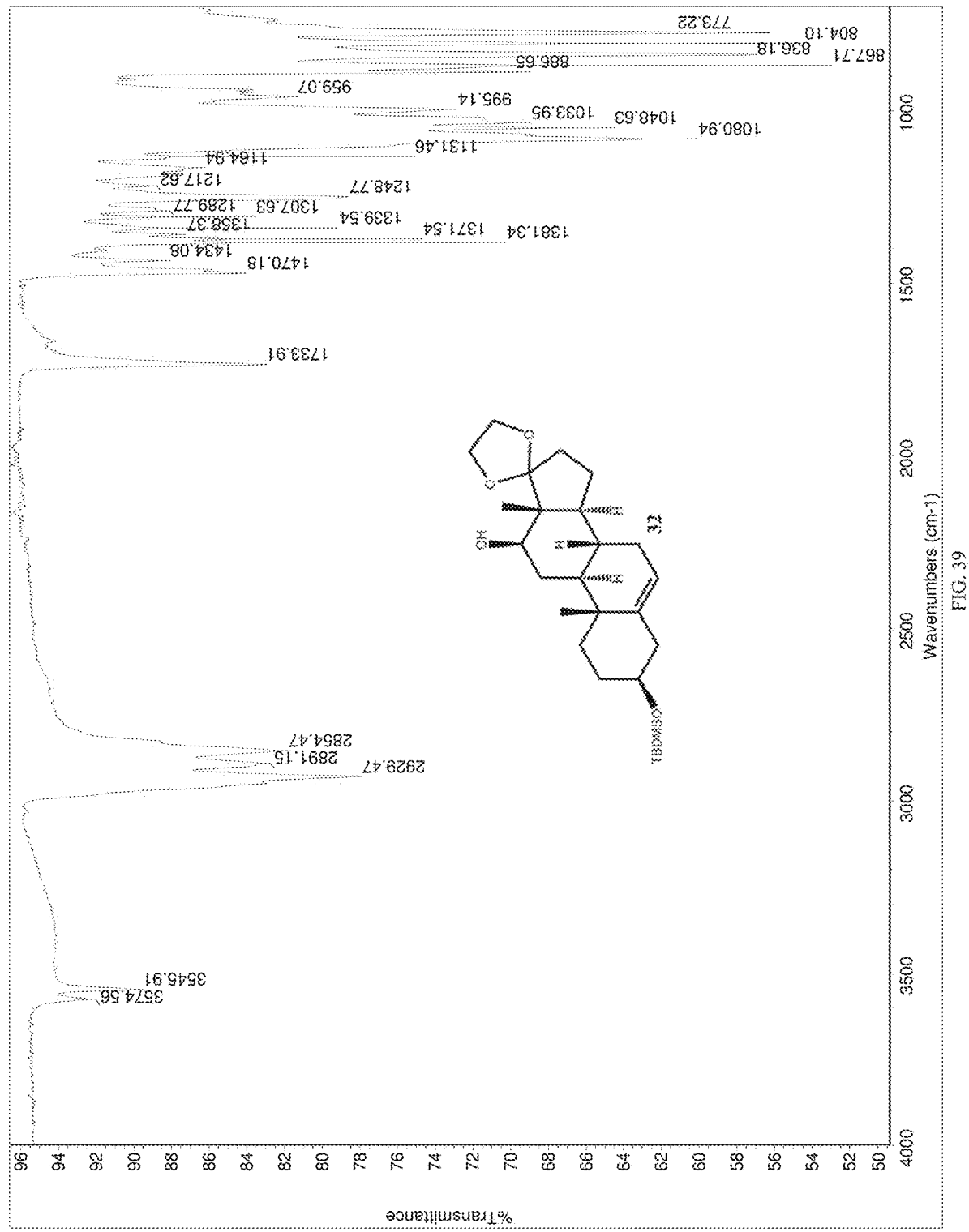
Figure 40:
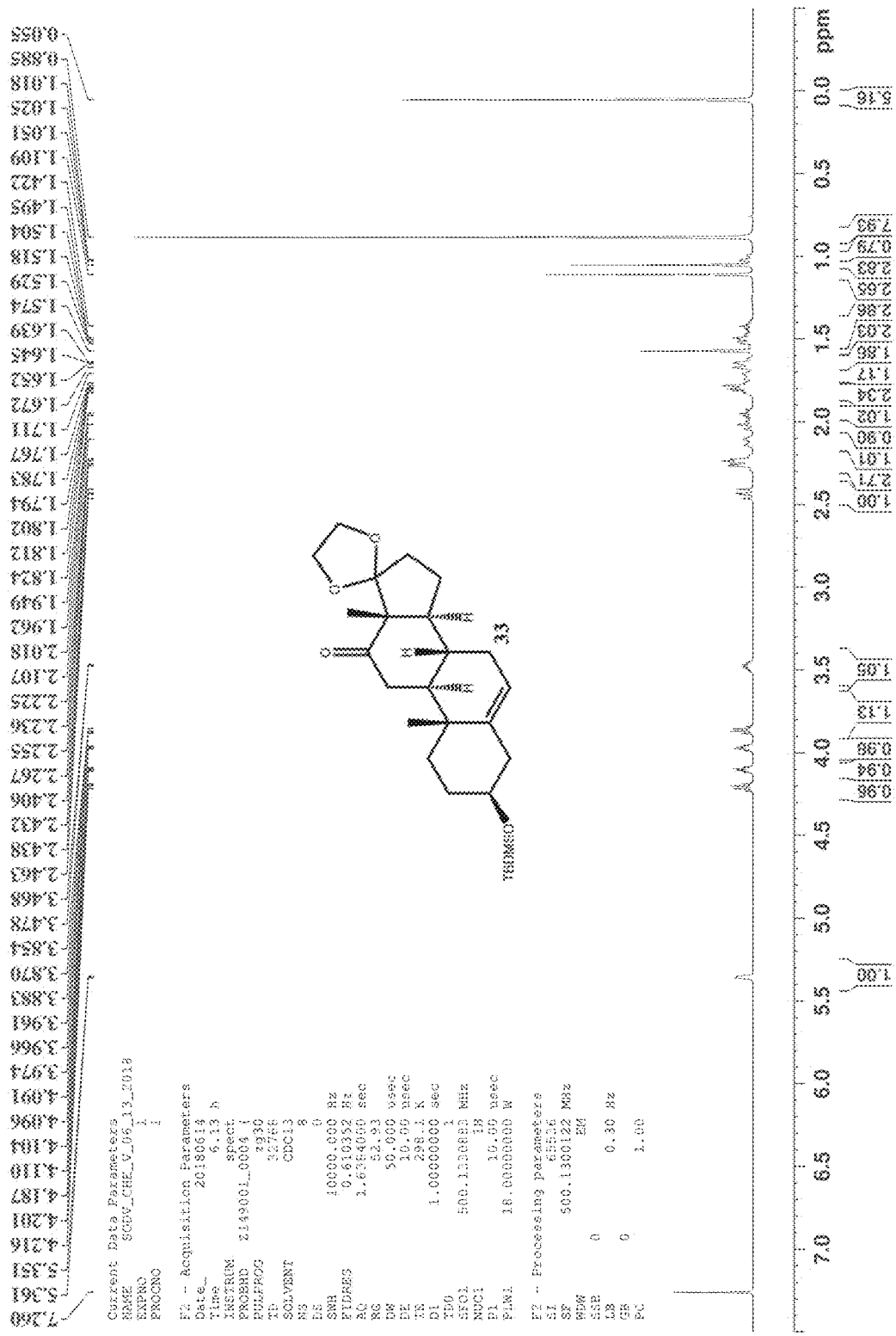
FIGS. 40-43 show $^1$H and $^{13}$C NMR, HRMS, and IR spectra of Compound 33.
Figure 41:
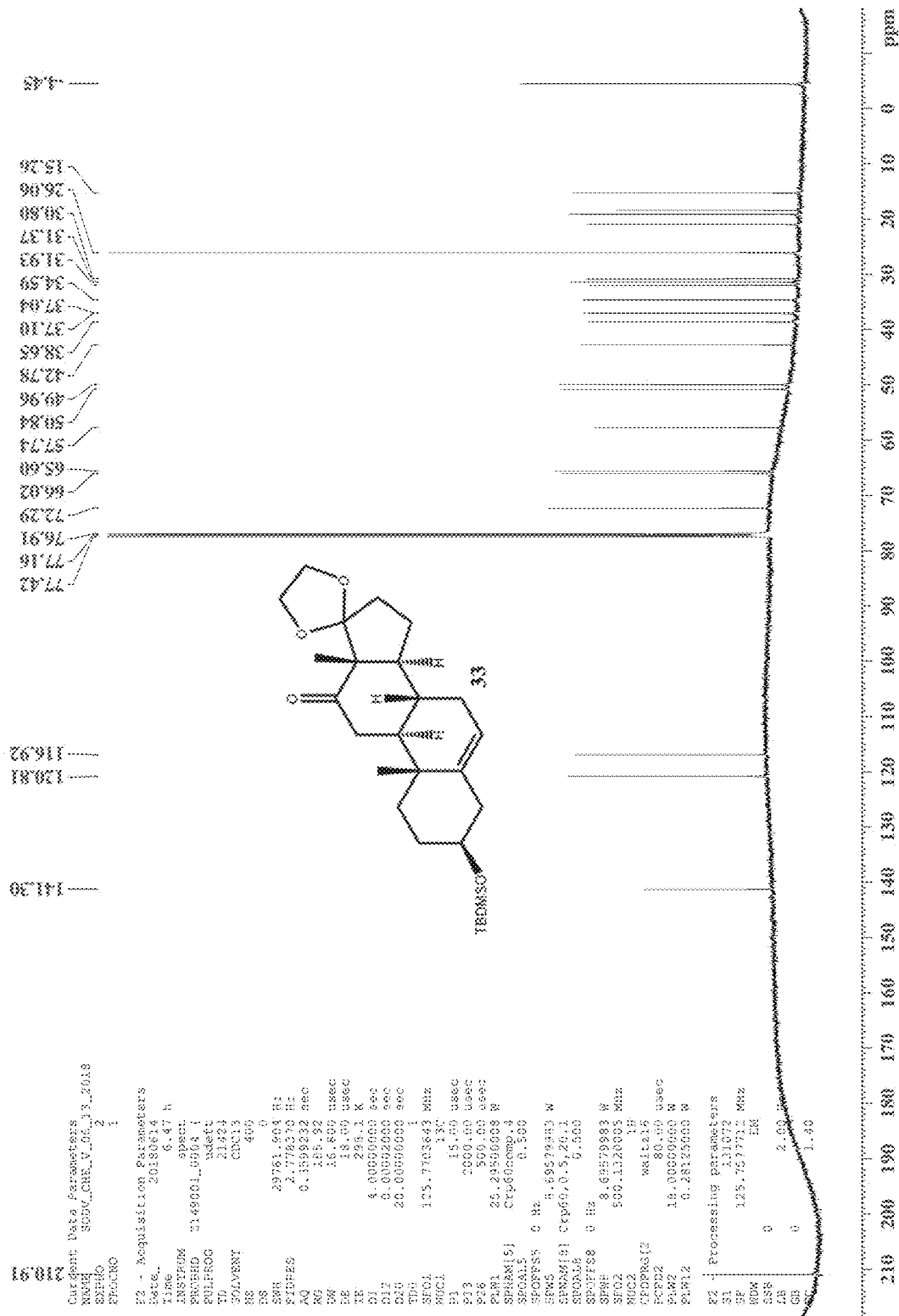
Figure 42:
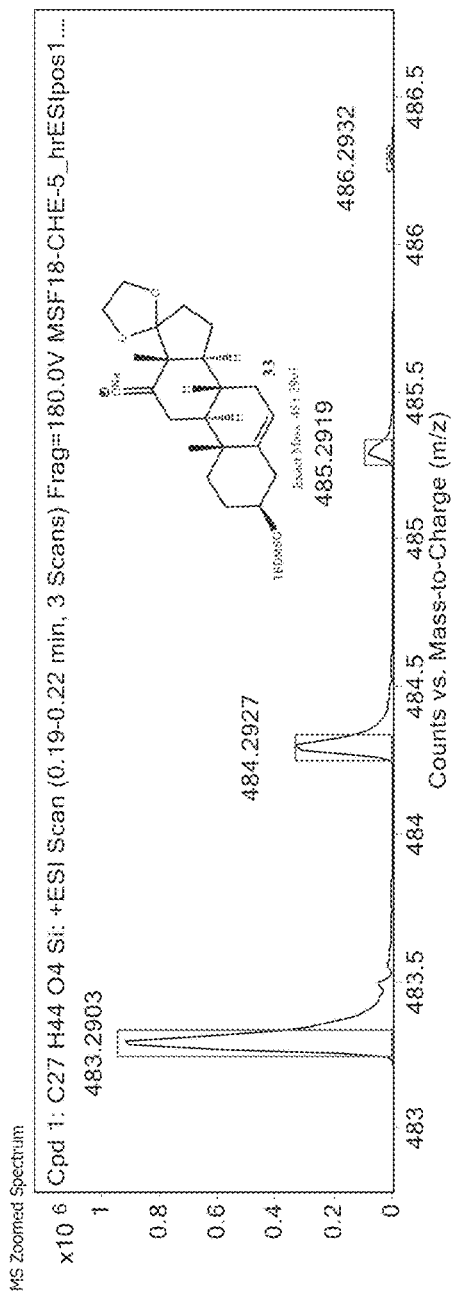
Figure 43:
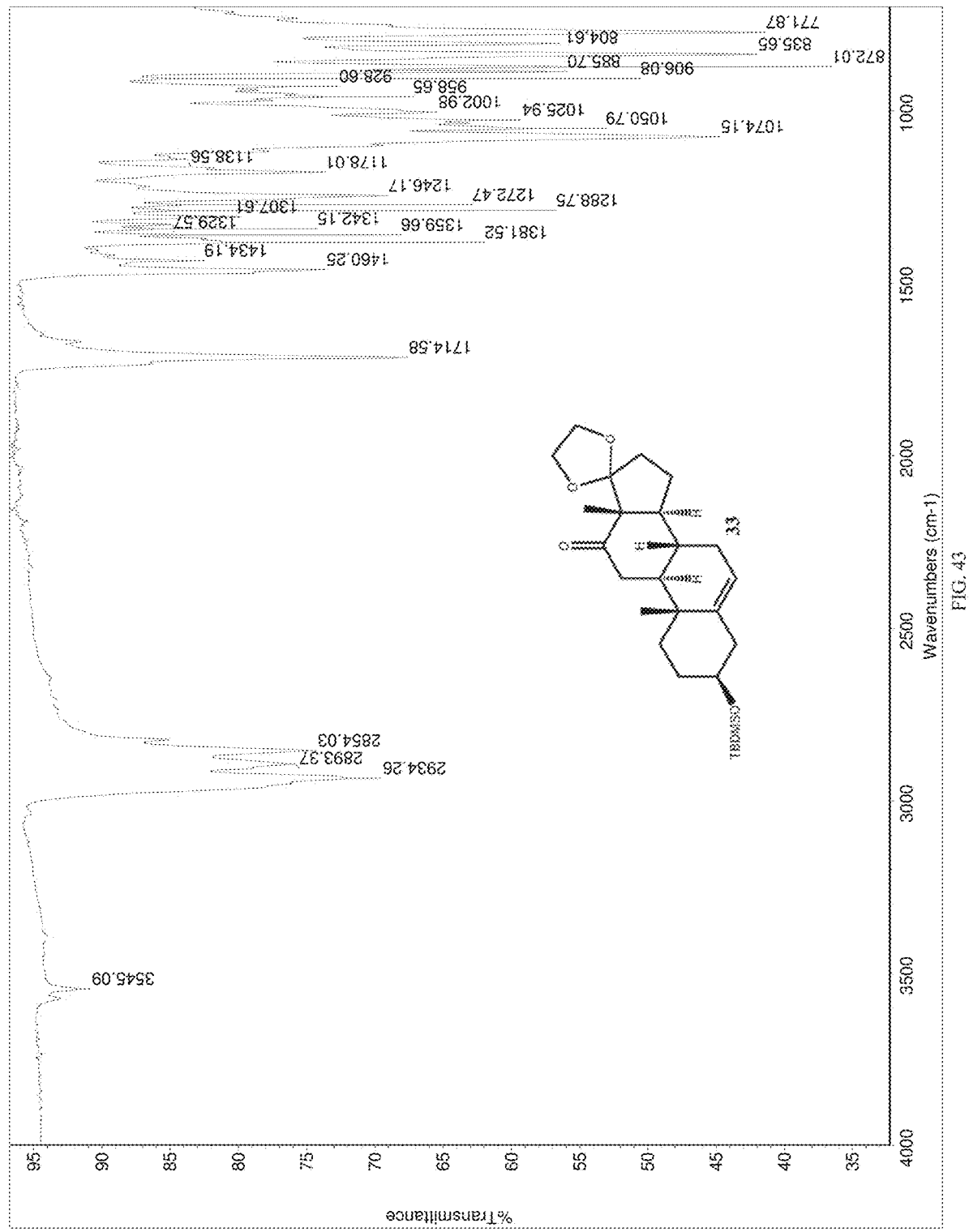
Figure 44:
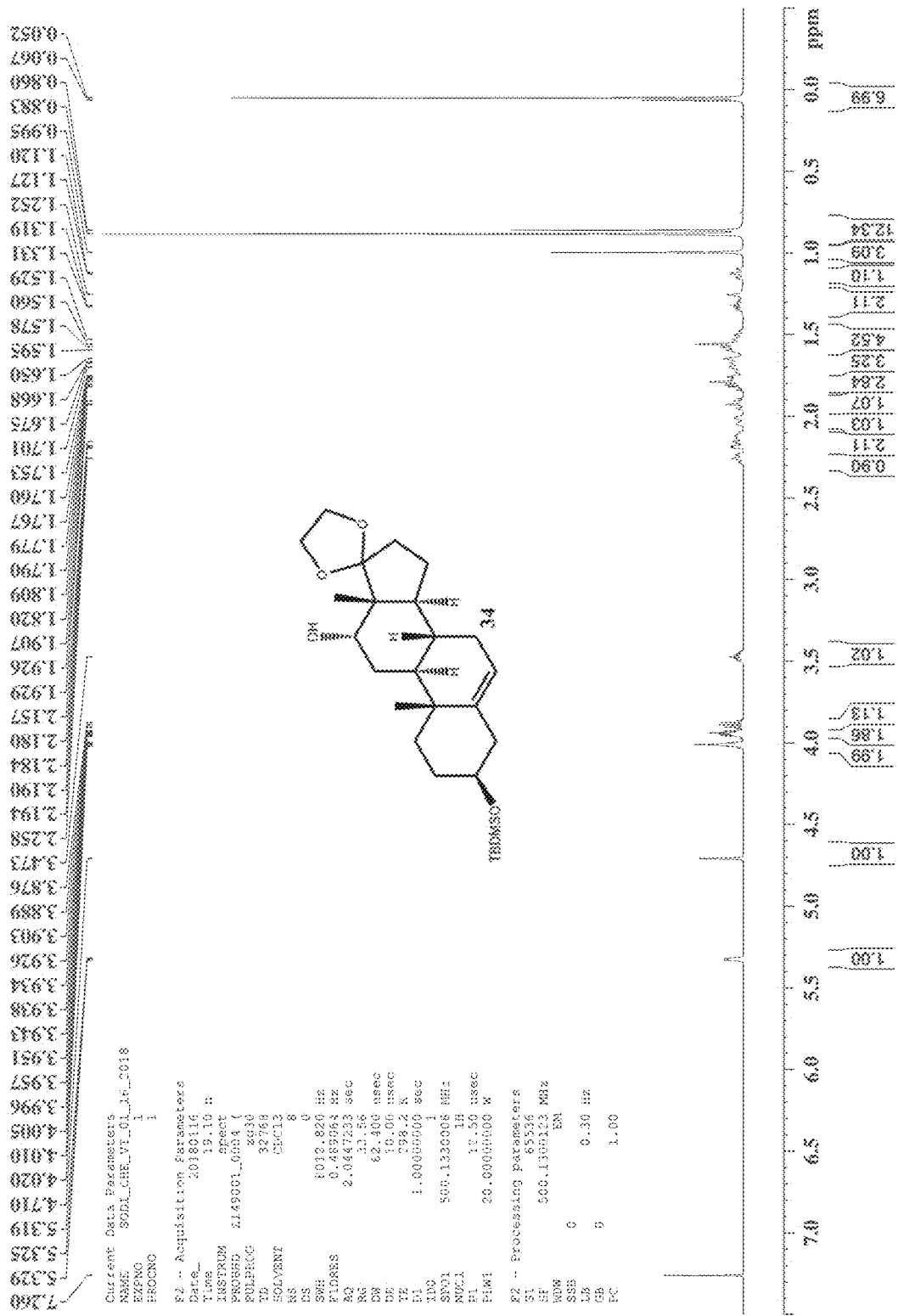
FIGS. 44-47 show $^1$H and $^{13}$C NMR, HRMS, and IR spectra of Compound 34.
Figure 45:
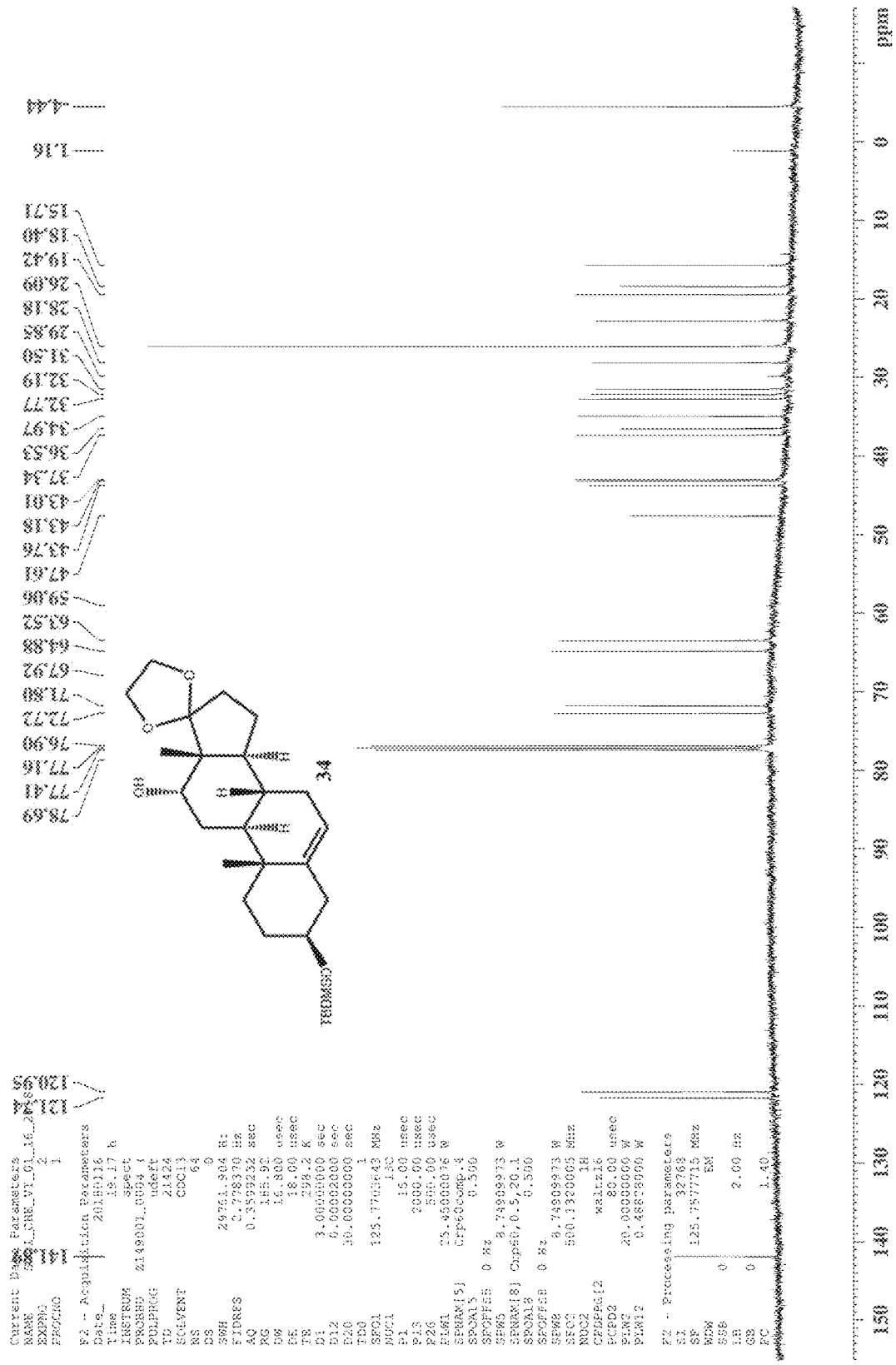
Figure 46:
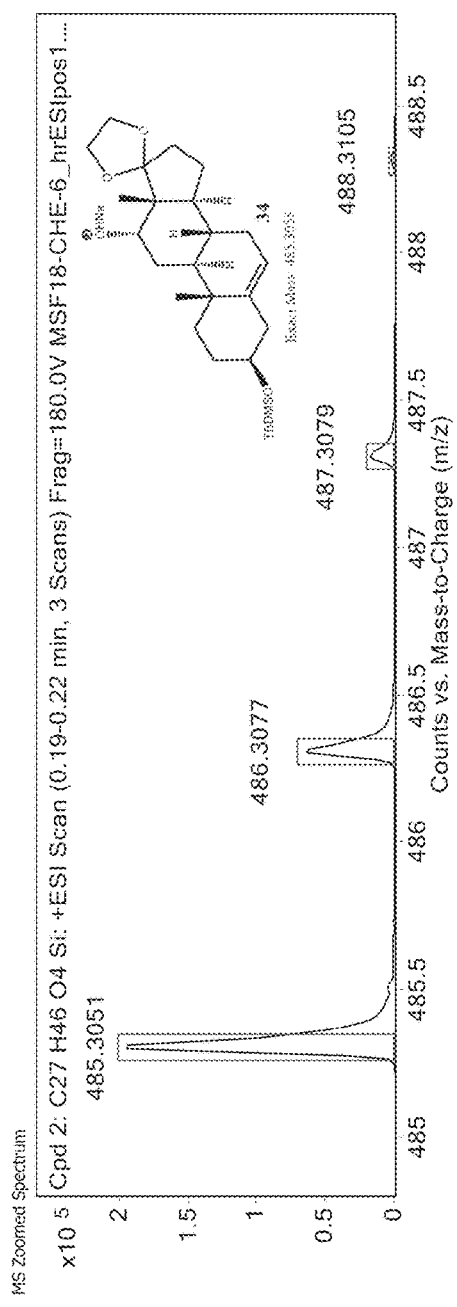
Figure 47:
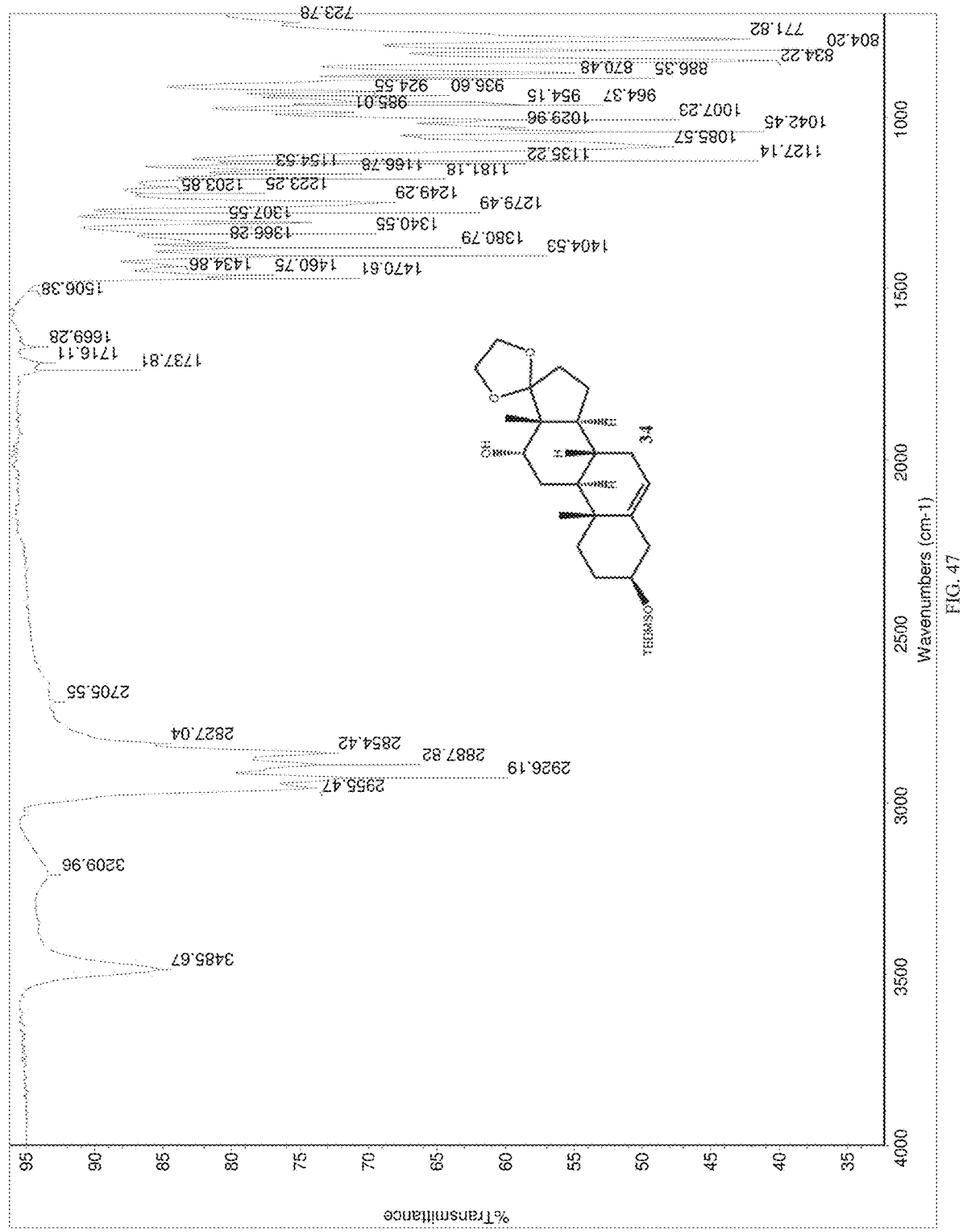
Figure 48:
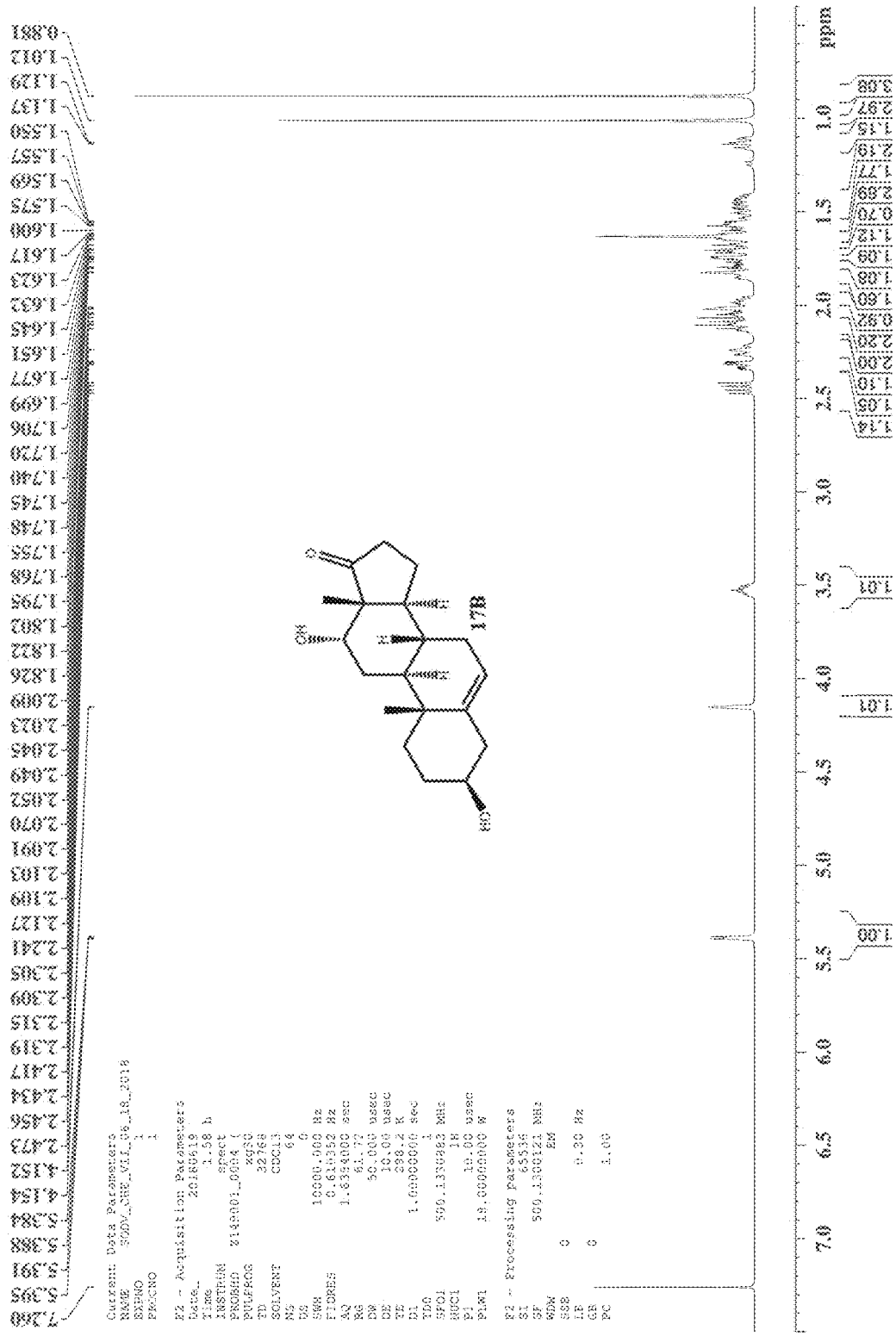
FIGS. 48-51 show $^1$H and $^{13}$C NMR, HRMS, and IR spectra of Compound 17B.
Figure 49:
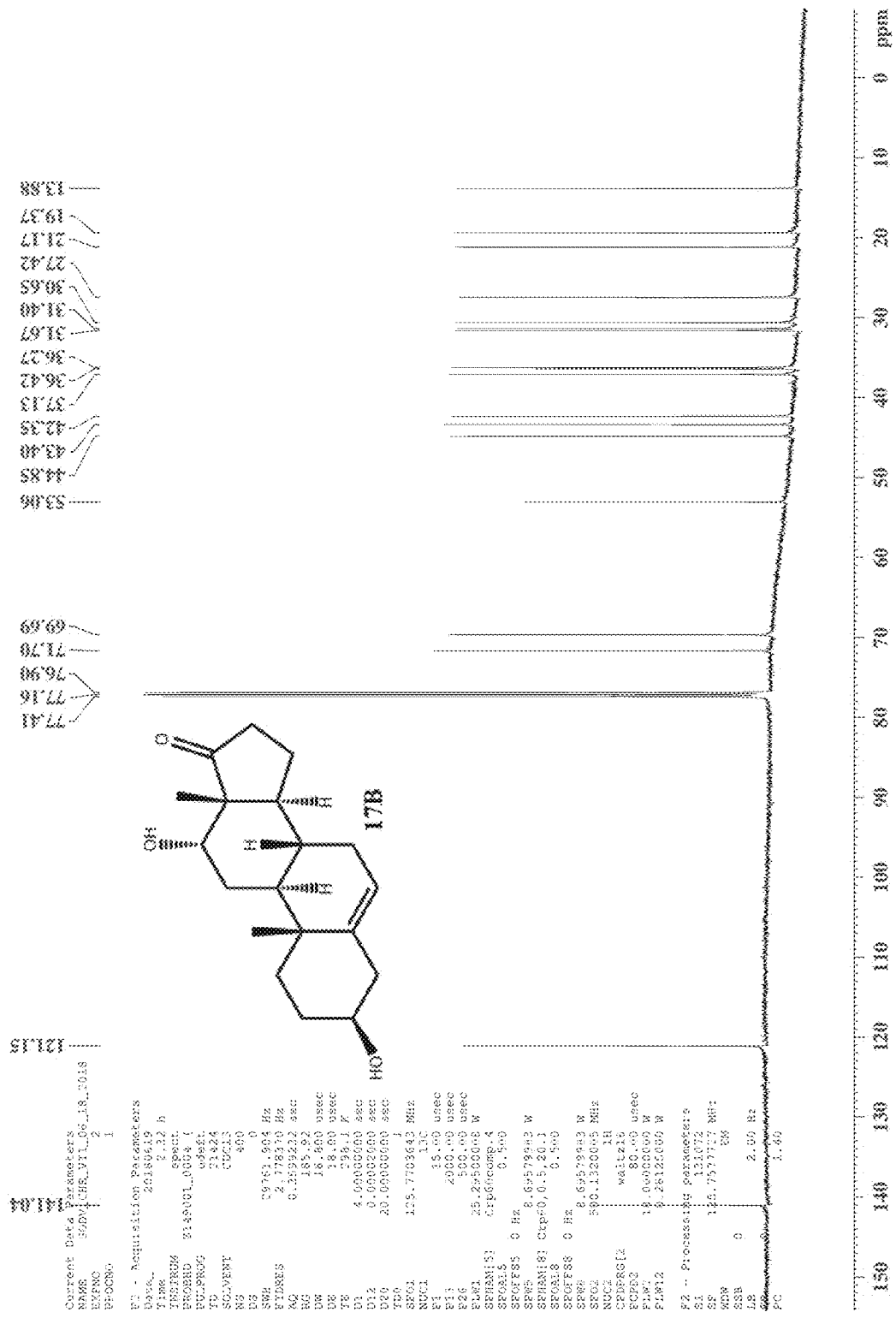
Figure 50:
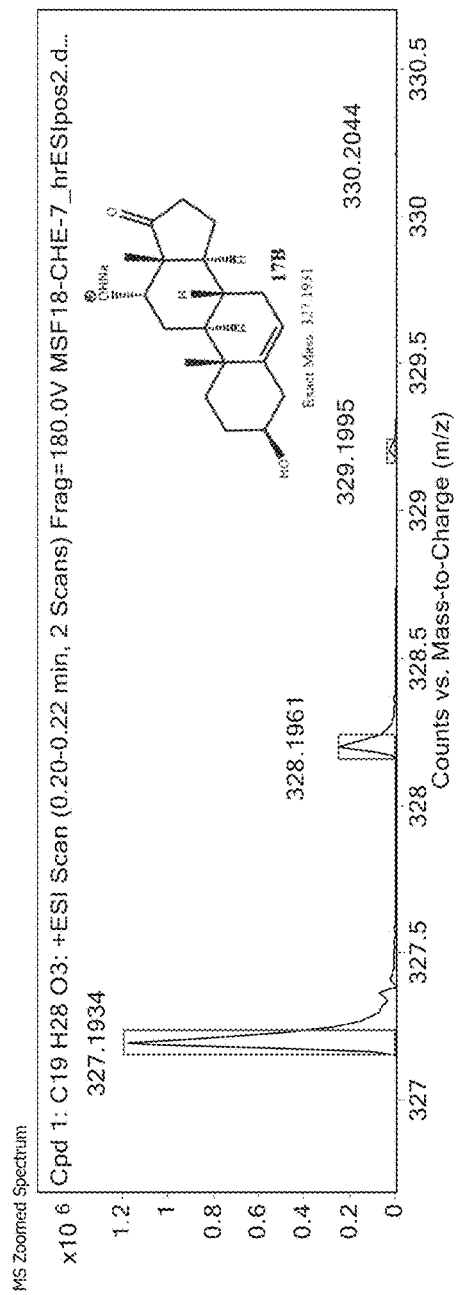
Figure 51:
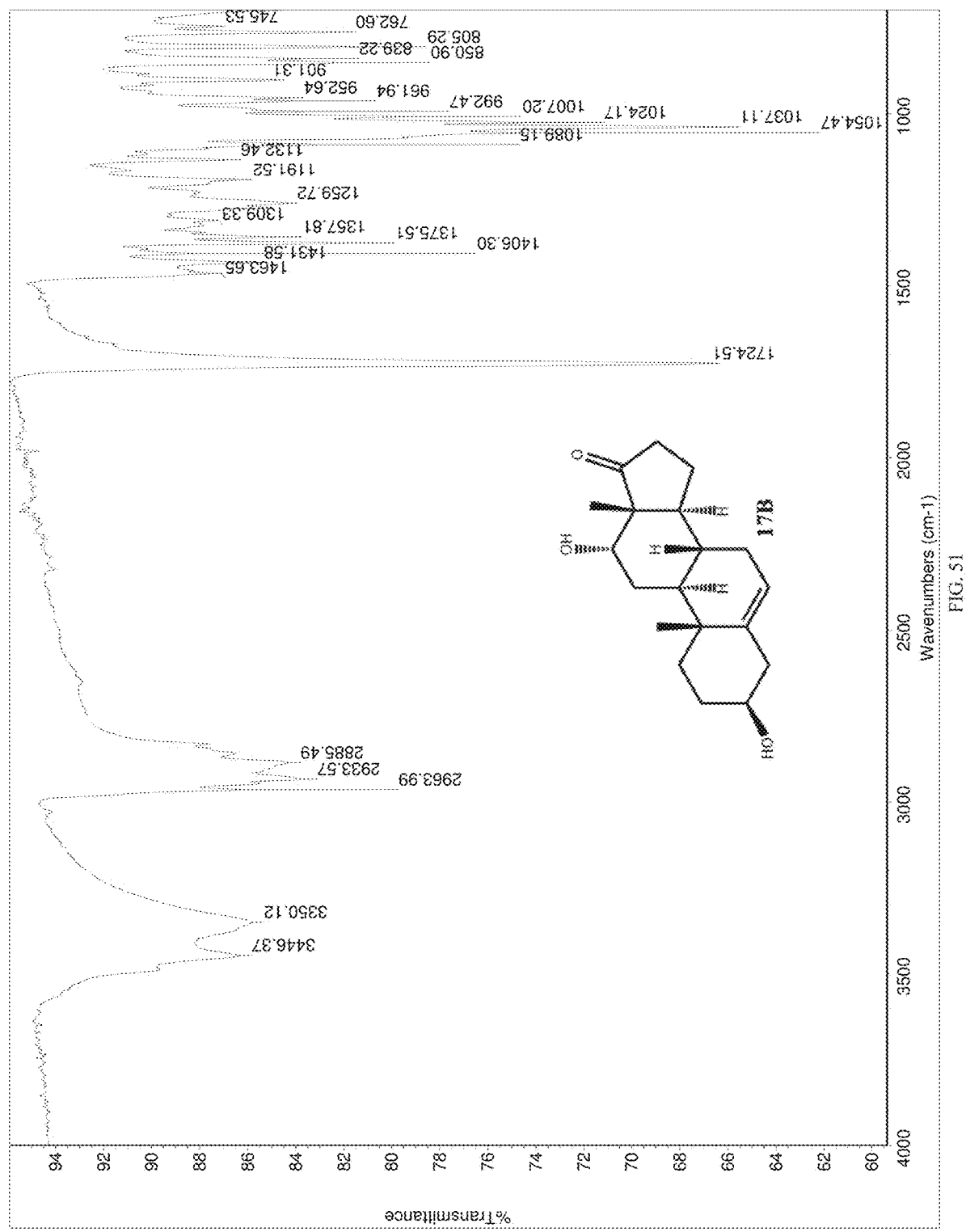
Figure 52:
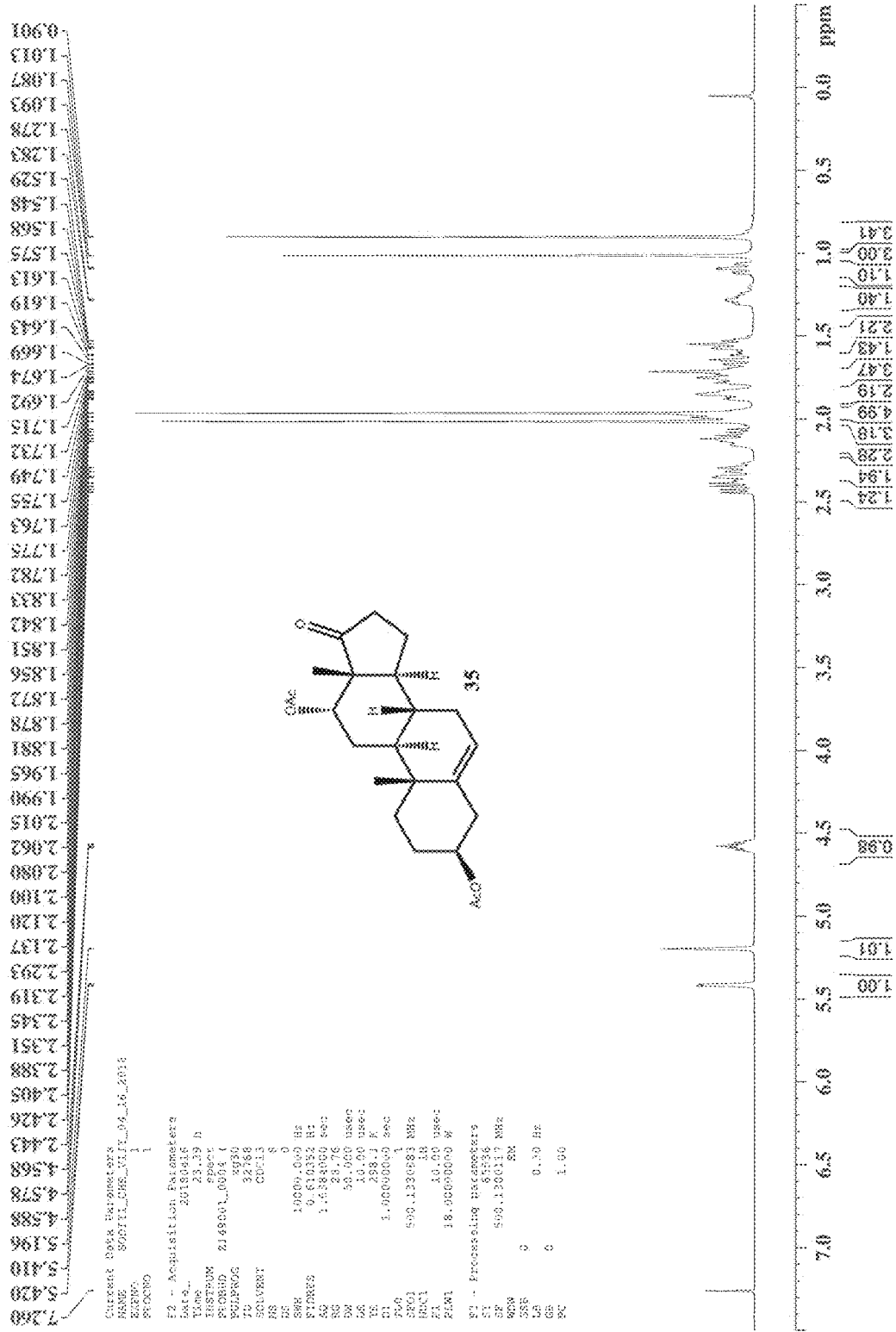
FIGS. 52-55 show $^1$H and $^{13}$C NMR, HRMS, and IR spectra of Compound 35.
Figure 53:
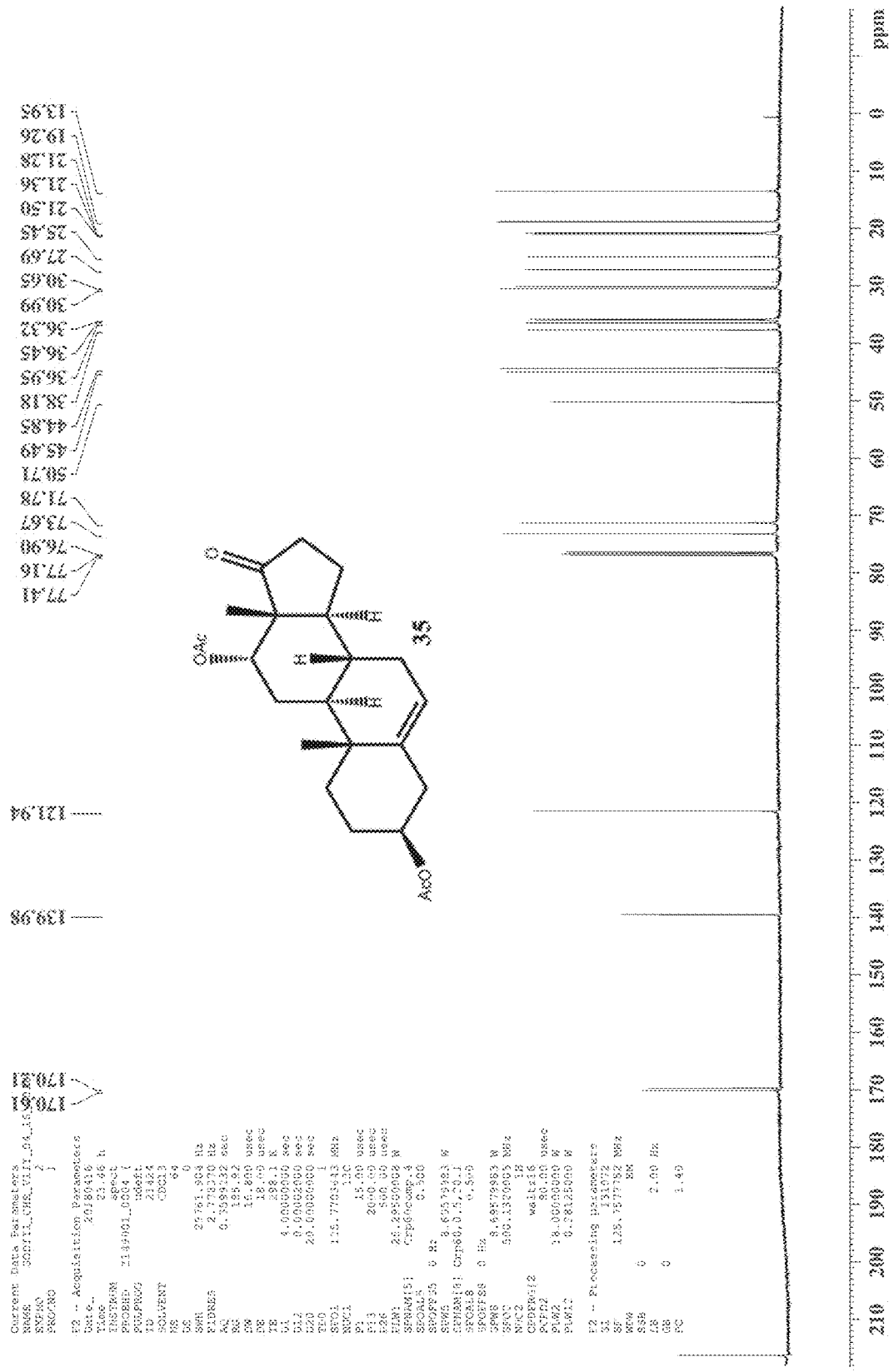
Figure 54:
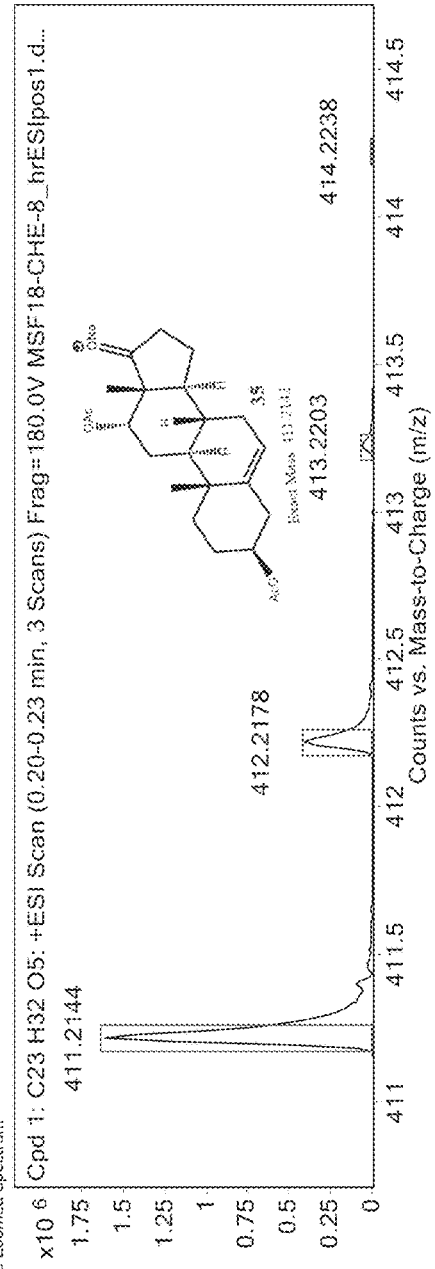
Figure 55:
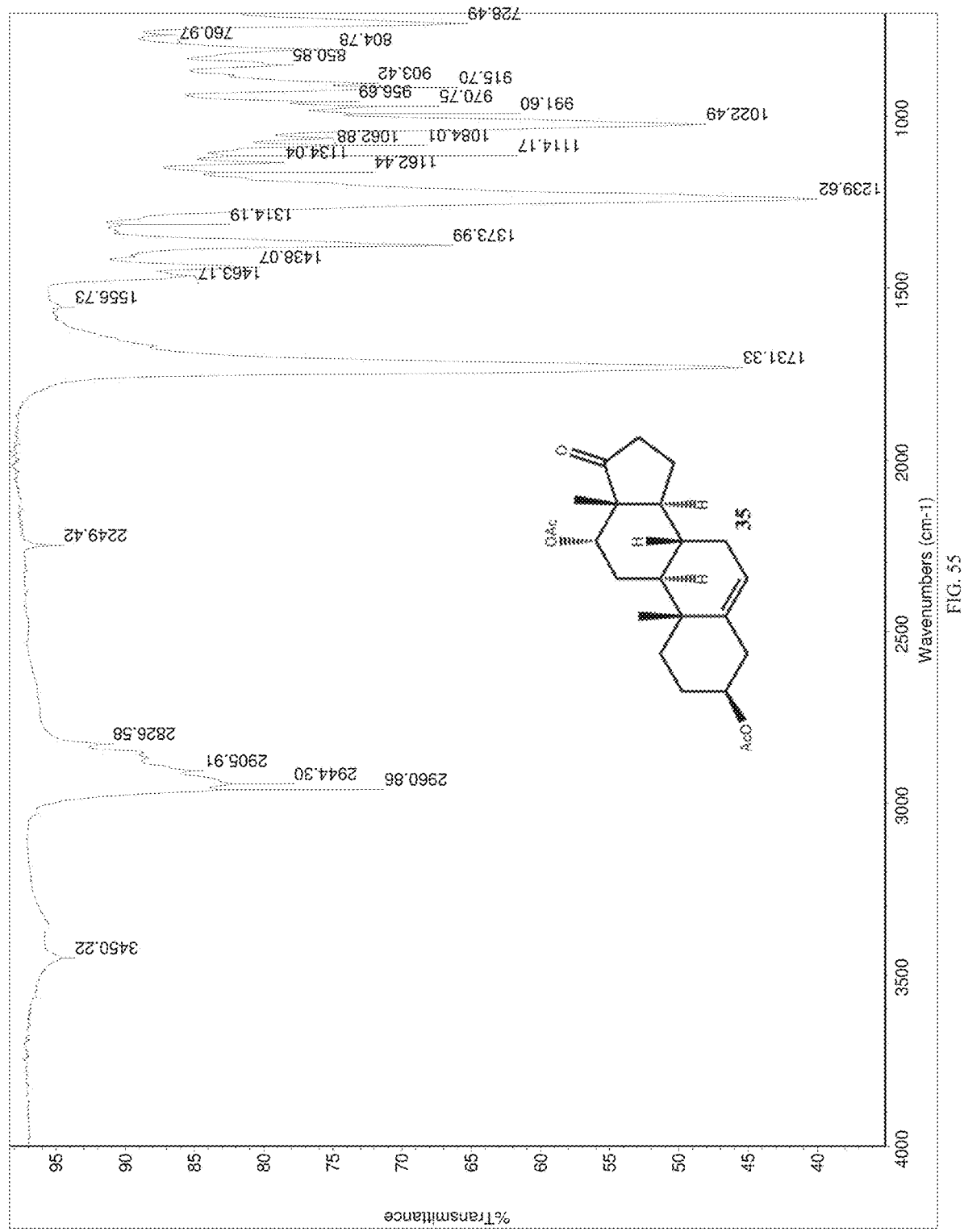
Figure 56:
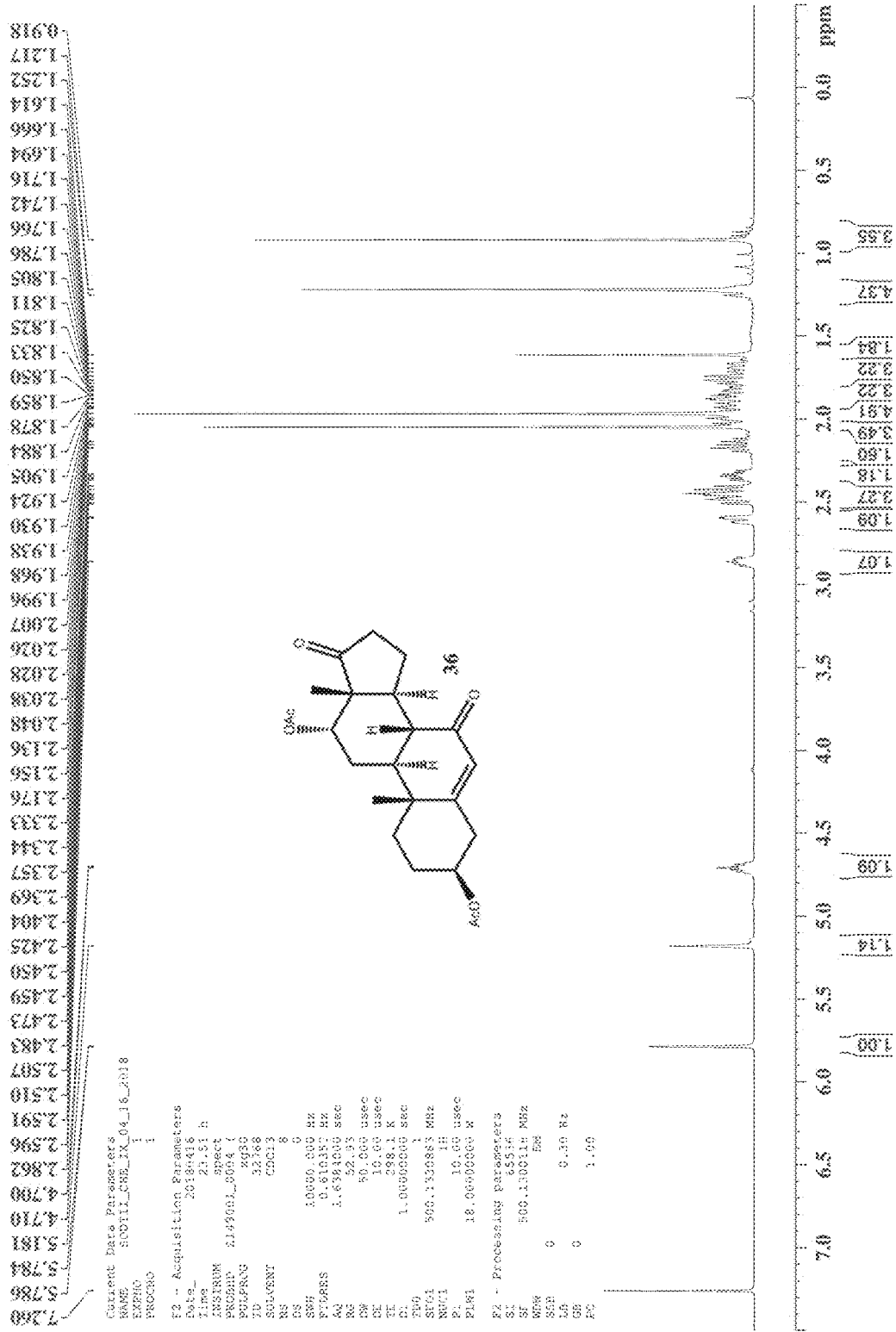
FIGS. 56-59 show $^1$H and $^{13}$C NMR, HRMS, and IR spectra of Compound 36.
Figure 57:
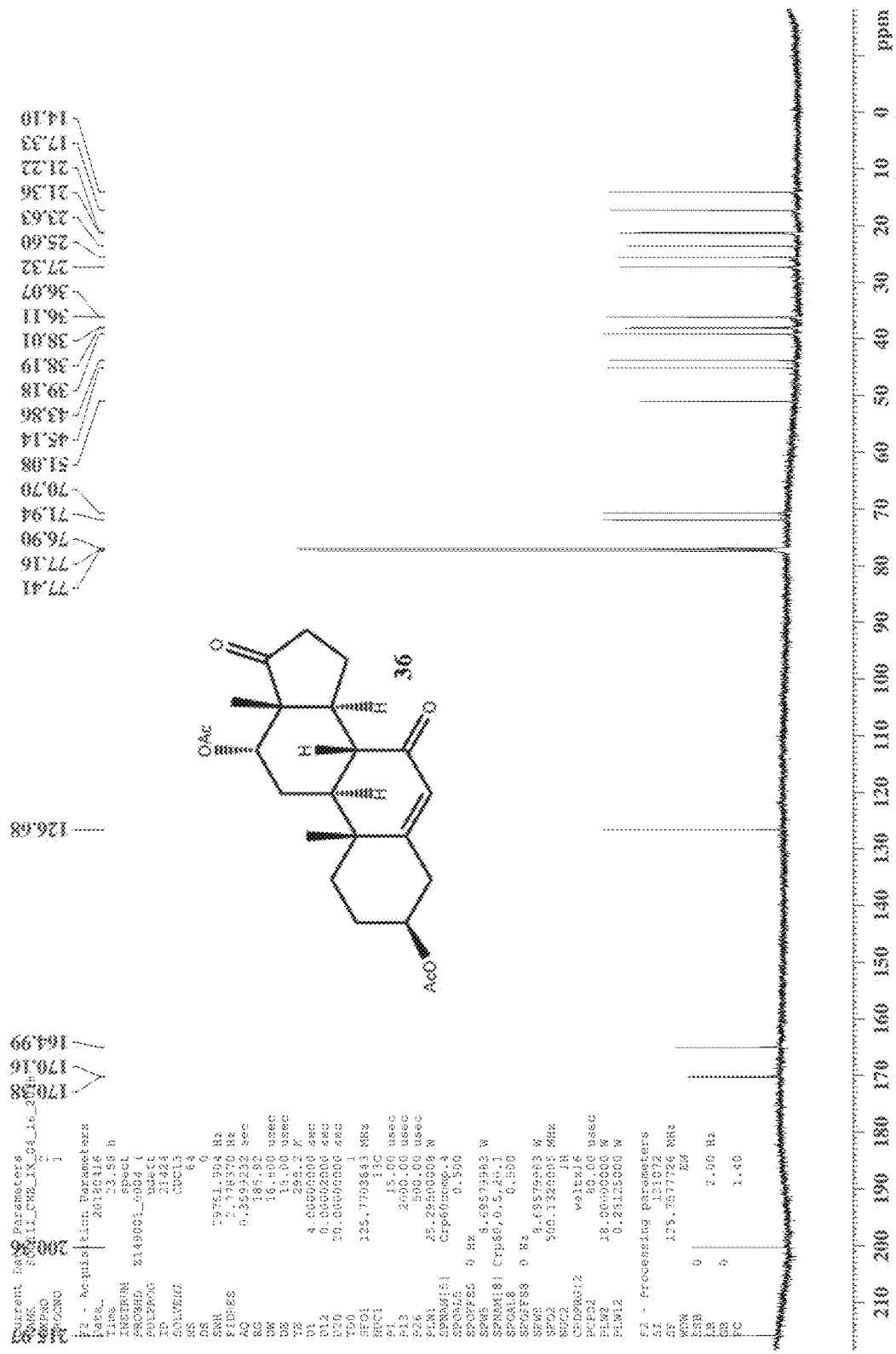
Figure 58:
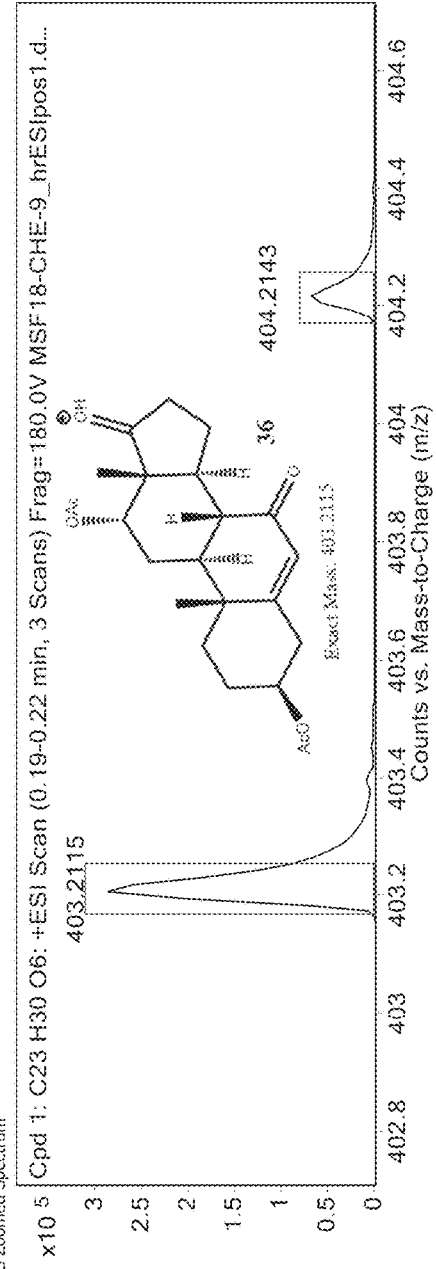
Figure 59:
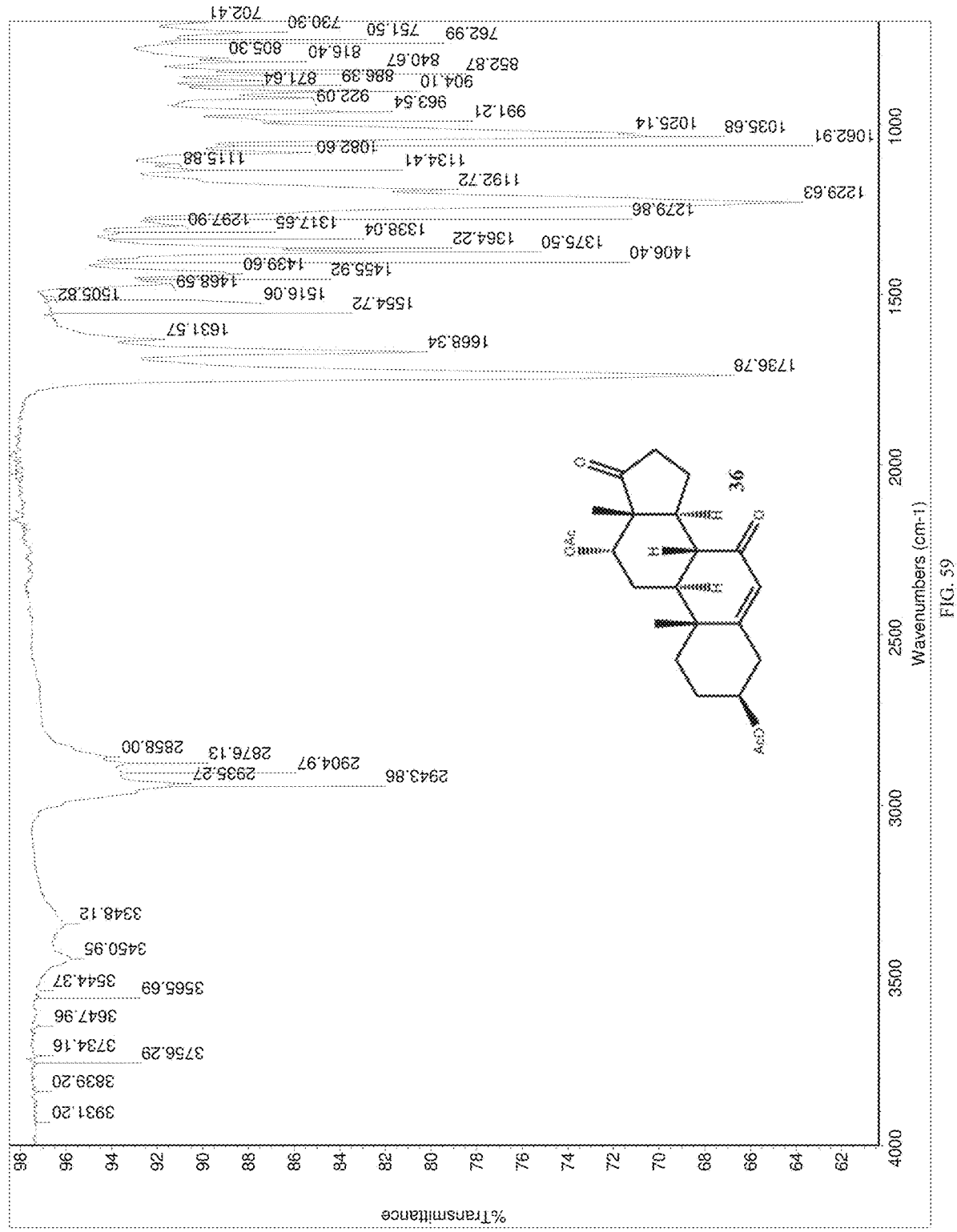
Figure 60:
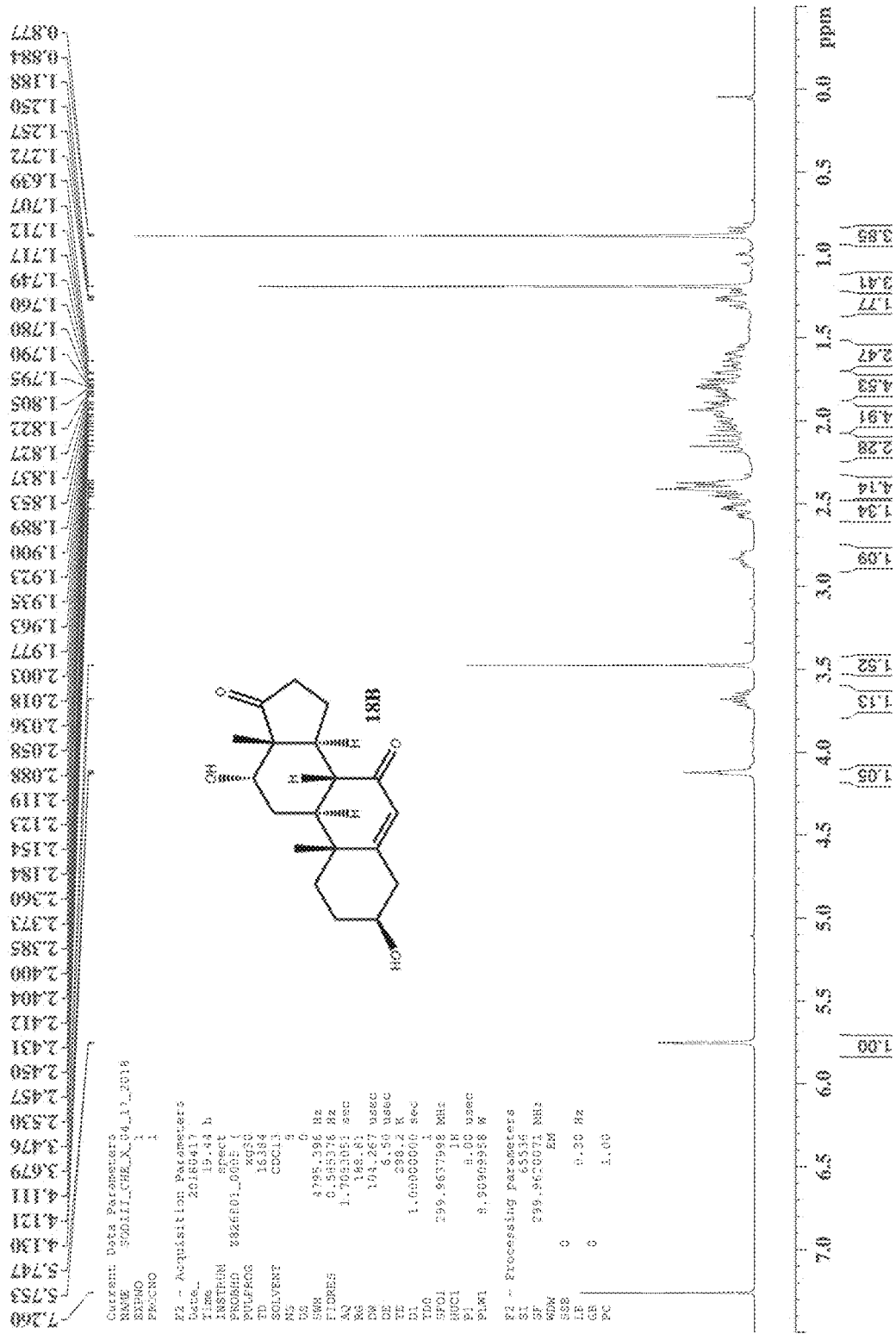
FIGS. 60-63 show $^1$H NMR, HRMS, and IR spectra of Compound 18B.
Figure 61:
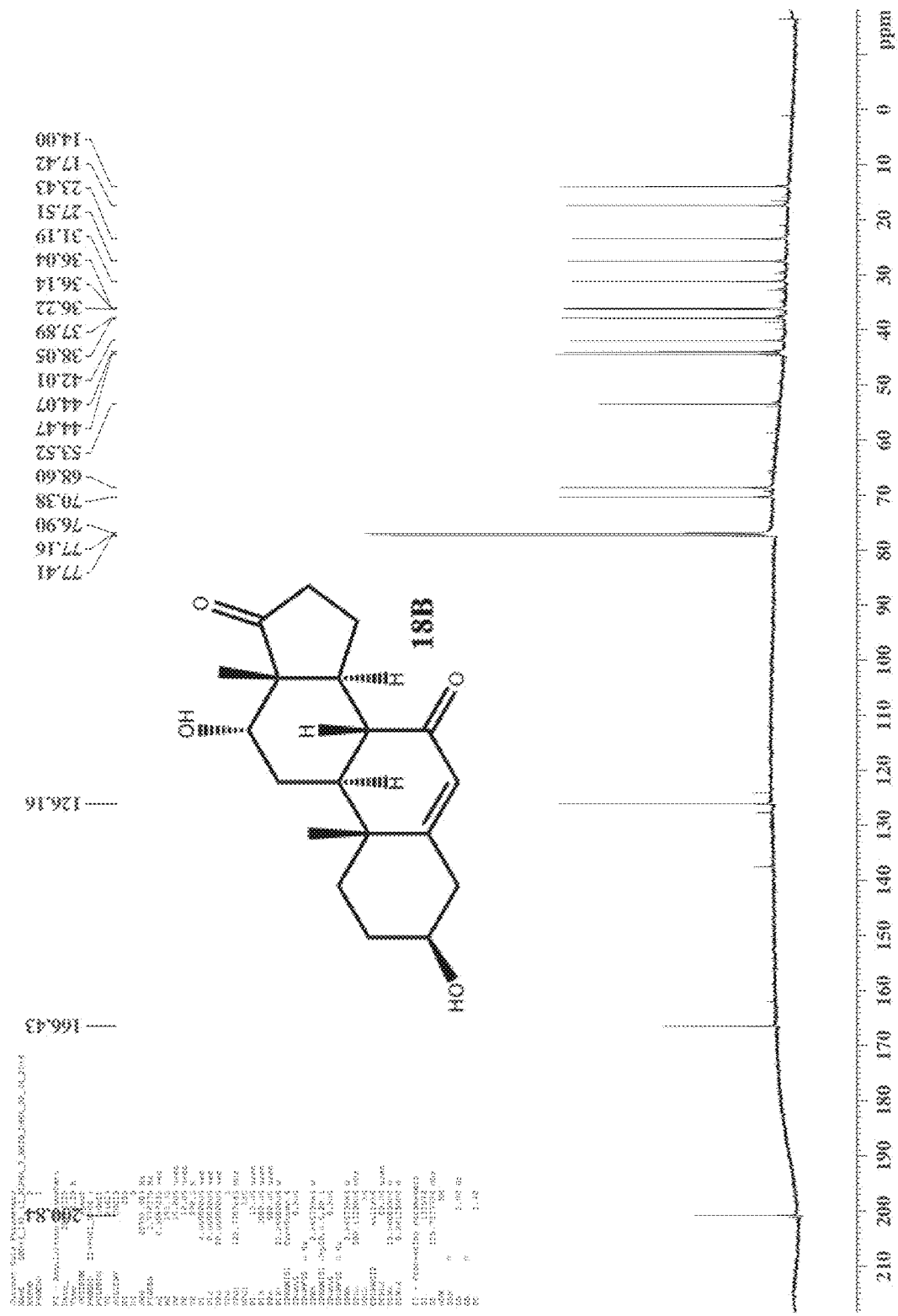
Figure 62:
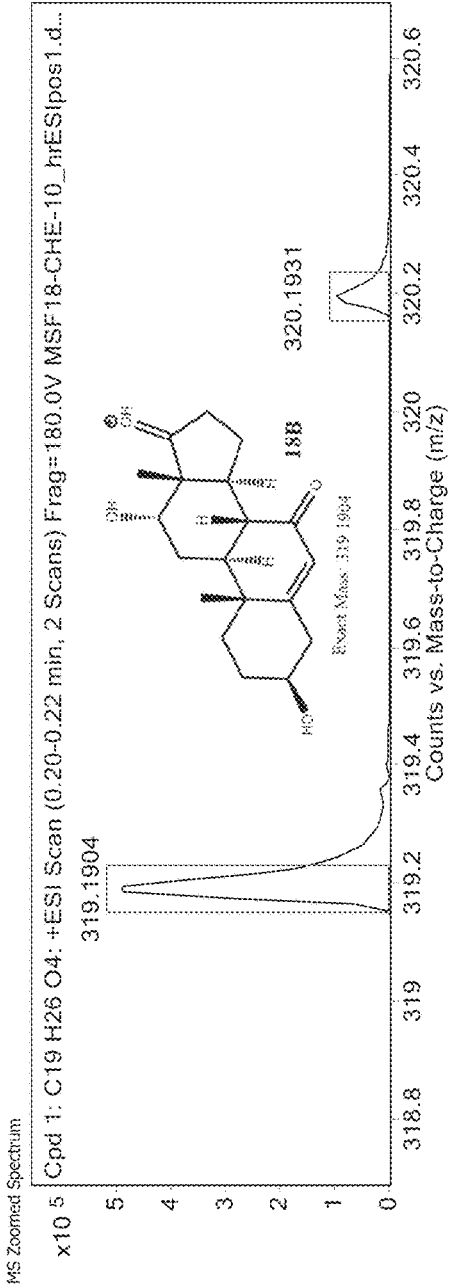
Figure 63:
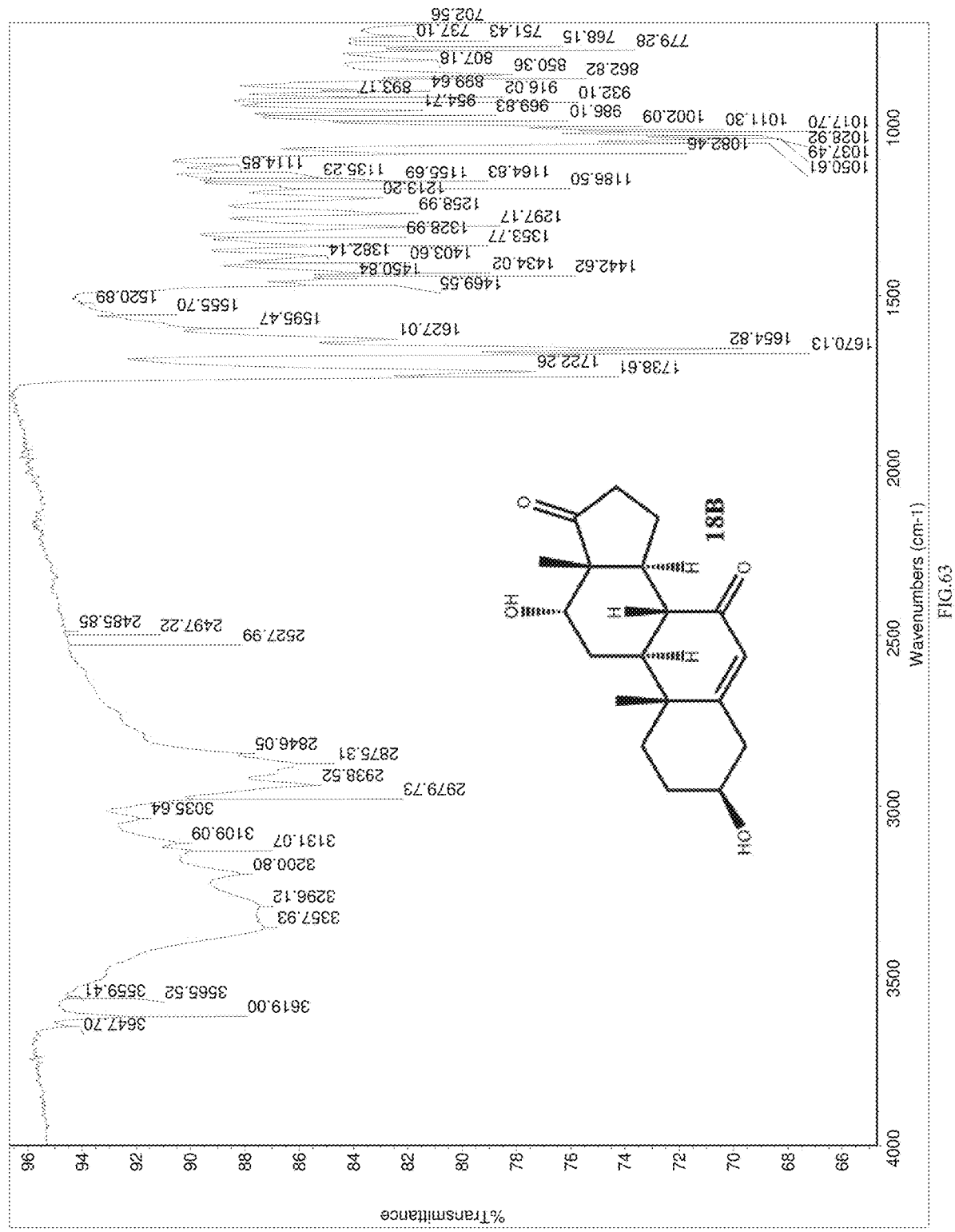
Figure 64:
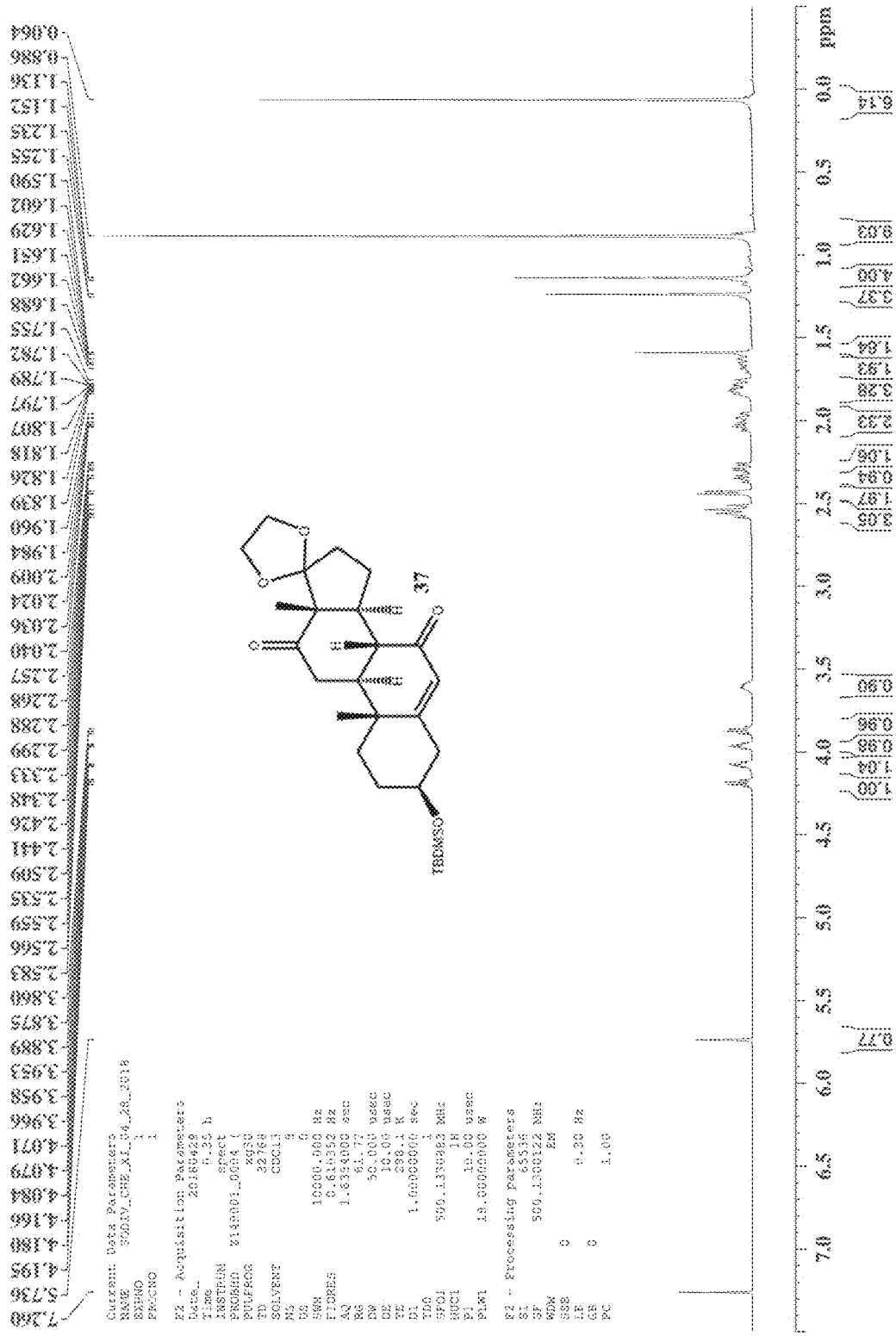
FIGS. 64-67 show $^1$H and $^{13}$C NMR, HRMS, and IR spectra of Compound 37.
Figure 65:
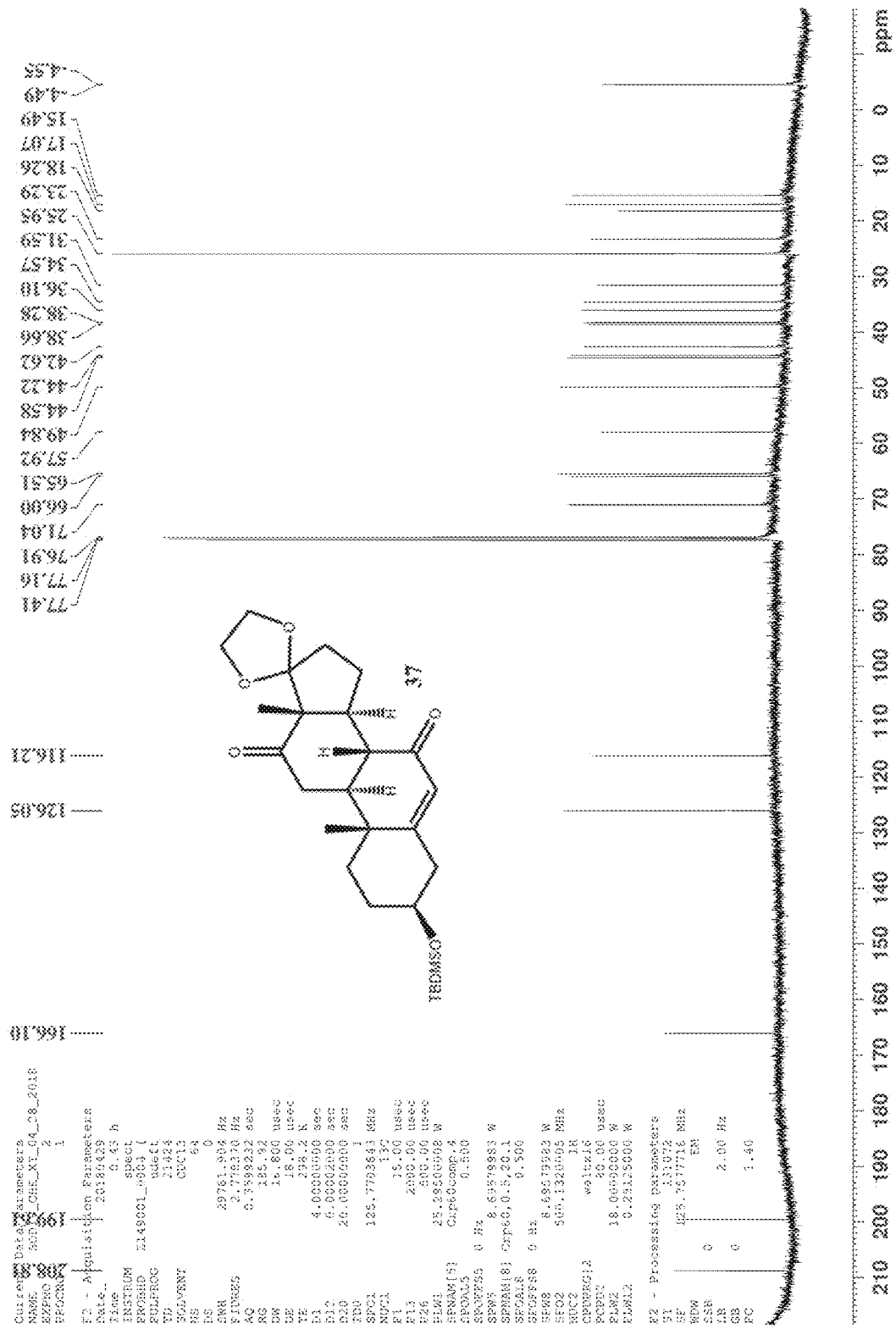
Figure 66:
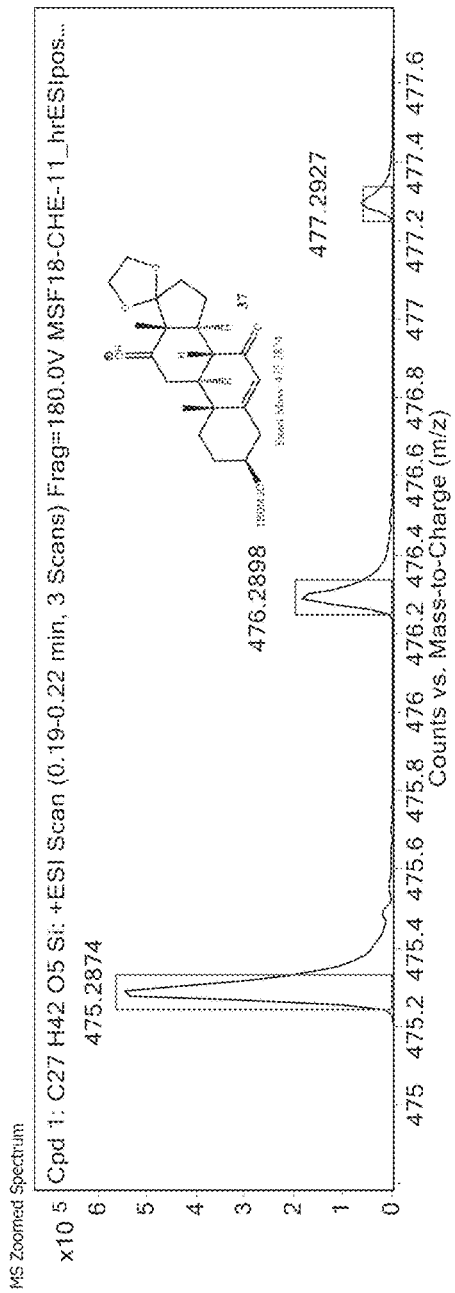
Figure 67:
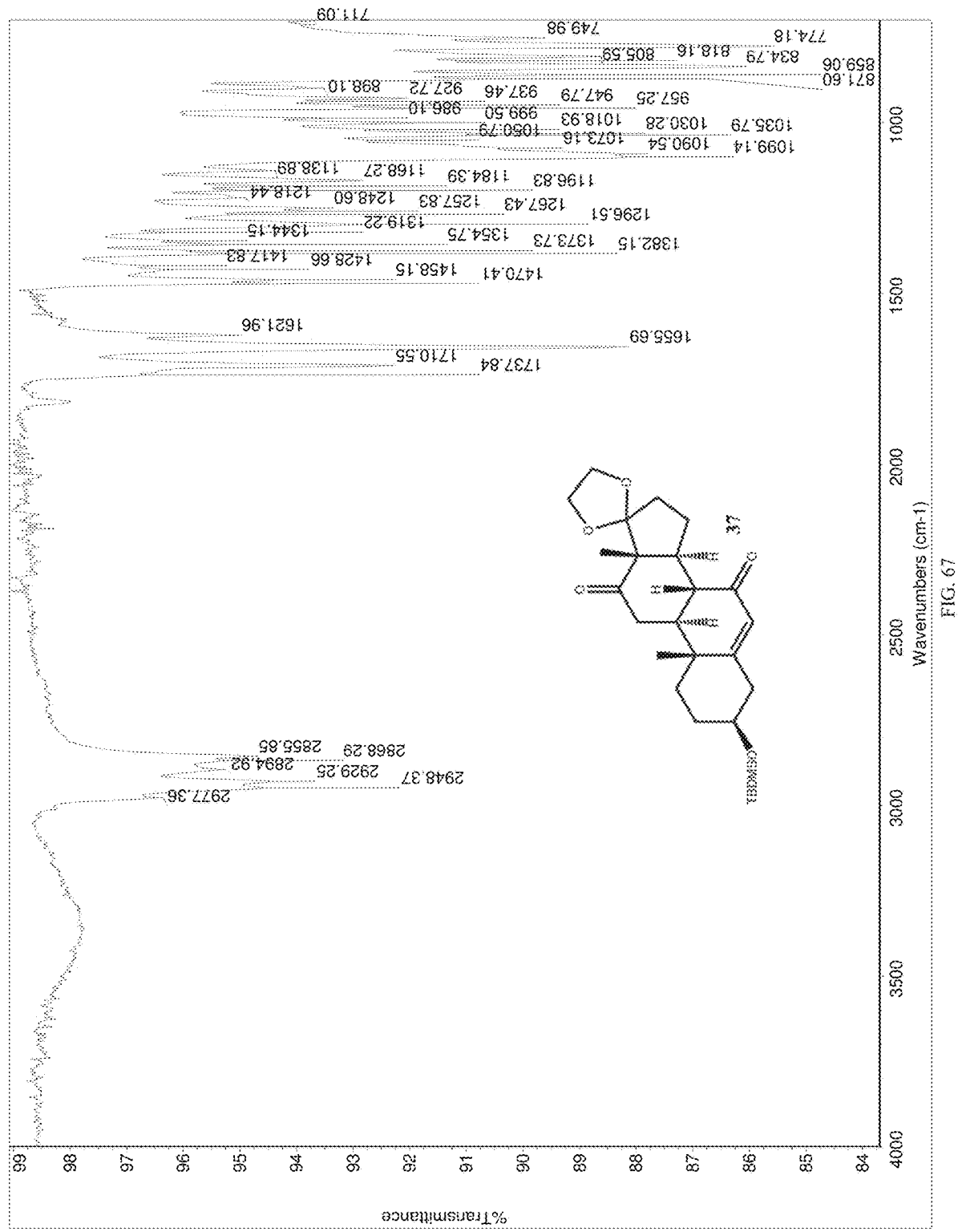
Figure 68:
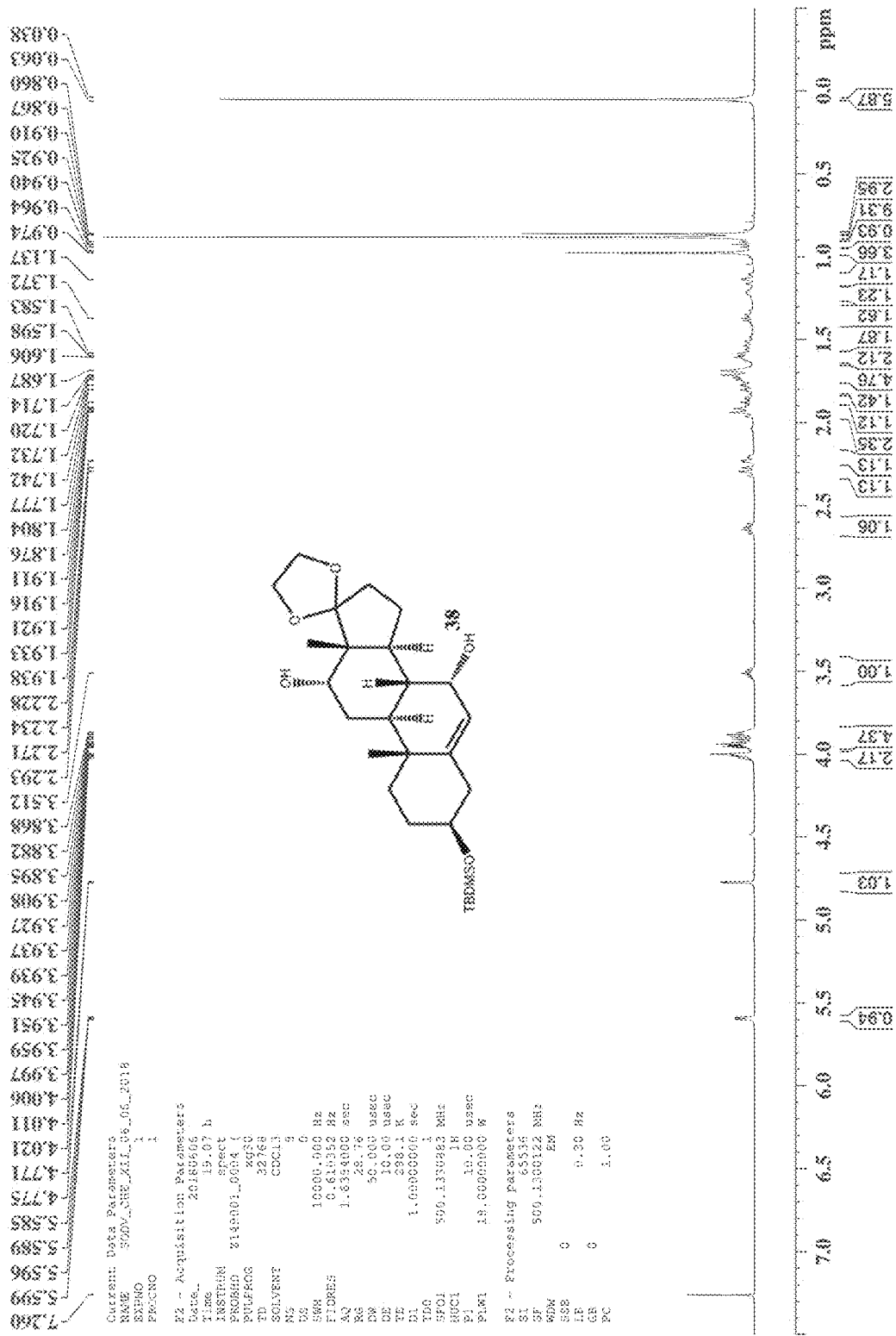
FIGS. 68-71 show $^1$H and $^{13}$C NMR, HRMS, and IR spectra of Compound 38.
Figure 69:
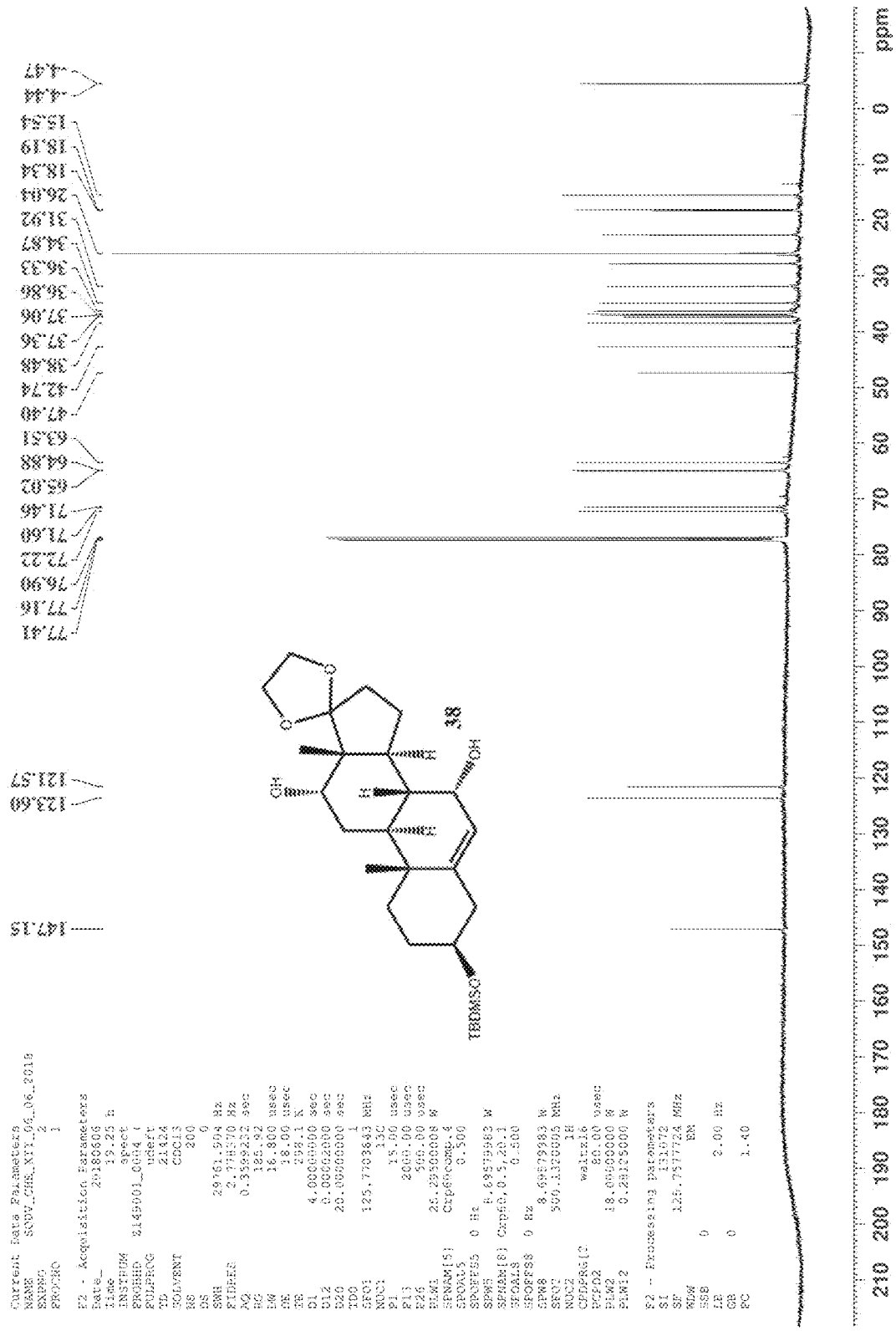
Figure 70:
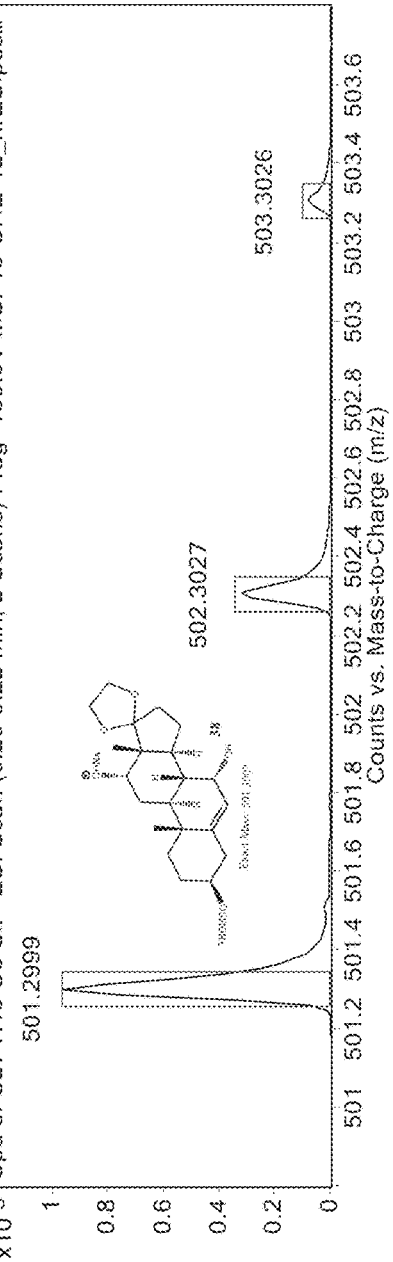
Figure 71:
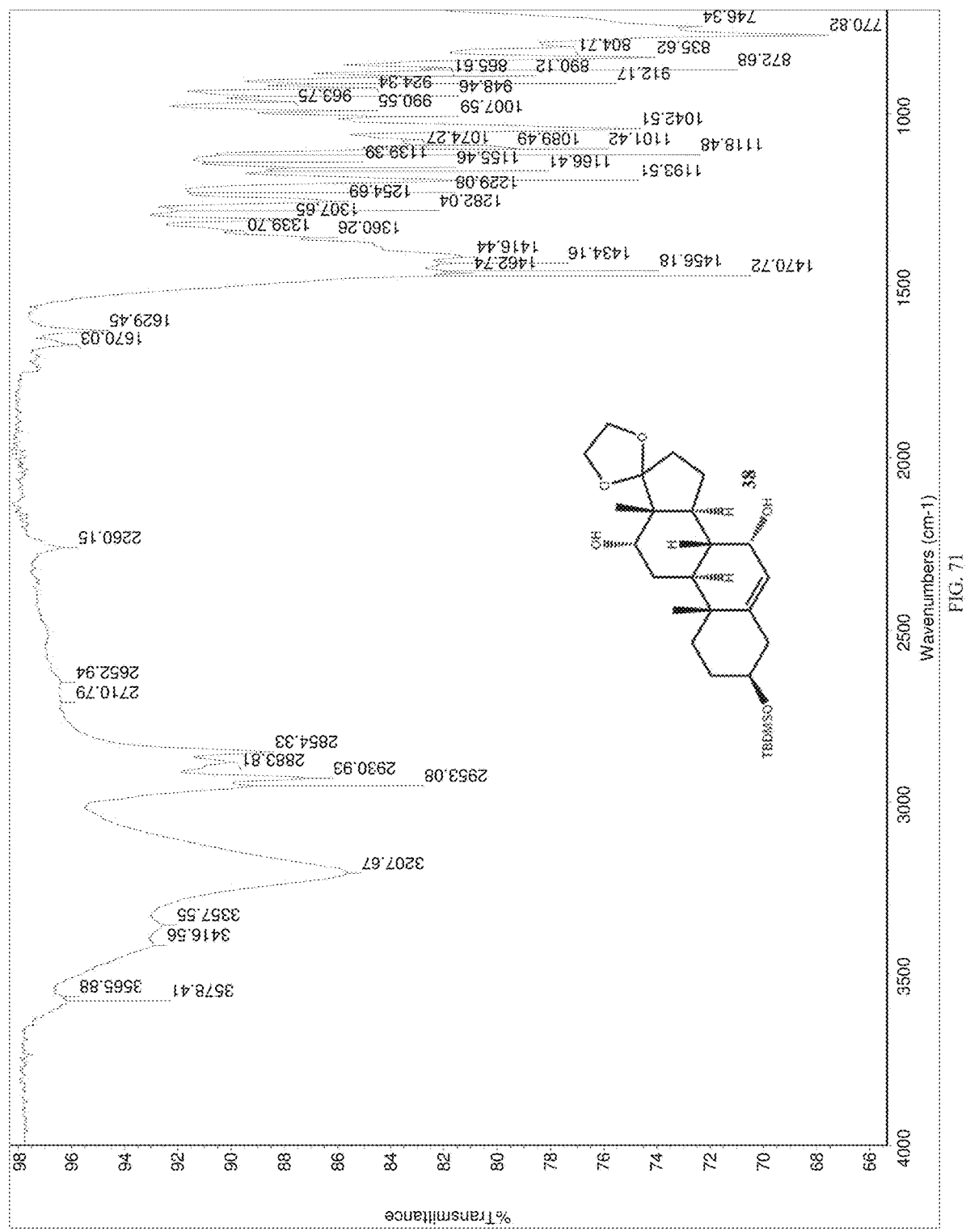
Figure 72:
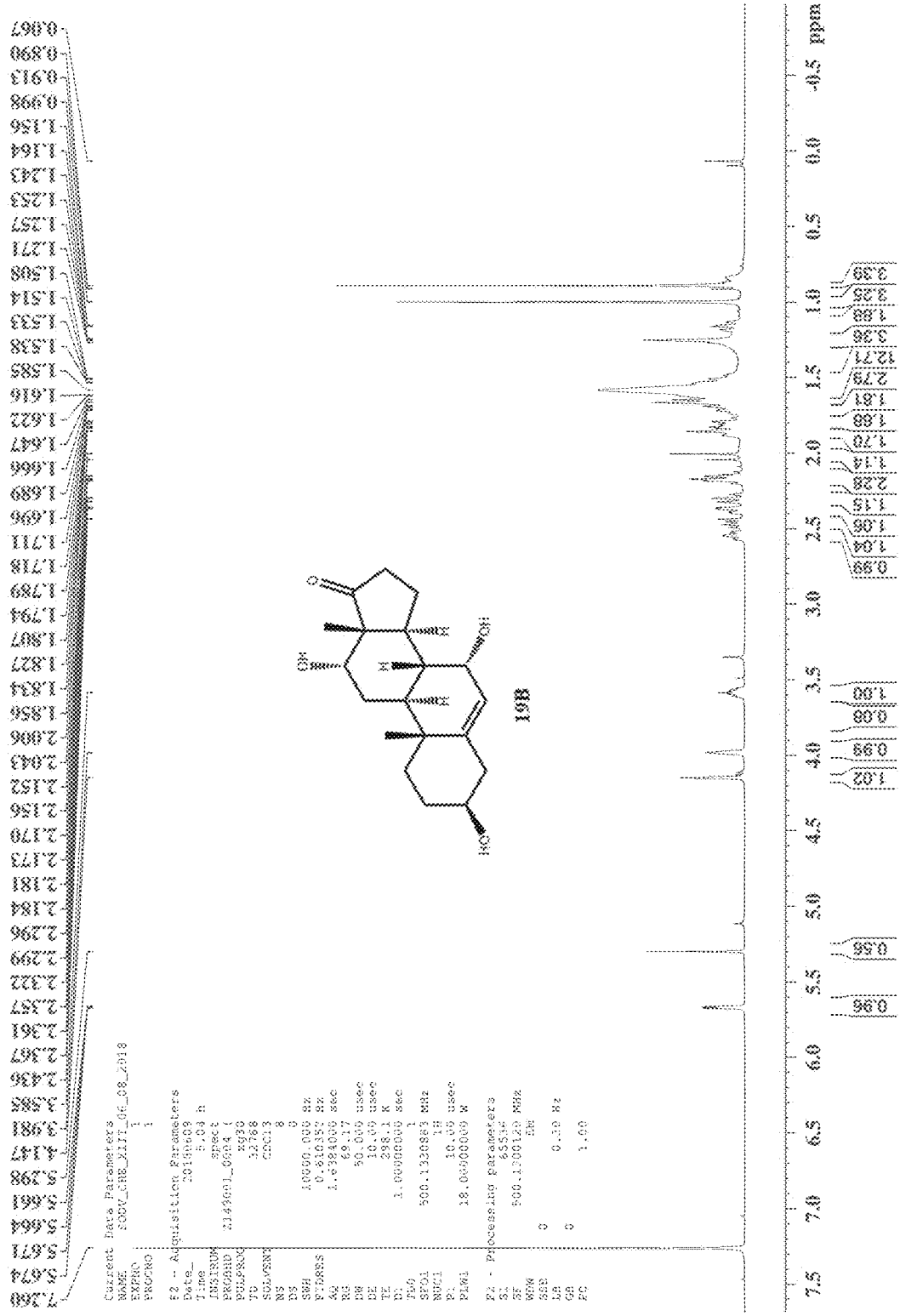
FIGS. 72-75 show $^1$H and $^{13}$C NMR, HRMS, and IR spectra of Compound 19B.
Figure 73:
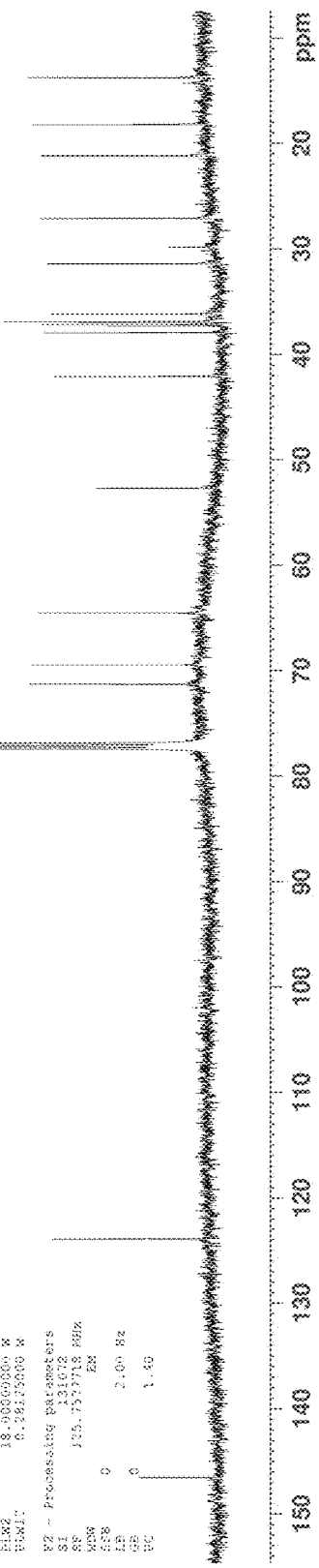
Figure 74:
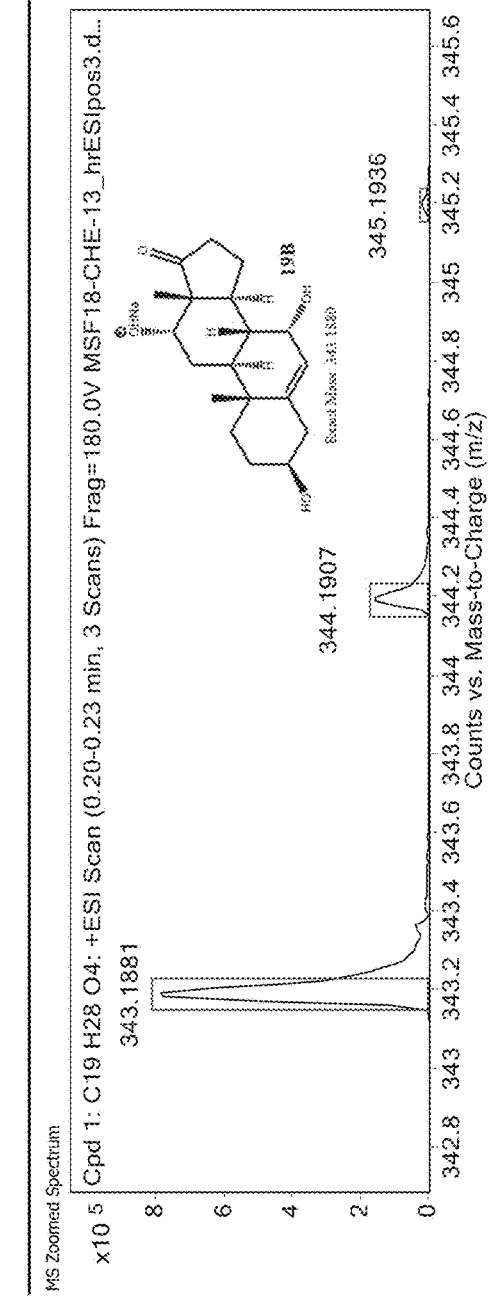
Figure 75:
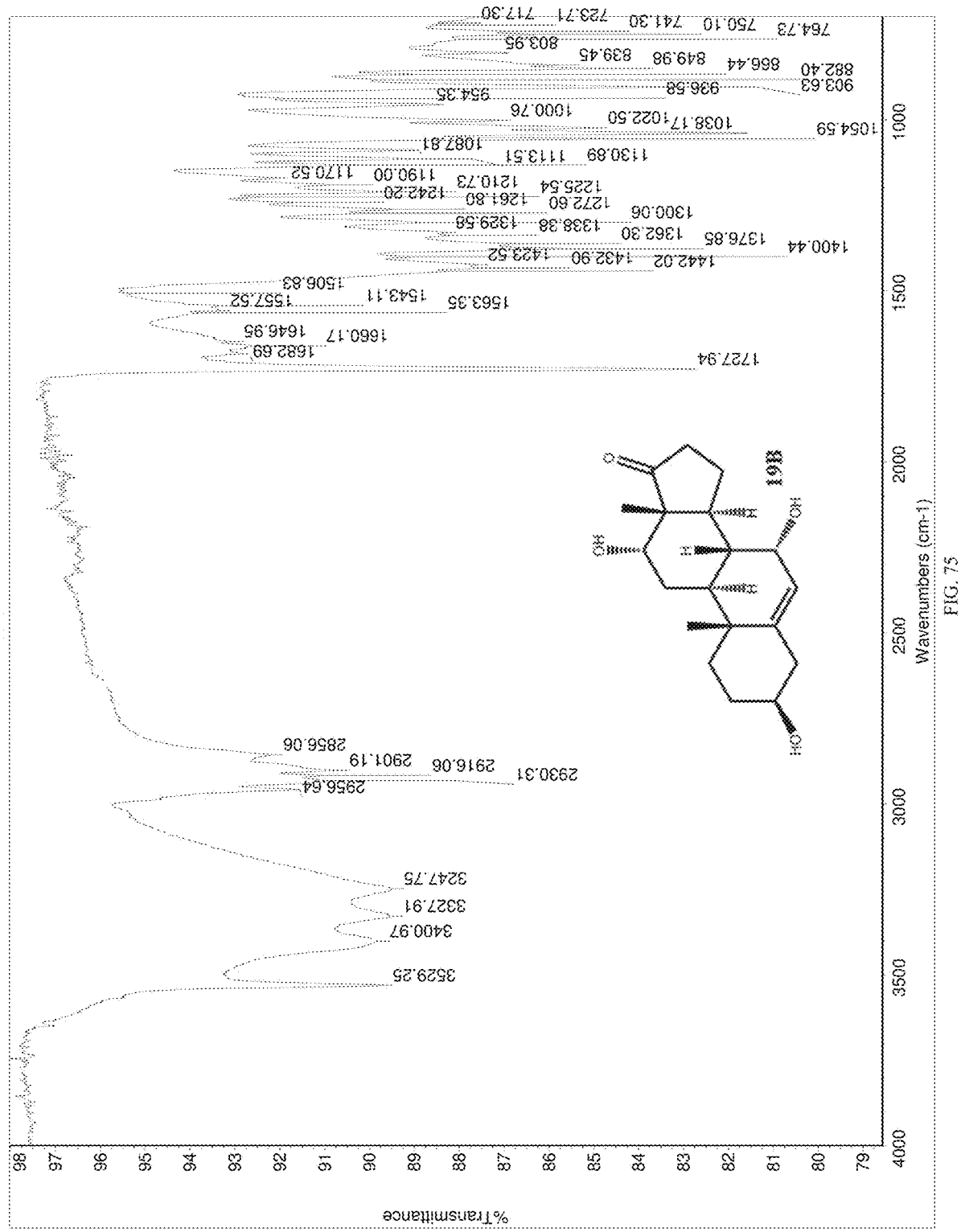
Figure 76:
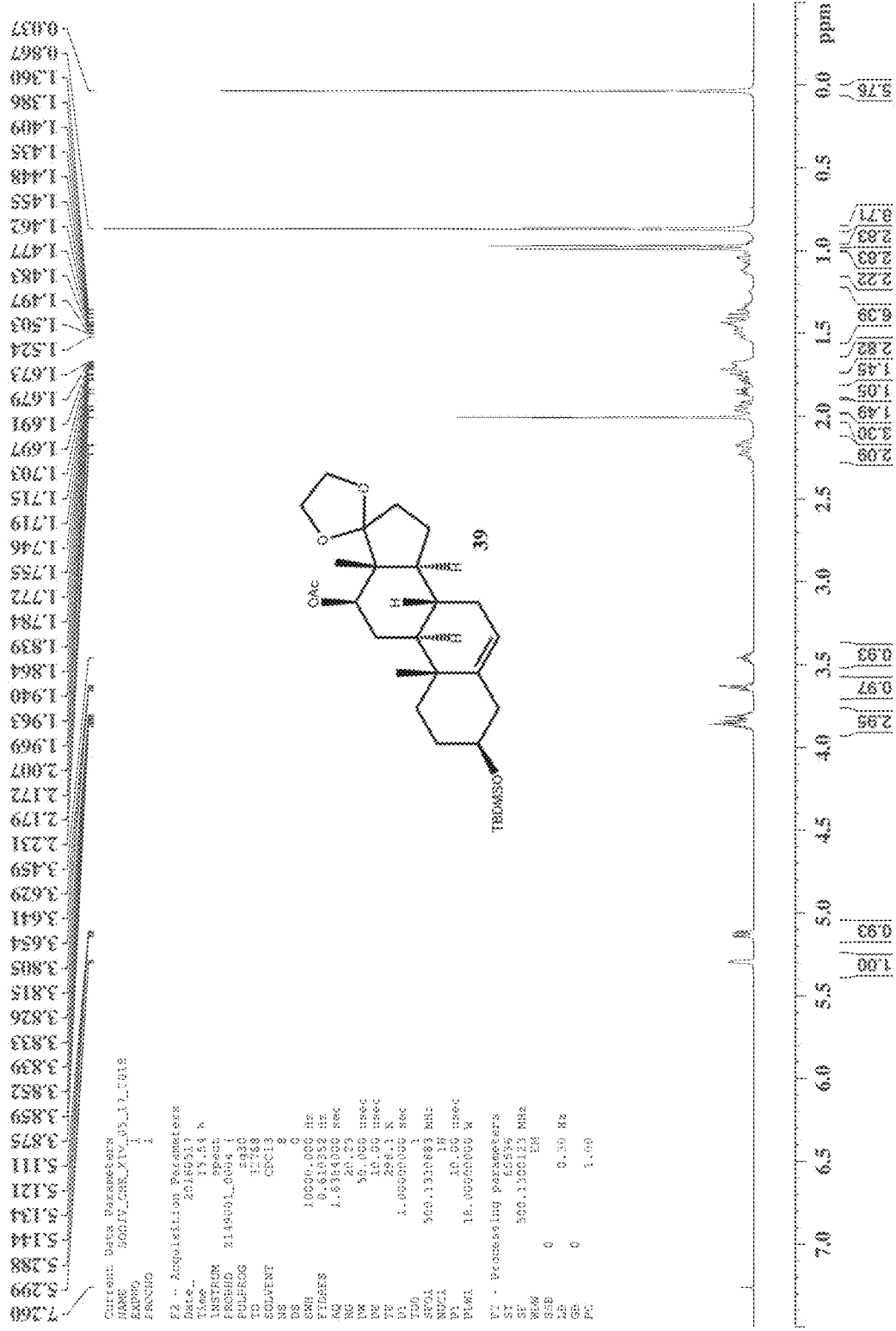
FIGS. 76-79 show $^1$H and $^{13}$C NMR, HRMS, and IR spectra of Compound 39.
Figure 77:
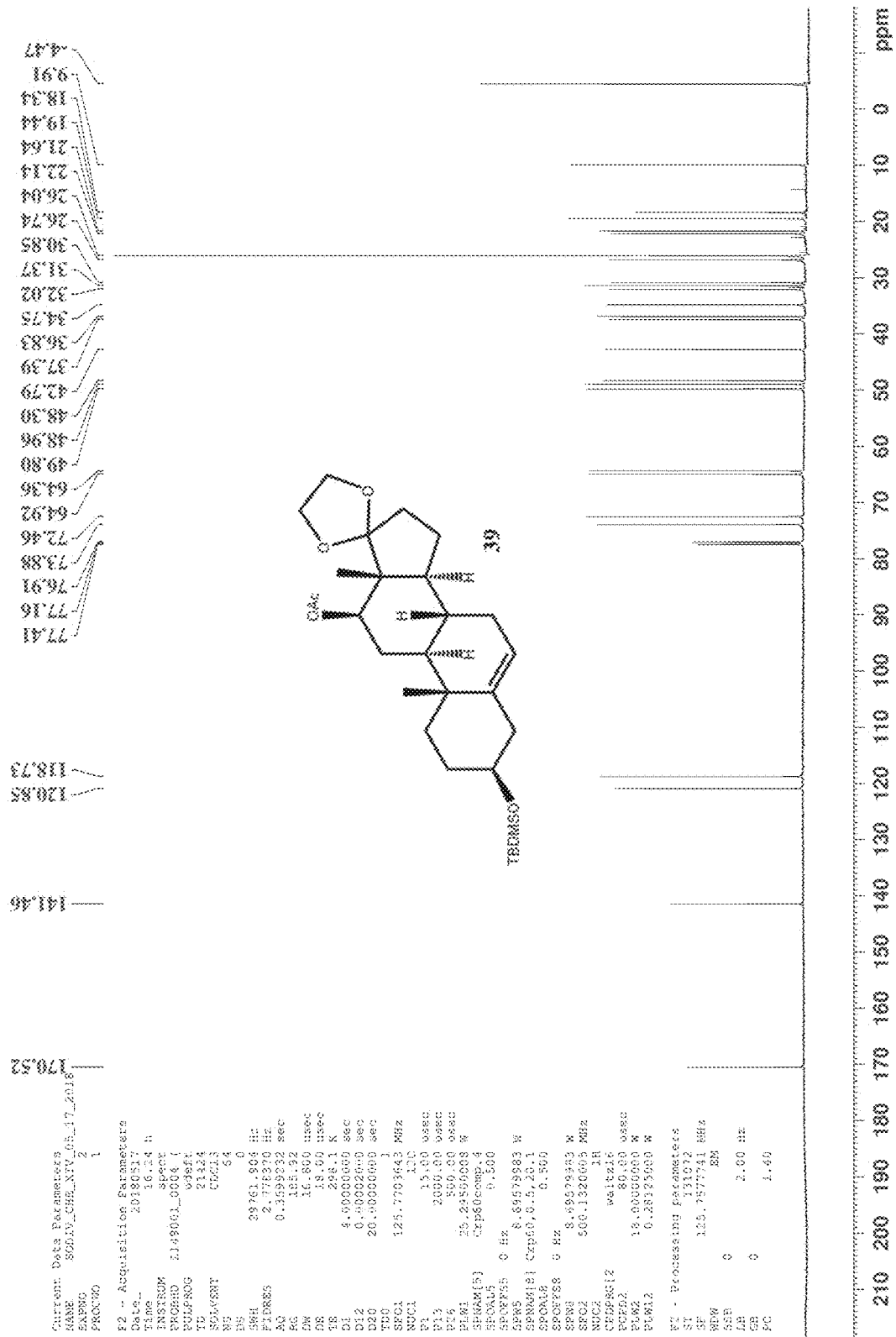
Figure 78:
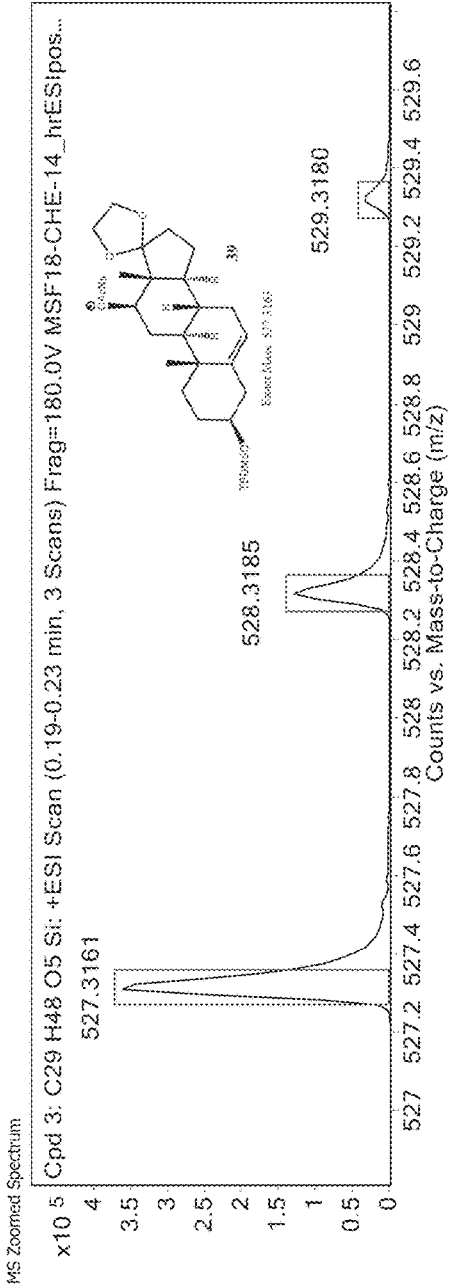
Figure 79:
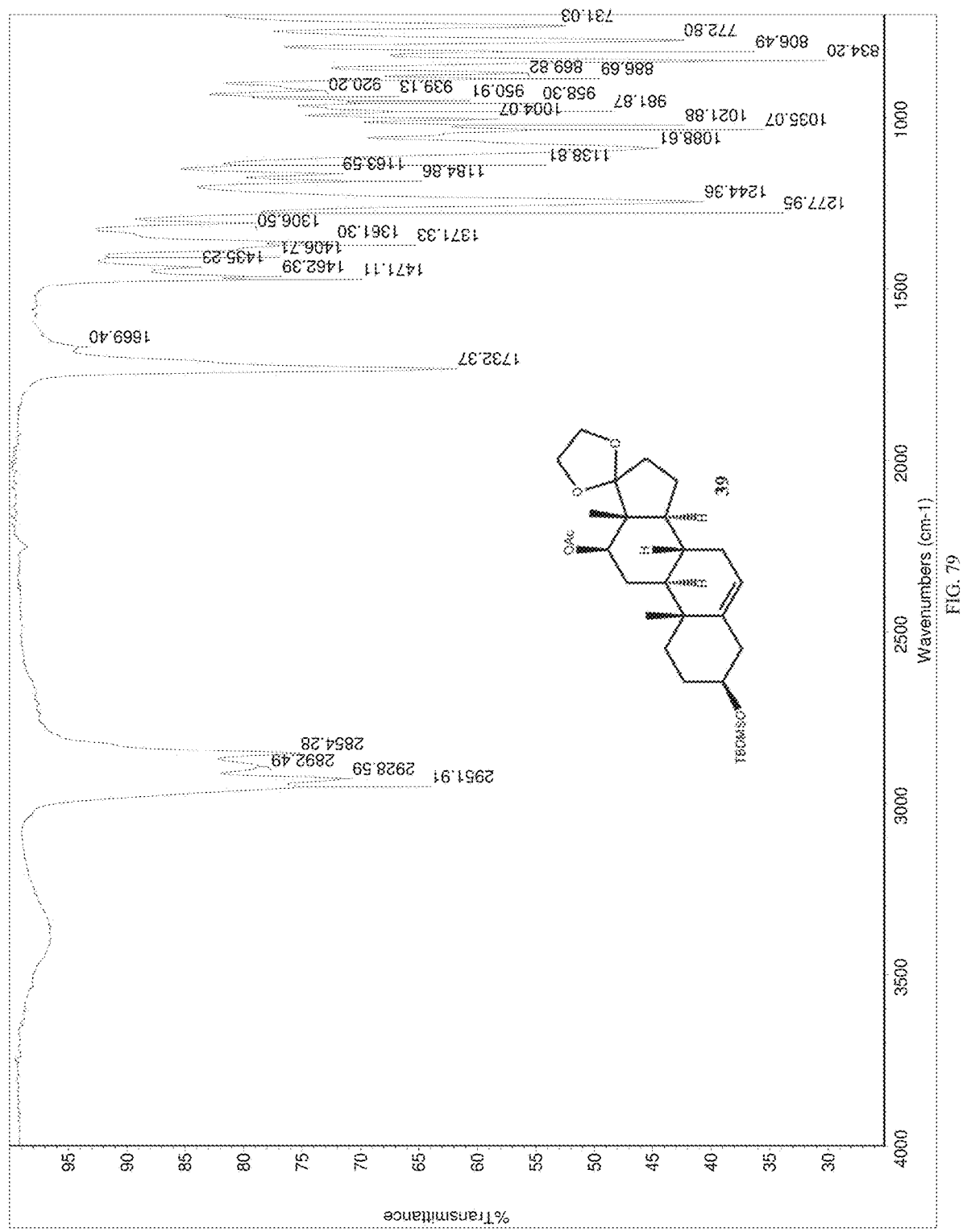
Figure 80:
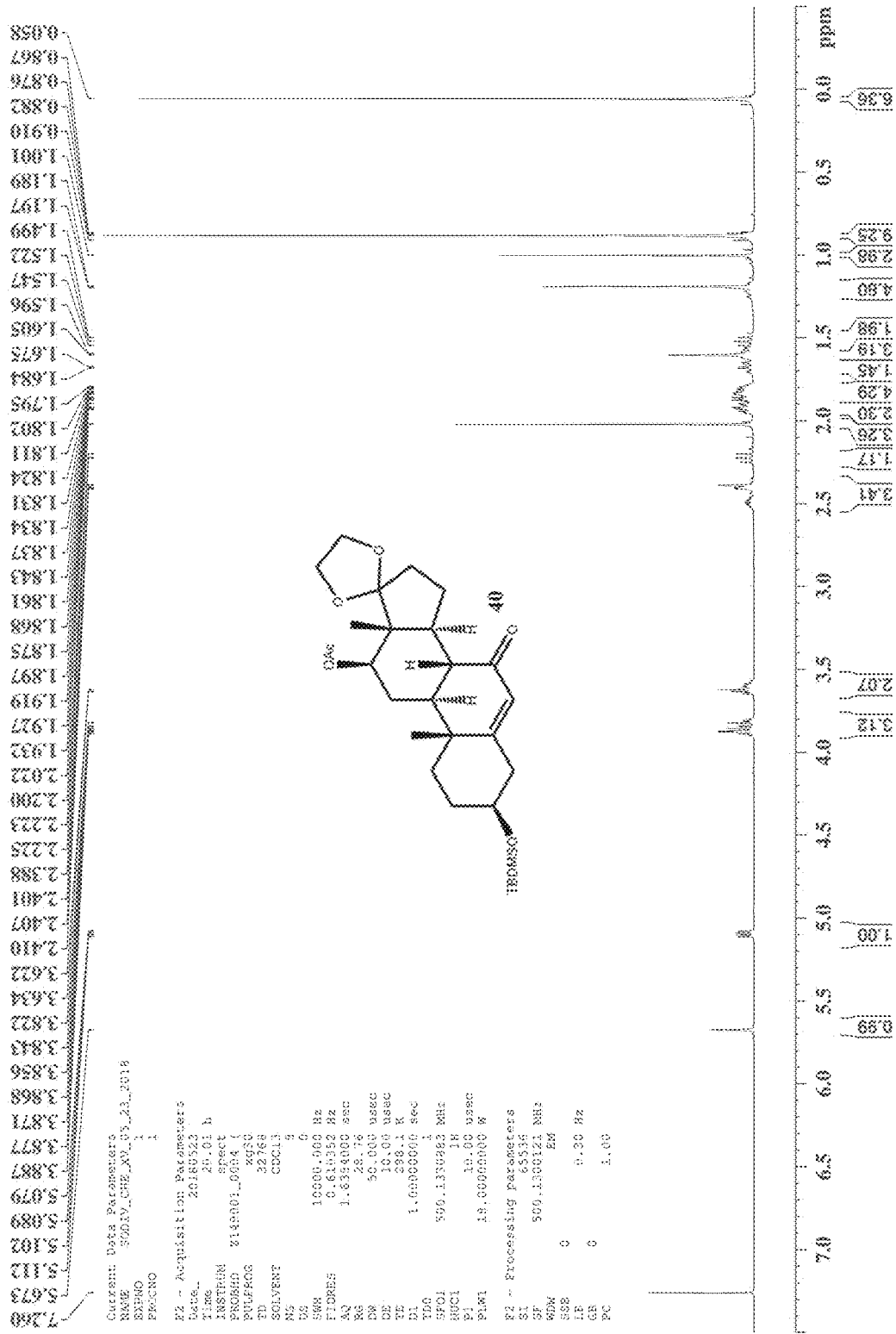
FIGS. 80-83 show $^1$H and $^{13}$C NMR, HRMS, and IR spectra of Compound 40.
Figure 81:
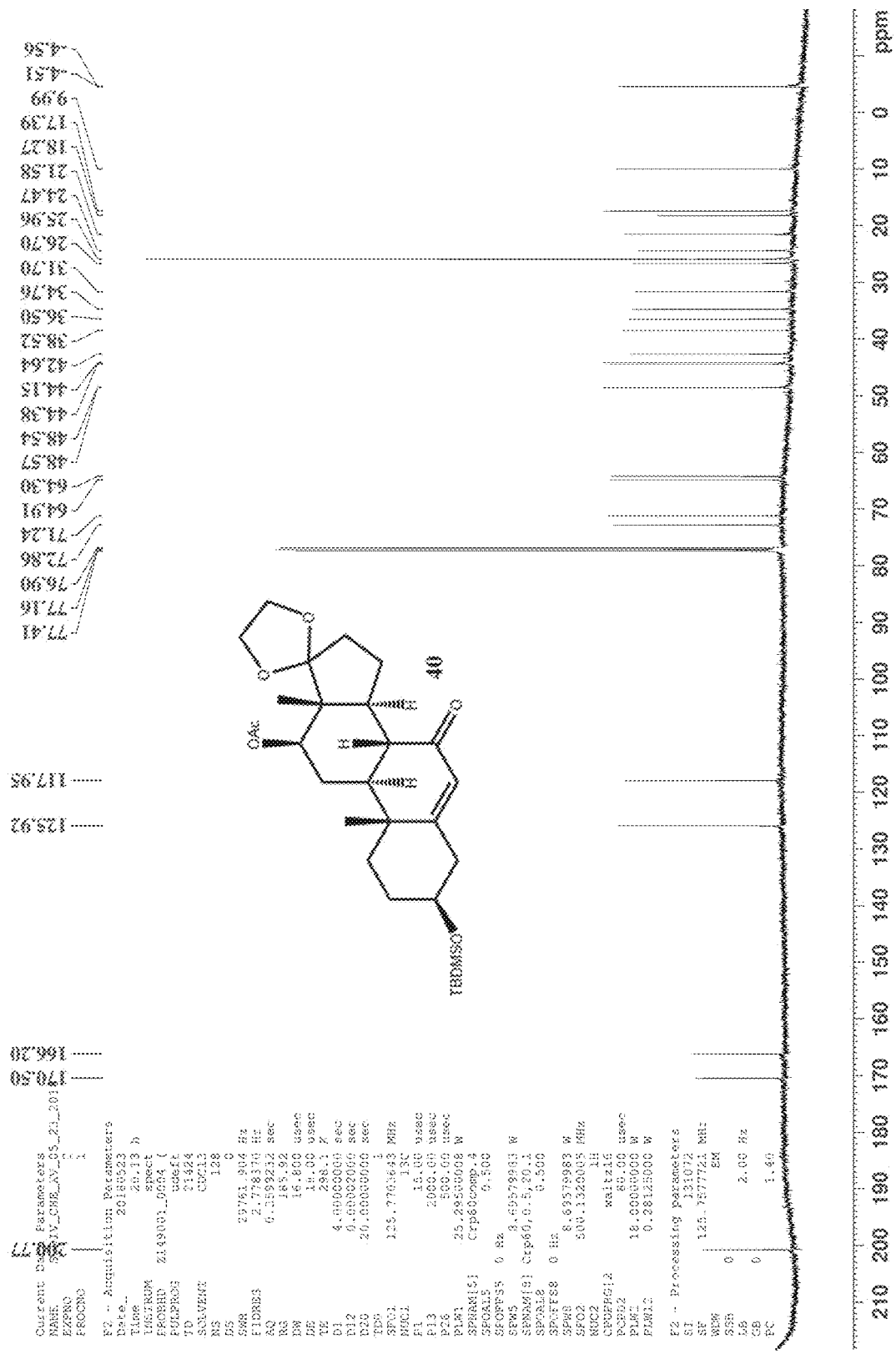
Figure 82:
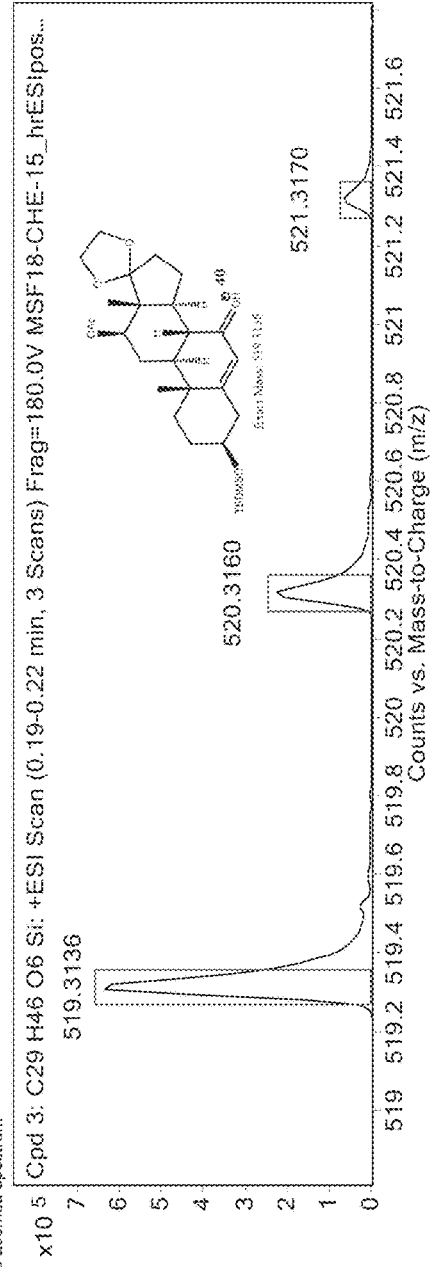
Figure 83:
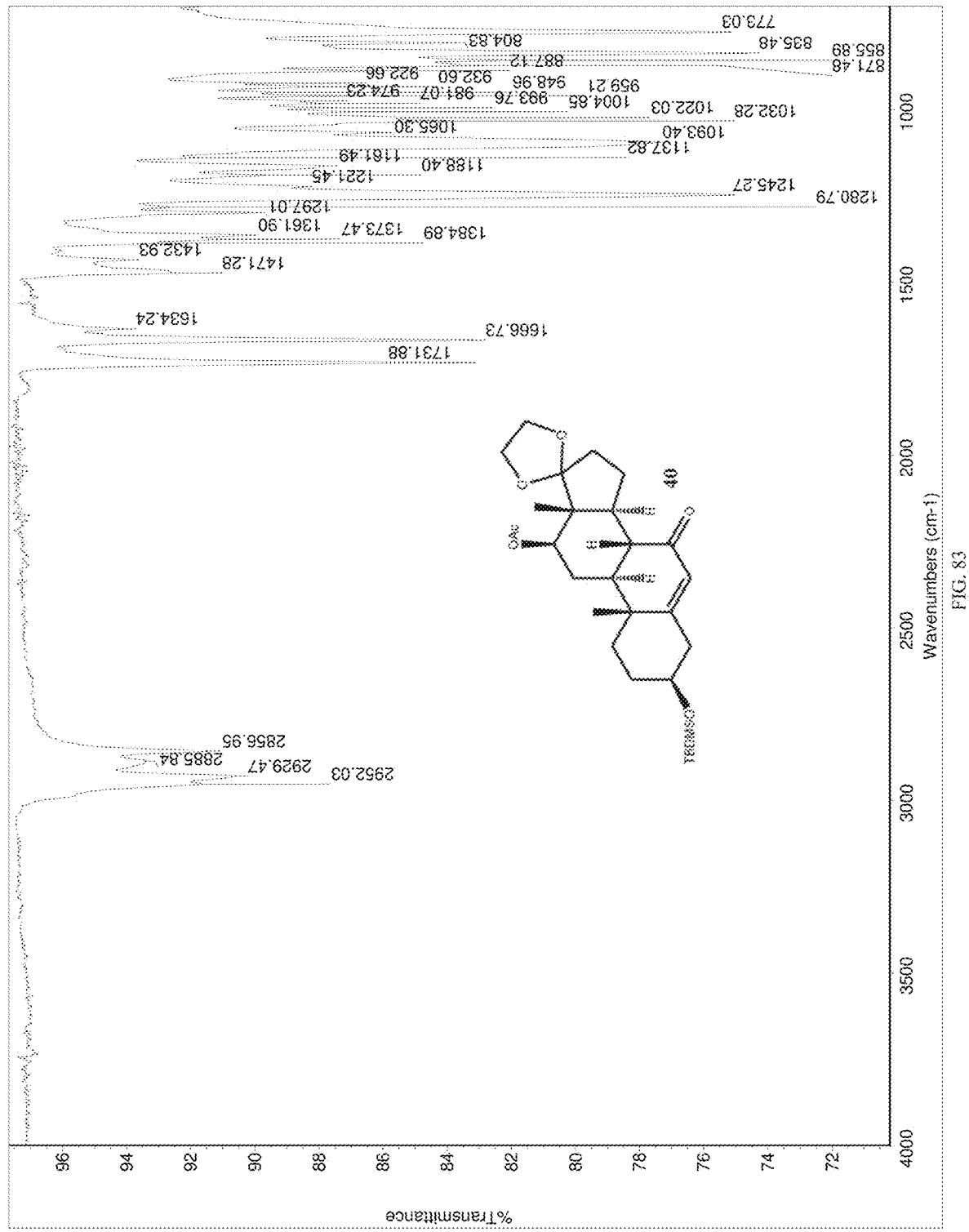
Figure 84:
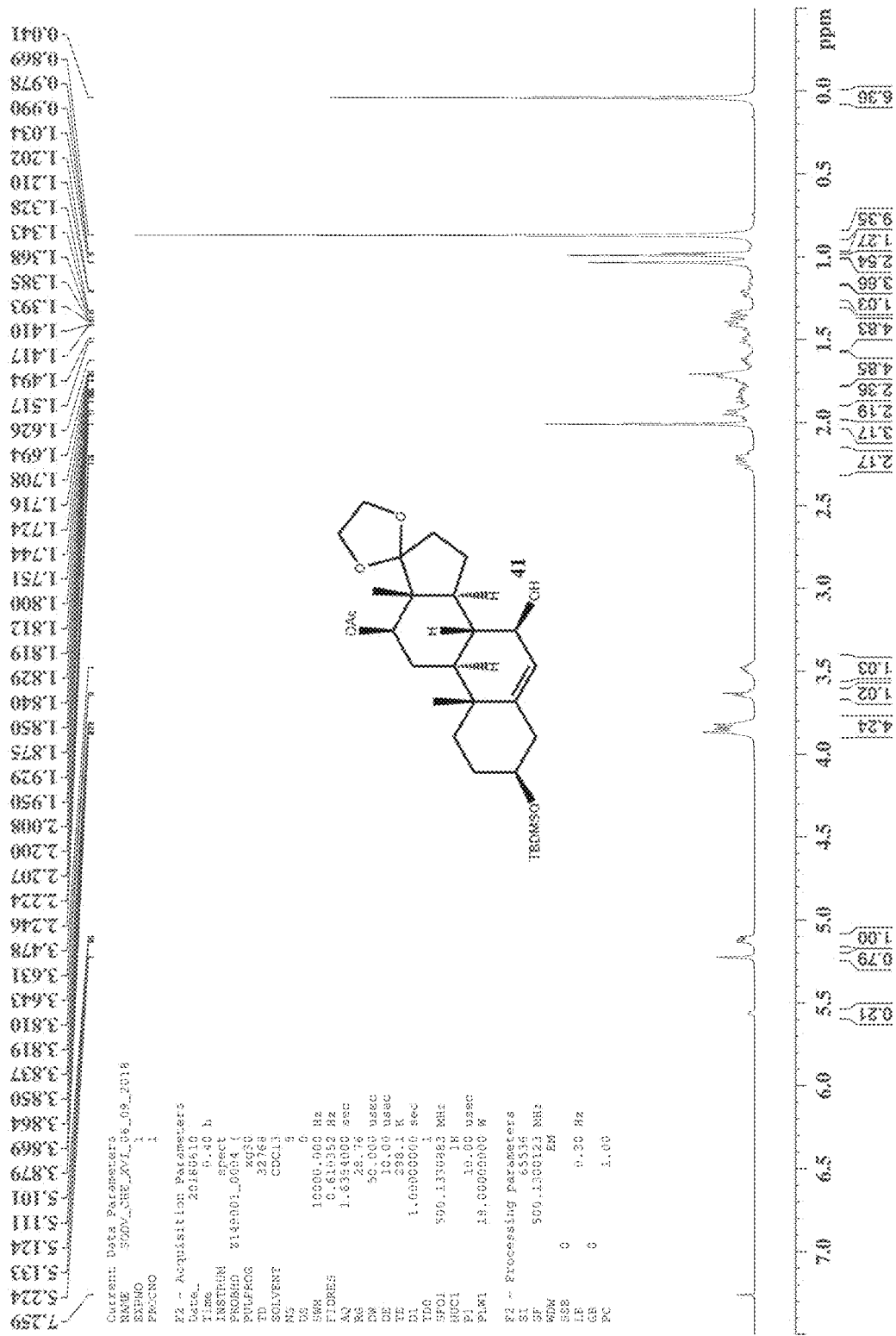
FIGS. 84-87 show $^1$H and $^{13}$C NMR, HRMS, and IR spectra of Compound 41.
Figure 85:
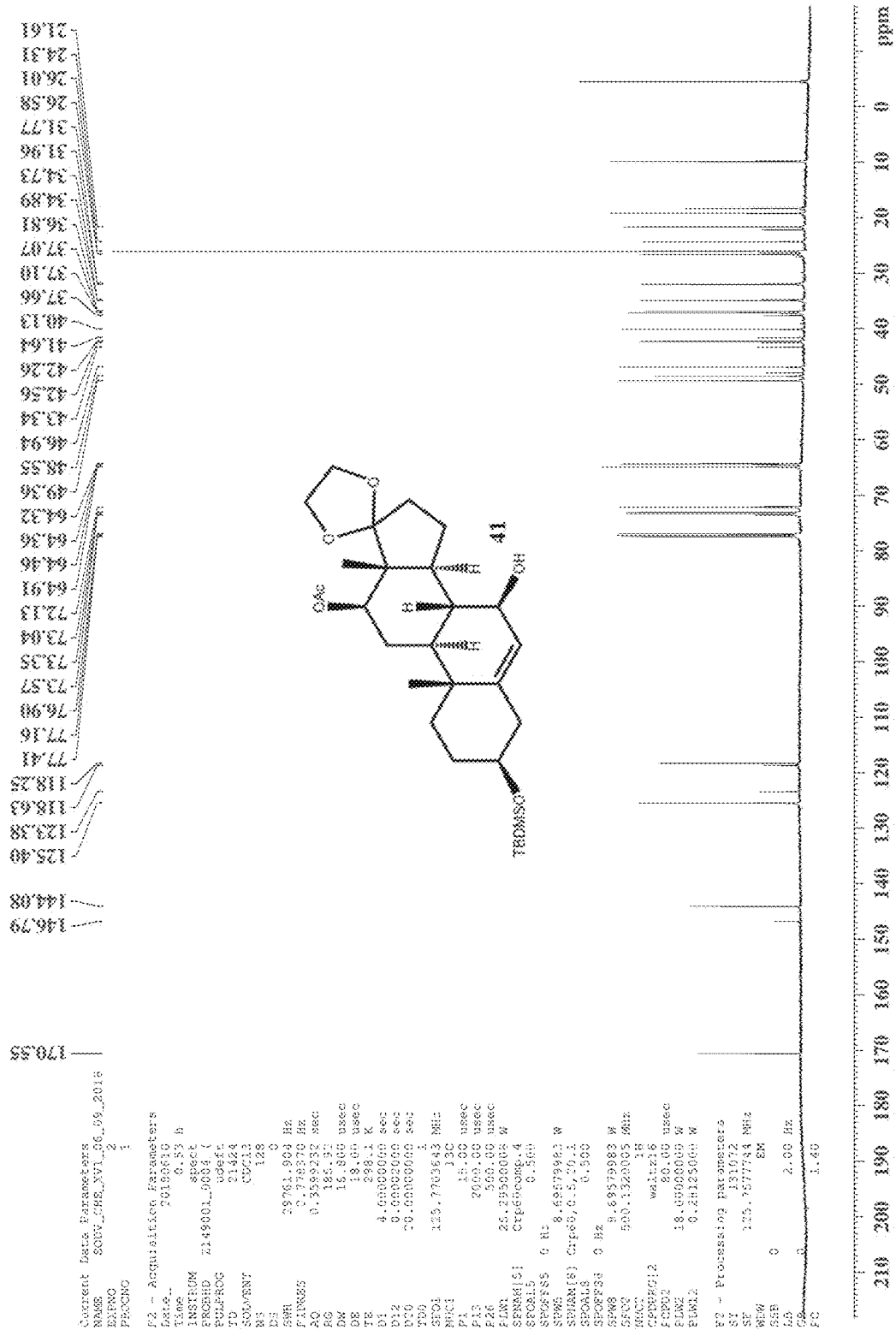
Figure 86:
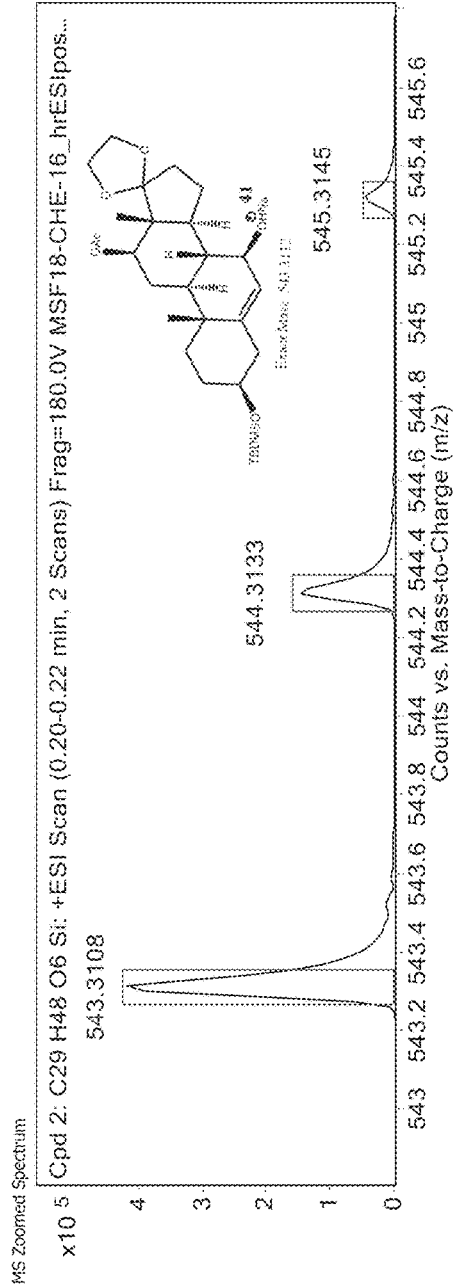
Figure 87:
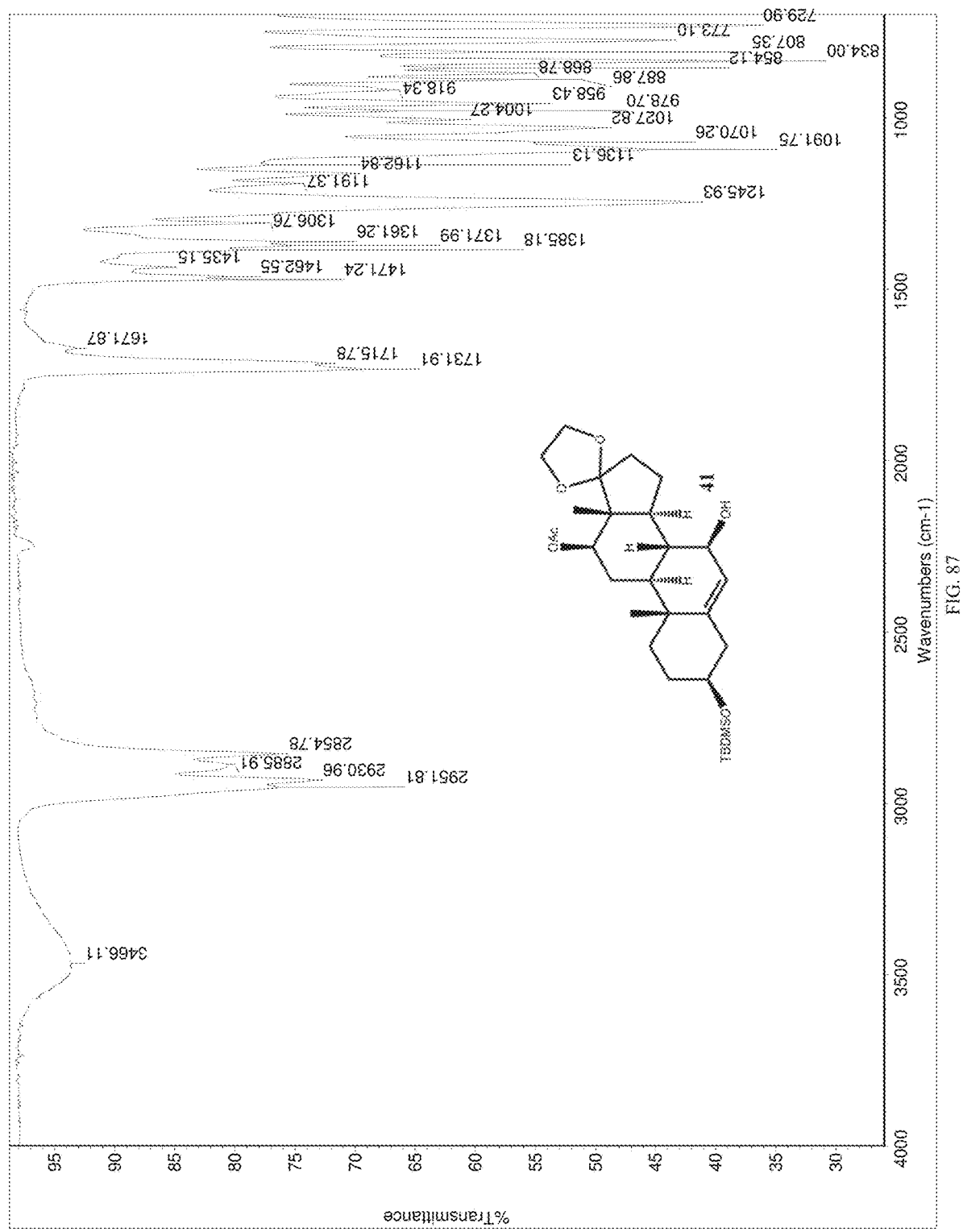
Figure 88:
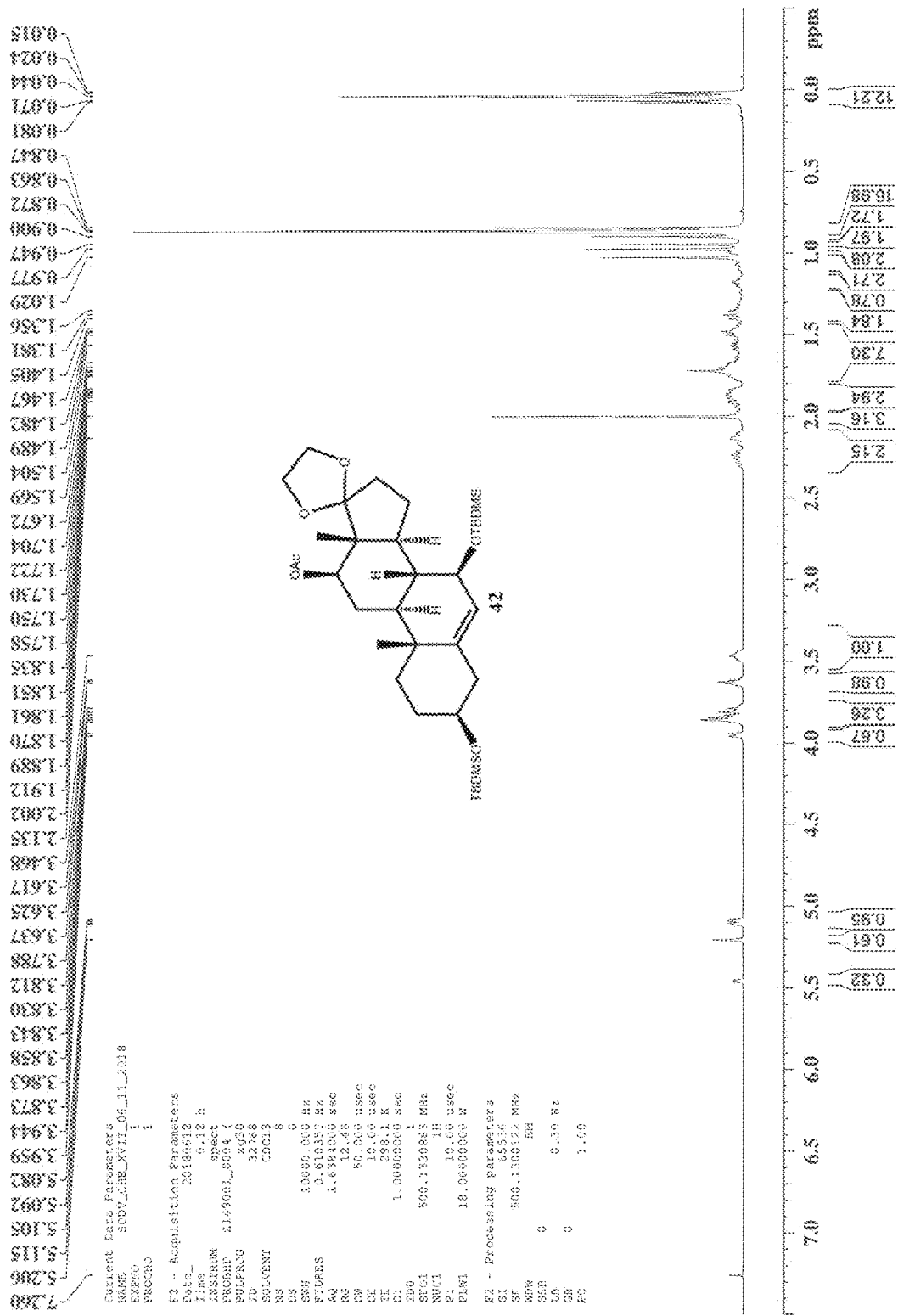
FIGS. 88-91 show $^1$H and $^{13}$C NMR, HRMS, and IR spectra of Compound 42.
Figure 89:
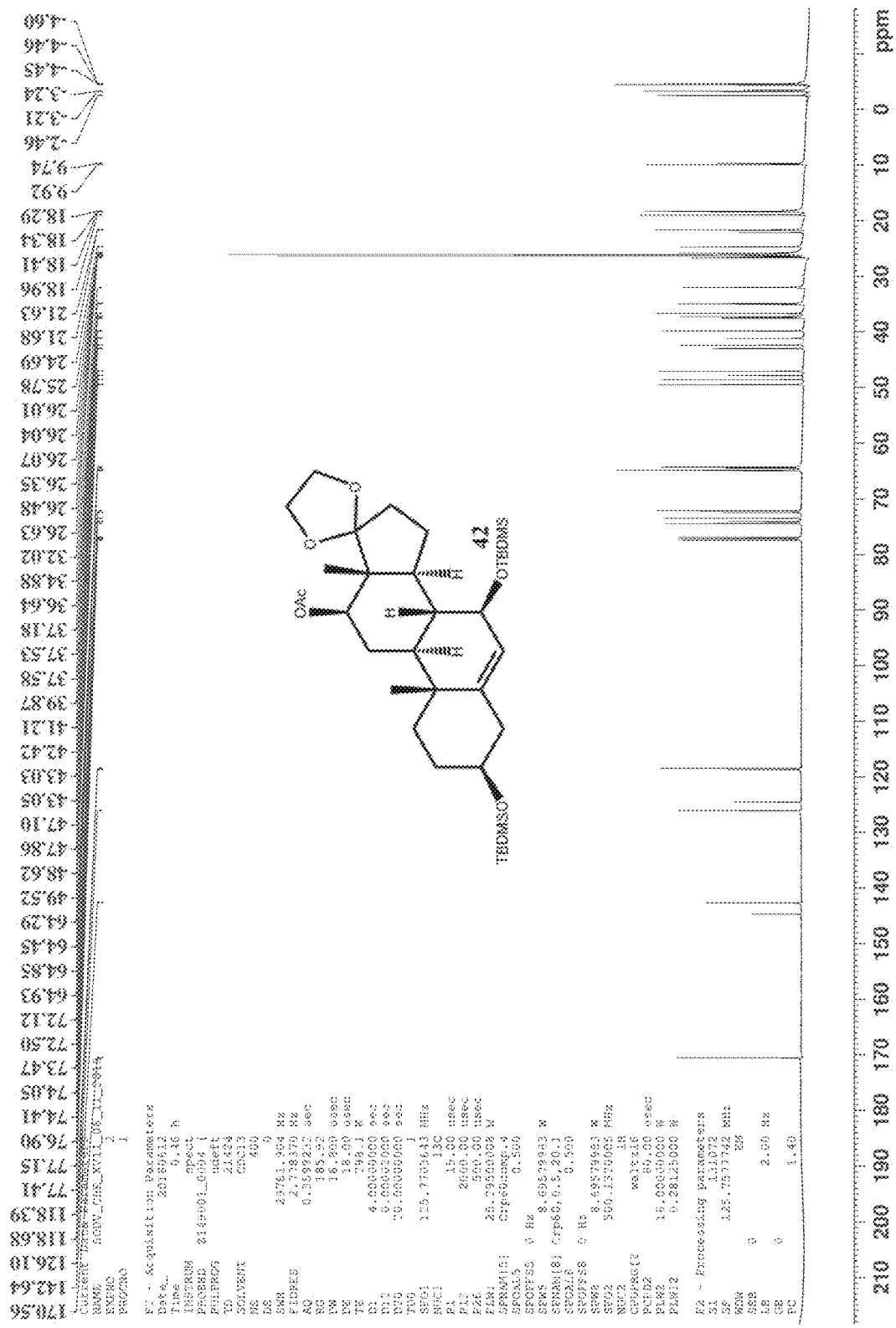
Figure 90:
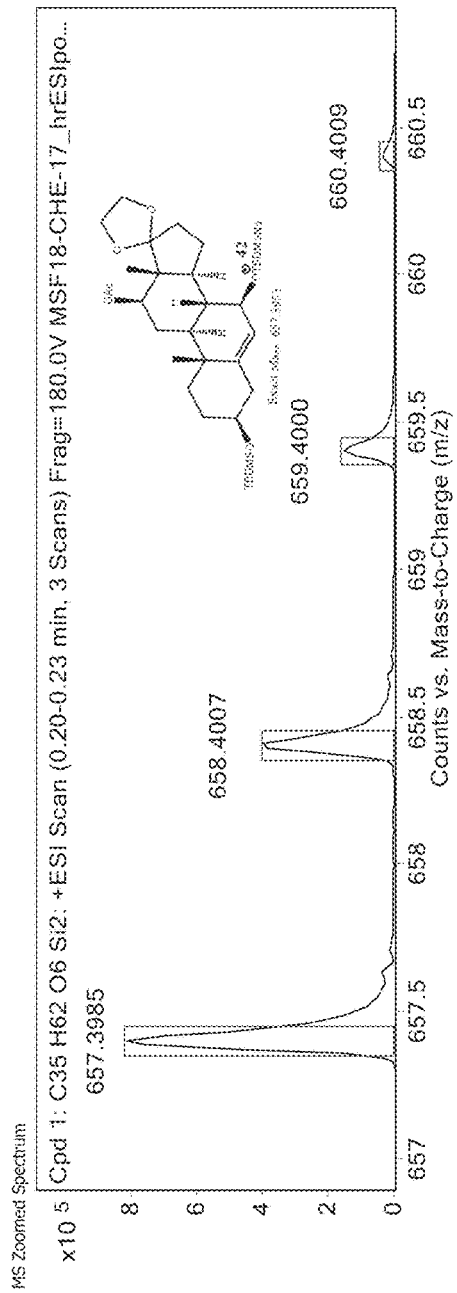
Figure 91:
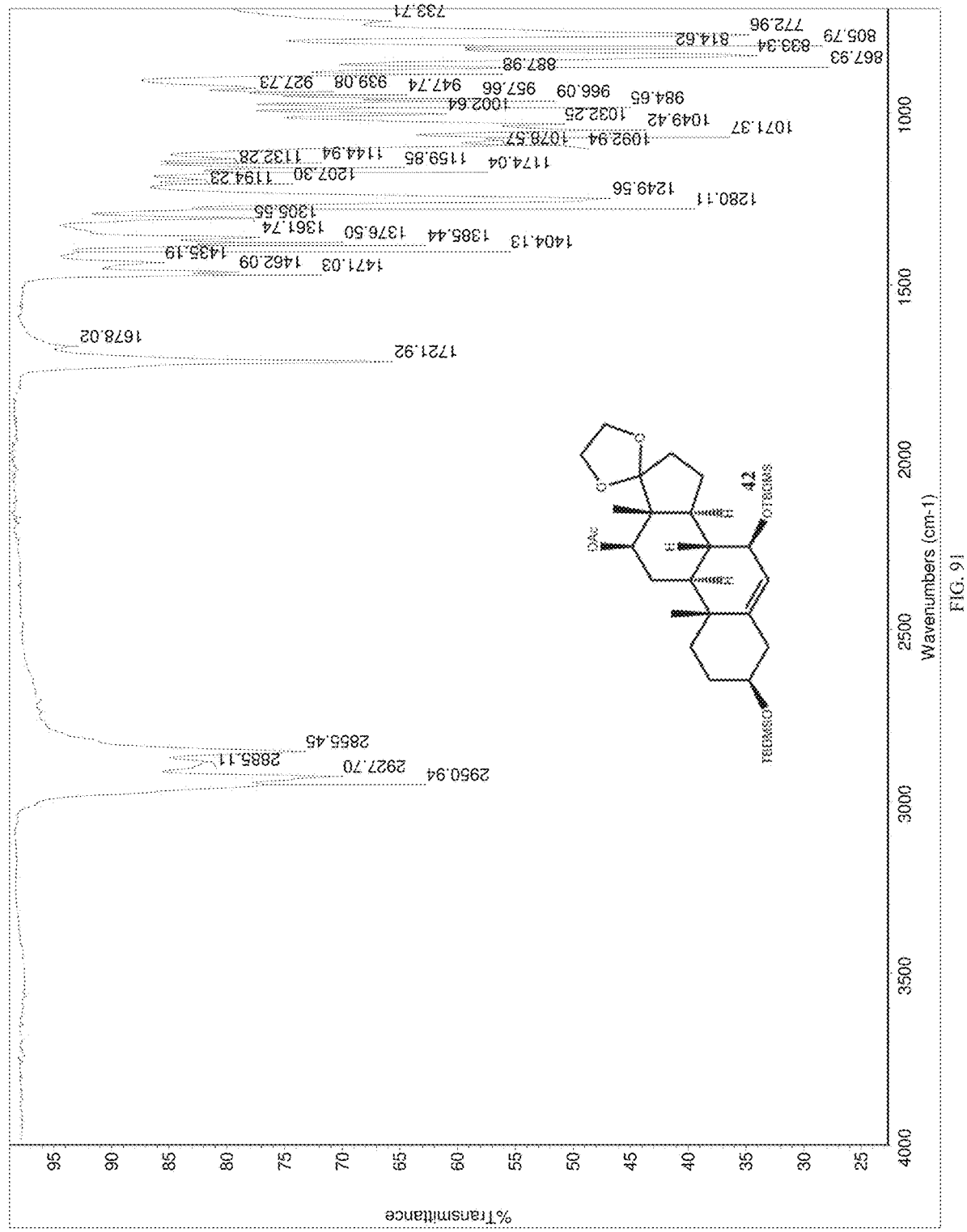
Figure 92:
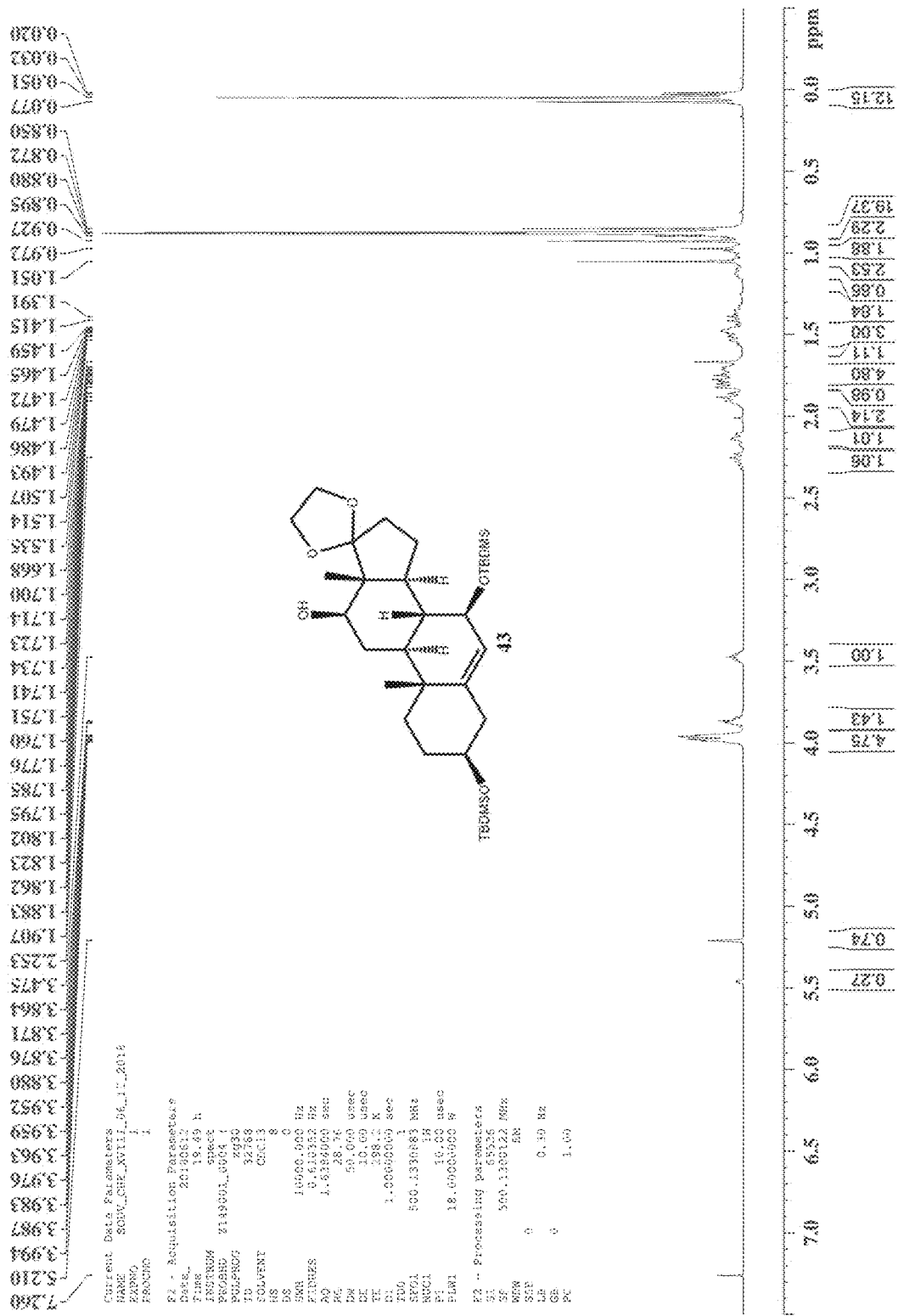
FIGS. 92-96 show $^1$H and $^{13}$C NMR, HRMS, and IR spectra of Compound 43.
Figure 93:
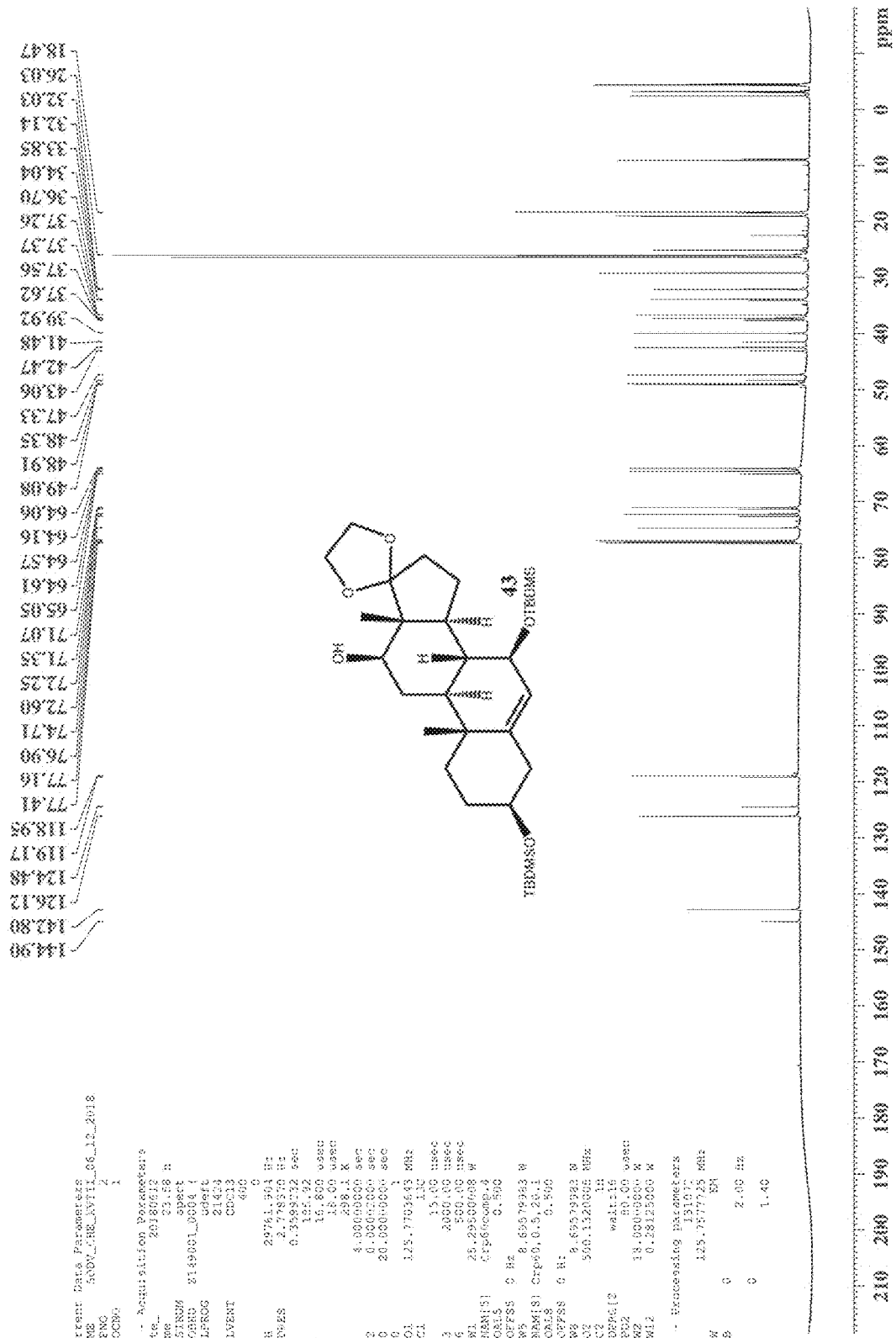
Figure 94:
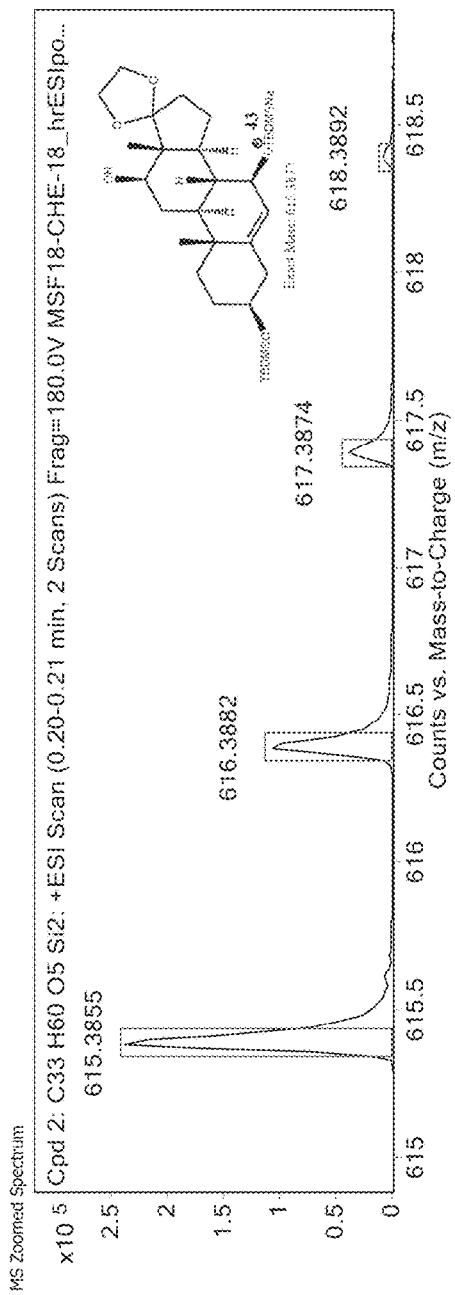
Figure 95:
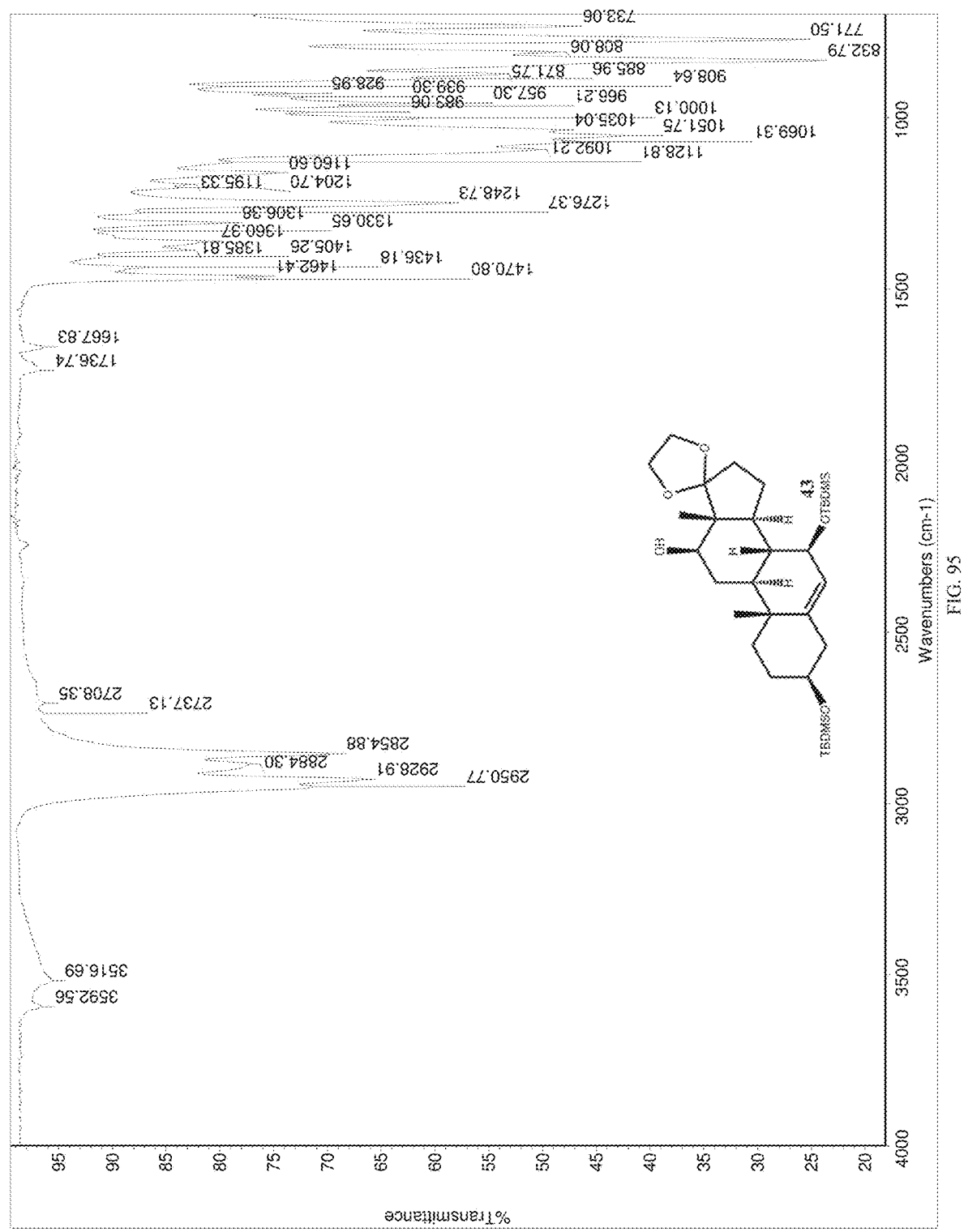
Figure 96:
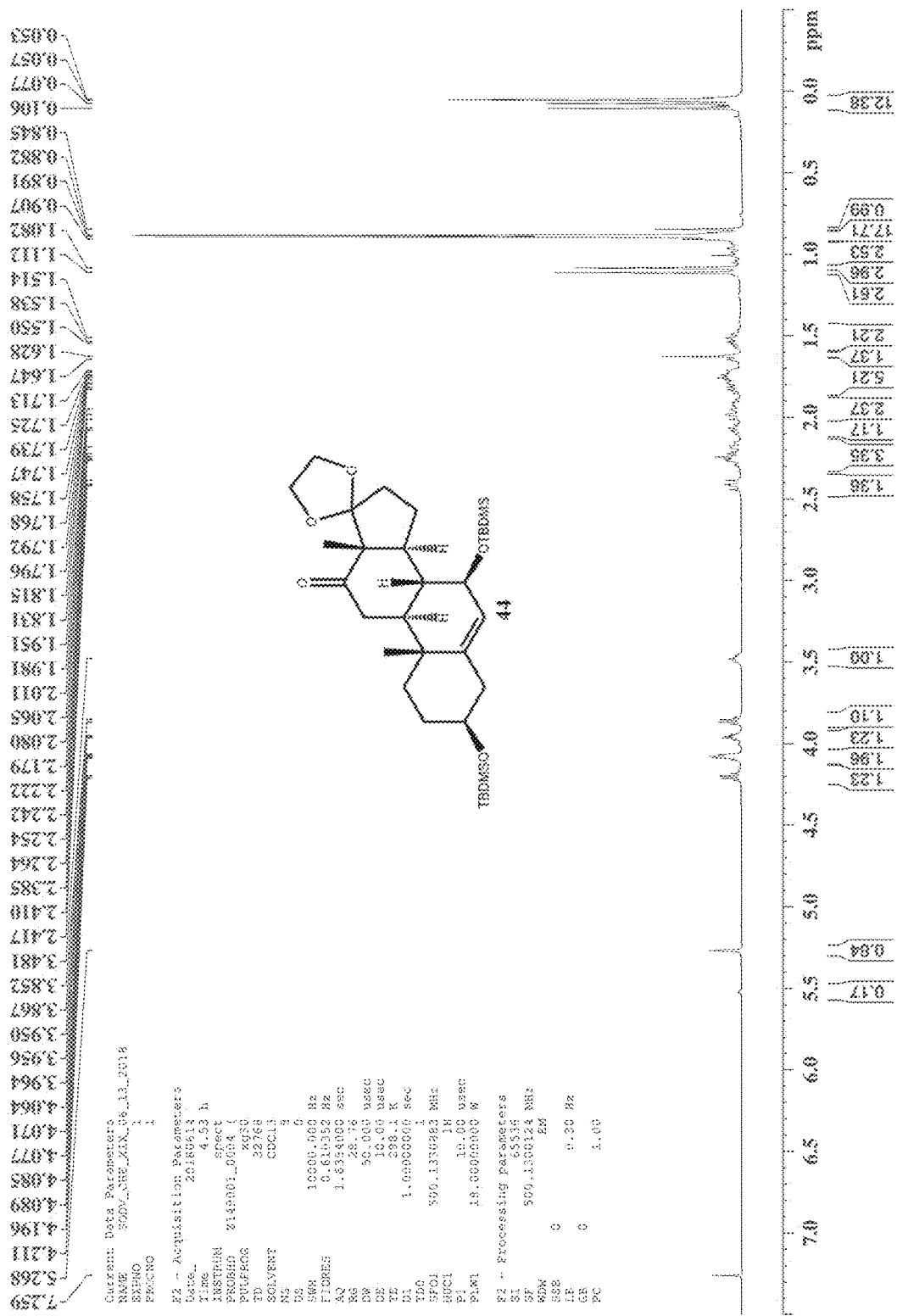

FIG. 23 illustrates the creation of make C11-heteroatom and C11-heterocyclic analogs. Experimental Section Materials. Reagents and solvents were purchased from commercial sources. TLC plates (silica gel) with 254 nm fluorescent indicator (Sigma, St. Louis, Mo.) were used to monitor reactions. Both a UV lamp and ceric ammonium molybdate staining were used to visualize compounds on TLC. Silica gel (Silicycle (Quebec, Canada), 40-63 μm, 60 Å) was used for flash column separations. A WXG-4 optical polarimeter (Bante Instruments, Ltd, Shanghai, China) was used to measure optical rotations with a 10 cm long cell. A melting point apparatus (Global Medical and Lab Solutions, India) was used to measure the melting points of each compound. CDCl3 (Cambridge Isotope Laboratories, Tewksbury, Mass.) was used to take NMR spectra. The chloroform peaks were referenced to δ 7.26 ppm and δ 77.16 ppm for the 1H NMR and 13C NMR, respectively. Infrared (IR) spectra were recorded using a Nicolet iS50 FT-IR Spectrometer (Thermo Fisher Scientific, Waltham, Mass.). OMNIC software (version 9.3.32) was used to analyze the IR data (Thermo Fisher Scientific, Waltham, Mass.).

General Experimental Protocols. Bruker NMR spectrometers (Billerica, Mass.) were used at 25° C. to record proton (1H) and carbon (13C) NMR spectra. For optical rotations, synthesized compounds were dissolved in CHCl3 (15 ml) into a polarimeter cell with 1 dm in length (l). The specific rotation $[\alpha]D\ 20$ were calculated using the equation $[\alpha]D\ 20=\alpha/(l*c)$, where α, the observed rotation, is: [(calibrated angle obtained from a blank solution (CHCl3) (measured angle of the sample)], and c is the concentration of the sample in a solution of CHCl3 (g/100 ml).

Chemical Synthesis.

DHEA-3β-tert-butyldimethylsilyl ether (Compound 29): tert-Butyldimethylsilyl chloride (9.05 g, 60 mmol, 3 eq) and Imidazole (6.81 g, 100 mmol, 5 eq) were added to a solution of Dehydroepiandrosterone (DHEA) (6.00 g, 20 mmol, 1 eq) in acetonitrile (100 ml). The reaction was stirred at room temperature for 6 h. The reaction mixture was diluted with water (50 ml) and extracted three times with ethyl acetate (3×50 ml). The organic layer was concentrated under reduced pressure to afford DHEA-3β-tert-butyldimethylsilyl ether as a white solid. No further purification was done (7.70 g, 19 mmol, 95%); mp: 118-123° C.; Rf: 0.86 (Hexanes: Ethyl acetate, 4:1, v/v); $[\alpha]D\ 20\ -83.3°$ [0.09% in CHCl3]; IR (neat) 2926.42, 2889.06, 2856.05, 1738.49, 1462.61, 1379.73, 1250.67, 1076.66, 1059.33 cm−1; 1H NMR (500 MHz, CDCl3) δ 5.34 (d, J=6 Hz, 1H), 3.48 (m, 1H), 2.45 (dd, J=19, 8 Hz, 1H), 2.27 (m, 1H), 2.19 (m, 1H), 2.08 (m, 2H), 1.94, (m, 1H), 1.82 (m, 2H), 1.74-1.42 (m, 8H), 1.29-1.27 (m, 2H), 1.09-0.96 (m, 5H), 0.88 (s, 12H), 0.05 (s, 6H); 13C NMR (500 MHz, CDCl3) δ 141.94, 120.54, 72.59, 51.95, 50.47, 47.70, 42.93, 37.45, 36.87, 35.99, 32.16, 31.67, 31.61, 30.97, 26.06, 22.03, 20.50, 19.60, 18.39, 13.68, −4.42; HRMS (m/z) calculated for C25H42O2SiNa [M+Na]+, 425.2846; found, 425.2839 (T 1.64 ppm).

Imine (Compound 30): To a solution of DHEA-3β-tert-butyldimethylsilyl ether (3.00 g, 7.5 mmol, 1 eq) in toluene (100 ml) was added 2-aminomethyl pyridine (2.20 g, 23 mmol, 3 eq) and (50 mg, 0.2 mmol, 0.03 eq) of para-toluenesulfonic acid. The solution was refluxed for 4 h with a Dean Stark apparatus at 150° C. The progress of the reaction was monitored by 1H NMR. The reaction was cooled to room temperature. The reaction mixture was diluted with ethyl acetate and subsequently washed three times with saturated NaHCO3 (200 ml), dried with MgSO4 and concentrated under reduced pressure to afford the imine as a white solid. No further purification was done (3.1904 g, 6.8 mmol, 90%). mp: 99-104° C.; $[\alpha]\ 20+12.22°$ [0.12% in CHCl3]; IR (neat) 2940.26, 2927.23, 2890.02, 2856.88, 1745.74, 1678.36, 1590.54, 1567.92, 1471.49, 1435.35, 1382.00, 1254.46, 1083.24 cm−1; 1H NMR (500 MHz, CDCl3) δ 8.52 (d, J=5 Hz, 1H), 7.65 (td, J=8, 2 Hz, 1H), 7.42 (dt, J=8 Hz, 1H), 7.14-7.09 (m, 1H), 5.33 (d, J=6 Hz, 1H), 4.58 (ABq, JAB=16.7 Hz, 2H), 3.48 (M, 1H), 2.45 (dd, J=17, 9 Hz, 1H), 2.34-2.13 (m, 3H), 2.25-1.98 (m, 2H), 1.92-1.79 (m, 3H), 1.67-1.48 (m, 3H), 1.48-1.30 (m, 2H), 1.13-0.96 (m, 6H), 0.93-0.89 (s, 3H), 0.88 (s, 9H), 0.05 (s, 6H); 13C NMR (500 MHz, CDCl3) δ 186.19, 160.62, 149.07, 141.92, 136.65, 128.87, 126.07, 122.35, 121.66, 120.66, 120.73, 120.51, 72.63, 58.10, 53.43, 50.71, 42.93, 37.48, 36.48, 34.19, 32.17, 31.45, 28.16, 26.05, 23.47, 20.85, 19.67, 18.37, 16.34, −4.46; HRMS (m/z) calculated for C31H49 N2OSi [M+H]+, 493.3609; found, 493.3611 (T −0.48 ppm). 12β-Hydroxy-DHEA-3β-tert-butyldimethylsilyl ether (Compound 31): Copper triflate, (2.11 g, 5.84 mmol, 1.3 eq) and sodium-(L)-ascorbate (1.778 g, 8.98 mmol, 2 eq) were added to the imine (2.12 g, 4.4 mmol, 1 eq) in an oven baked round bottom flask backfilled with N2. Acetone (18 ml) and methanol (18 ml) were added to the mixture and stirred for 10 minutes. The reaction solution turned brown after stirring for 5 minutes. The round bottom flask containing the reaction mixture was sealed with a rubber stopper and degassed. The reaction solution was bubbled with O2 gas with the aid of a balloon and an exit needle until the color of the solution changed from brown to green. The reaction mixture was heated at 50° C. under an atmosphere of O2 for 2 h.

The reaction was cooled to room temperature and then quenched by adding saturated Na4EDTA (30 ml, pH=5) and ethyl acetate (15 ml). The resulting solution was stirred for 1 h and then transferred to a separatory funnel and allowed to stand for 5 minutes to differentiate the organic layer from the aqueous layer. The organic layer was separated from the aqueous layer. The aqueous layer was extracted with ethyl acetate (150 ml). The combined organic layers were concentrated under reduced pressure to afford a crude brown oil. The crude brown oil was purified by flash column chromatography to afford the alcohol as a white solid (0.9 g, 2.1 mmol, 48%); mp: 165-169° C.; Rf: 0.79 (Hexanes: Ethyl acetate, 1:1, v/v); $[\alpha]D\ 20\ -23.5°$ [0.17% in CHCl3]; IR (neat) 3545.58, 2949.63, 2928.84, 2890.64, 1733.18, 1470.79, 1403.66, 1359.09, 1291.15, 1270.45, 1111.92, 1047.42, 1027.11, 1018.23 cm−1; 1H NMR (500 MHz, CDCl3) δ 5.34 (d, J=6 MHz, 1H), 3.8 (dd, J=11.3, 4.9, 1H), 3.47 (m, 1H), 3.06 (s, 1H), 2.47 (dd, J=19, 10, 1H), 2.31-2.16 (m, 2H), 2.17-2.04 (m, 2H), 2.02-1.95 (m, 1H), 1.86-1.77 (dt, J=13, 5, 2H), 1.76-1.70 (m, 1H), 1.69-1.57 (m, 3H), 1.57-1.50 (m, 1H), 1.49-1.37 (m, 1H), 1.29-1.19 (m, 1H), 1.16-1.06 (m, 1H), 1.06-0.99 (m, 3H), 0.95 (s, 3H), 0.88 (s, 9H), 0.07 (s, 6H); 13C NMR (500 MHz, CDCl3) δ 141.94, 120.35, 77.82, 77.51, 51.54, 49.72, 49.35, 42.83, 37.40, 37.00, 35.90, 32.10, 30.74, 30.55, 26.05, 21/84, 19.51, 18.38, 8.19, −4.45; HRMS (m/z) calculated for C25H42O3SiNa [M+Na]+, 441.2795; found, 441.2795 (T −0.01 ppm).

12β-Hydroxy-DHEA-3β-tert-butyldimethylsilyl ether 17-ethylene ketal (Compound 32): Ethylene glycol (2 ml, 35.9 mmol, 16 mol eq), para-toluenesulfonic acid (0.103 g, 0.59 mmol, 0.28 eq) were added to the alcohol (0.89 g, 2.13 mmol, 1 eq) in toluene (100 ml). The reaction was refluxed with a Dean Stark apparatus at 147° C. for 4 h and allowed to cool to room temperature. The reaction mixture was diluted with ethyl acetate, washed three times with saturated NaHCO3 and dried with Magnesium Sulfate. The resulting solution was concentrated under reduced pressure to form a crude yellowish-brown oil which was the purified by silica gel column chromatography to afford the ketal as white solids (0.2064 g, 0.44 mmol, 20%); mp: 140-143° C.; Rf: 0.15 (Hexanes: Ethyl acetate, 4:1, v/v); [α]D 20 −12.5° [0.12% in CHCl3]; IR (neat) 3574.56, 3545.91, 2929.47, 2891.15, 2854.47, 1733.91, 1470.18, 1434.08, 1381.34, 1371.54, 1248.77, 1217.62, 1080.94, 1048.63, 1033.95 cm−1; 1H NMR (500 MHz, CDCl3) δ 5.31 (d, J=5 Hz, 1H), 4.03-3.95 (m, 4H), 3.91-3.85 (m, 1H), 3.47 (m, 1H), 2.30-2.22 (m, 1H), 2.21-2.14 (m, 1H), 2.05-1.96 (m, 1H), 1.97-1.86 (m, 1H), 1.86-1.77 (m, 3H), 1.76-1.68 (m, 3H), 1.67-1.59 (m, 2H), 1.57-1.50 (m, 2H), 1.50-1.41 (m, 2H), 1.42-1.38 (m, 1H), 1.38-1.35 (m, 2H), 1.10-0.99 (m, 5H), 0.90 (s, 3H), 0.88 (s, 3H), 0.05 (s, 6H); 13C NMR (500 MHz, CDCl3) δ 141.65, 120.89, 119.25, 72.59, 71.51, 49.41, 49.25, 48.87, 42.84, 37.48, 36.84, 32.10, 35.95, 32.15, 31.38, 30.97, 29.53, 26.07, 22.47, 19.55, 18.37, 9.01, −4.41; HRMS (m/z) calculated for C27H46O4SiNa [M+Na]+, 485.3058; found, 485.3051 (T 1.42 ppm).

12-Oxo-DHEA-3β-tert-butyldimethylsilyl ether 17-ethylene ketal (Compound 33): Pyridinium chlorochromate (0.90 g, 19 mmol, 1 eq) was added to a solution of the ketal-alcohol 32 (0.90 g, 19 mmol, 1 eq) in dichloromethane (50 ml). The solution was stirred at room temperature for 6 h. The reaction mixture was washed with 5% NaOH (3×50 ml) and then concentrated under reduced pressure to obtain a crude yellow solid residue. The crude residue was purified by silica gel column chromatography (100% hexanes to 90% hexanes in ethyl acetate) to afford a whit solid (0.419 g, 0.909 mmol, 48%); mp: 110-114° C.; Rf: 0.77 (hexanes: ethyl acetate, 4:1, v/v); [α]D 20+6.25° [0.08% in CHCl3]; IR (neat) 3545.09, 2934.26, 2893.37, 2854.03, 1714.58, 1460.25, 1434.19, 1381.52, 1359.66, 1246.17, 1178.01, 1074.15, 1050.79, 1025.94 cm−1; 1H NMR (500 MHz, CDCl3) δ 5.34 (d, J=6 Hz, 1H), 4.28-4.15 (m, 1H), 4.15-4.08 (m, 1H), 4.01-3.90 (m, 1H), 3.90-3.75 (m, 1H), 3.47 (m, 1H), 2.42 (dd, J=15, 11 Hz, 1H), 2.31-2.19 (m, 3H), 2.19-2.12 (m, 2H), 2.10-2.03 (m, 1H), 2.02-1.89 (m, 2H), 1.87-1.71 (m, 4H), 1.70-1.65 (m, 2H), 1.65-1.55 (m, 2H), 1.54-1.37 (m, 4H), 1.33-1.16 (m, 6H), 1.15-1.07 (s, 3H), 1.07-0.98 (m, 4H), 1.00 (s, 1H) 0.85 (m, 10H), 0.04 (s, 6H); 13C NMR (500 MHz, CDCl3) δ 210.90, 141.29, 120.81, 116.92, 72.28, 65.59, 65.02, 57.73, 50.83, 49.96, 42.77, 38.64, 37.09, 37.04, 34.58, 31.92, 31.36, 30.79, 26.06, 20.92, 19.21, 18.37, −4.45; HRMS (m/z) calculated for C27H44O4SiNa [M+Na]+, 483.2901; found, 483.2903 (T −0.42 ppm).

12α-Hydroxy-DHEA-3β-tert-butyldimethylsilyl ether 17-ethylene ketal (Compound 34): LSelectride (6.0 ml of a 1.0 M solution in tetrahydrofuran, 6.0 mmol, 1.8 eq), was added to the ketone (1.5 g, 3.3 mmol, 1.0 eq) in THF (50 ml) at −78° C. under an N2 atmosphere for 12 h. The reaction was quenched with the addition of water (20 ml) dropwise at −78° C., allowed to warm to room temperature and then extracted with ethyl acetate (3×50 ml). The organic layer was concentrated under reduced pressure and purified by silica gel column chromatography to afford the 12α-hydroxylated compound (34) as a white waxy solid (1.20 g, 2.59 mmol, 80%); mp: 107-111° C.; Rf: 0.29 (Hexanes: Ethyl acetate, 4:1, v/v); [α]D 20+18.3° [0.03% in CHCl3]; IR (neat) 3485.67, 3209.96, 2956.47, 2926.19, 2887.82, 2854.42, 1470.61, 1460.75, 1404.53, 1380.79, 1279.49, 1249.29, 1181.18, 1154.53, 1085.57, 1042.45, 1007.23, 1029.96 cm−1; 1H NMR (500 MHz, CDCl3) 5.32 (d, J=6 Hz, 1H), 4.70 (s, 1H), 4.05-3.84 (m, 5H), 3.47 (m, 1H), 2.29-2.21 (m, 1H), 2.19-2.08 (m, 2H), 2.06-1.98 (m, 1H), 1.96-1.87 (m, 1H), 1.86-1.63 (m, 6H), 1.62-1.46 (m, 4H), 1.38-1.23 (m, 2H), 1.12 (td, J=13, 3 Hz, 1H), 0.99 (s, 3H), 0.88 (s, 9H), 0.85 (s, 3H), 0.05 (s, 6H); 13C NMR (500 MHz, CDCl3) δ 141.88, 121.73, 120.94, 72.72, 71.79, 64.87, 63.53, 43.76, 43.18, 43.00, 42.61, 37.33, 36.52, 34.97, 32.76, 32.18, 39.49, 28.17, 26.08, 22.77, 19.41, 18.40, 15.71, 1.16, −4.43; HRMS (m/z) calculated for C27H46O4SiNa [M+Na]+, 485.3058; found, 485.3051 (T 1.33 ppm).

12α-Hydroxy-DHEA (Compound 17B): Hydrochloric acid (4.0 ml of a 2.0 M solution, 8.0 mmol, 37 mol eq) was added to a solution of ketal 34 (100 mg, 0.22 mmol, 1.0 eq) in THF (10 ml). The reaction was stirred for 4 h and quenched with saturated NaHCO3 (aqueous) and extracted with CH2Cl2 (50 ml). The CH2Cl2 extract was concentrated under reduced pressure and purified by silica gel column chromatography (70% hexanes to 50% hexanes in ethyl acetate) to afford the diol as a white solid (45 mg, 0.15 mmol, 68%); mp: 170-174° C.; Rf: 0.17 (hexanes: ethyl acetate, 1:1, v/v); [α]D 20 −50° [0.03% in CHCl3]; IR (neat) 3446.37, 3350.12, 2963.99, 2933.57, 2885.49, 1724.51, 1463.65, 1431.58, 1406.30, 1375.51, 1357.81, 1309.33, 1259.72, 1191.52, 1132.46, 1089.15, 1054.47, 1037.11, 1024.17, 1007.20 cm−1; 1H NMR (500 MHz, CDCl3) 5.39 (d, J=6 Hz, 1H), 4.14 (s, 1H), 3.52 (m, 1H), 2.45 (dd, J=19, 9 Hz, 1H), 2.36-2.28 (m, 1H), 2.27-2.18 (m, 1H), 2.15-1.93 (m, 5H), 1.87-1.35 (m, 1H), 1.17-1.08 (m, 1H), 1.00 (s, 3H), 0.99 (s, 3H), 0.96 (s, 1H), 0.87 (s, 3H); 13C NMR (500 MHz, CDCl3) 141.03, 121.11, 71.60, 69.65, 53.04, 43.37, 42.33, 37.11, 36.40, 36.26, 31.64, 31.38, 30.63, 27.41, 25.77, 21.16 19.35, 14.31, 13.86; HRMS (m/z) calculated for C19H28O3Na [M+Na]+, 327.1931; found, 327.1934 (T −0.94 ppm).

3β-,12α-Diacetoxy-DHEA (Compound 35): Acetic anhydride (10.0 ml, 106 mmol, 17.9 eq) and pyridine (1.20 ml, 14.8 mmol, 2.5 eq) were added to diol 17B (1.8 g, 5.9 mmol, 1 eq). The reaction was stirred at room temperature for 12 h. The reaction mixture was diluted with 50 ml of water and extracted with ethyl acetate (150 ml). The organic layer was concentrated under reduced pressure and purified by silica gel chromatography (90% hexanes to 70% hexanes in ethyl acetate) to afford a white solid (1.69 g, 9.12 mmol, 69%); mp: 189-192° C.; Rf: 0.29 (hexanes:ethyl acetate, 4:1, v/v); [α]D 20 −7.5° [0.2% in CHCl3]; IR (neat) 3450.22, 2960.86, 2944.30, 2905.91, 2826.58, 2249.42, 1731.33, 1556.73, 1463.17, 1438.07, 1438.07, 1373.99, 1357.81, 1239.62, 1134.04, 1114.17, 1022.49, cm−1; 1H NMR (500 MHz, CDCl3) 5.41 (d, J=1 Hz, 1H), 5.19 (s, 1H), 4.57 (m, 1H), 2.45-2.25 (m, 3H), 2.17-2.05 (m, 2H), 2.01 (s, 4H), 1.98-1.94 (s, 4H), 1.90-1.80 (m, 2H), 1.79-1.50 (m, 7H), 1.33-1.18 (m, 1H), 1.12-1.05 (td, J=14, 3 Hz, 1H), 0.98 (s, 3H), 0.90 (s, 3H); 13C NMR (500 MHz, CDCl3) 216.69, 170.60, 170.20, 139.97, 121.94, 73.66, 71.77, 50.70, 45.48, 44.84, 38.17, 36.95, 36.44, 36.32, 30.99, 30.64, 27.68, 25.45, 21.50, 21.36, 21.27, 19.26, 13.94; HRMS (m/z) calculated for C23H32O5Na [M+Na]+, 411.2142; found, 411.2144 (T −0.6 ppm) 3β,12α-Diacetoxy-7-oxo-DHEA (Compound 36): Chromium trioxide (1.235 g, 12.35 mmol, 6 eq) was stirred in CH2Cl2 (50 ml) at −78° C. for 15 minutes. 3,5-dimethylpyrazole (1.188 g, 12.35 mmol, 6 eq) was added to the reaction and stirred for another 20 minutes. The diacetate (0.600 g, 2.059 mmol, 1 eq) in CH2Cl2 (10 ml) was added to the mixture and stirred for 24 h. The mixture was concentrated under reduced pressure to obtain a crude black mixture which was bounded to silica gel and introduced onto an already packed silica gel column and purified (80% hexanes to 50% hexanes in ethyl acetate) to afford a white solid (0.370 g, 0.919 mmol, 45%); mp: 169-172° C.; Rf: 0.48 (hexanes:ethyl acetate, 1:1, v/v); [α]D 20+3.57° [0.28% in CHCl3]; IR (neat) 3450.95, 3348.12, 2943.86, 2935.27, 1736.78, 1668.34, 1468.59, 1439.60, 1375.50, 1364.22, 1229.63, 1134.41, 1035.68, 1025.14, cm−1; 1H NMR (500 MHz, CDCl3) 5.78 (s, 1H), 5.18 (s, 1H), 4.7 (m, 1H), 2.87 (m, 1H), 2.61 (m, 1H), 2.52-2.38 (s, 3H), 2.37-2.30 (td, J=12, 7, 1H), 2.20-2.10 (m, 2H), 2.04 (s, 3H), 2.03-1.97 (m, 1H), 1.98-1.94 (s, 4H), 1.94-1.79 (m, 3H), 1.78-1.70 (m, 2H), 1.70-1.62 (m, 1H), 1.61 (s, 2H), 1.22-1.17 (m, 4H), 0.91 (s, 3H); 13C NMR (500 MHz, CDCl3), 215.98, 200.37, 170.39, 170.16, 164.99, 126.68, 71.94, 70.71, 51.08, 45.14, 43.86, 38.19, 38.01, 36.11, 36.07, 27.32, 25.60, 23.63, 21.35, 21.21, 17.33, 14.10; HRMS (m/z) calculated for C23H31O6 [M+H]+, 403.2115; found, 403.2115 (T 0.16 ppm).

3β,12α-Dihydroxy-7-oxo-DHEA (Compound 18B): To a stirring solution of ketone 36 (0.35 g, 0.87 mmol, 1 eq) in methanol (30 ml) was added potassium carbonate (120 mg, 0.87 mmol, 1 eq). The reaction was stirred at room temperature for 24 h. The resulting reaction was diluted with water (30 ml) and extracted with ethyl acetate (100 ml). The ethyl acetate extract was concentrated under reduced pressure and then purified by silica gel column chromatography (50% hexanes to 100% ethyl acetate) to afford 12α-hydroxy-7-oxo DHEA (18B) as a pale yellow solid (60 mg, 0.19 mmol, 22%); mp: 178-181° C.; Rf: 0.78 (ethyl acetate: methanol, 4:1, v/v); [α]D 20 −8.33° [0.18% in CHCl3]; IR (neat) 3619.00, 3357.93, 3296.12, 3296.12, 3131.07, 3109.09, 3035.64, 2979.73, 2938.52, 2875.31, 2846.05, 1738.61, 1722.26, 1670.31, 1654.82, 1627.01, 1442.62, 1434.02, 1382.14, 1328.99, 1297.17, 1258.99, 1186.50, 1164.83, 1050.61, 1037.49, 1028.92, cm−1; 1H NMR (500 MHz, CDCl3) 5.75 (s, 1H), 4.12 (s, 1H), 3.68 (m, 1H), 2.81 (m, 1H), 2.58-2.50 (m, 1H), 2.48-2.34 (m, 4H), 2.17-2.06 (m, 2H), 2.06-1.96 (m, 2H), 1.96-1.87 (m, 3H), 1.85-1.76 (m, 3H), 1.76-1.68 (m, 2H), 1.66-1.58 (m, 2H), 1.32-1.22 (m, 2H), 1.18 (s, 3H), 0.88 (s, 3H); 13C NMR (500 MHz, CDCl3) 200.83, 166.42, 126.15, 70.21, 68.70, 53.51, 44.46, 44.06, 42.00, 38.05, 37.82, 36.21, 36.04, 31.19, 27.50, 23.42, 17.41, 13.99; HRMS (m/z) calculated for C19H27O4 [M+H]+, 319.1904; found, 319.1904 (T −0.48 ppm).

7,12-Dioxo-DHEA-3β-tert-butyldimethylsilyl ether 17-ethylene ketal (Compound 37): Chromium trioxide (0.69 g, 6.51 mmol, 6 eq) was added to a stirring solution of CH2Cl2 (50 ml) in a round bottom flask at −78° C. and left to stir for 15 minutes. 3,5-Dimethylpyrazole (0.63 g, 6.51 mmol, 6 eq) was added to the reaction and was stirred for 25 minutes. The ketone (0.50 g, 1.09 mmol, 1 eq) was dissolved in CH2Cl2 (10 ml) and added to the reaction mixture and stirred for 24 h. A crude black solution was obtained, bound to silica gel and loaded onto an already packed column and purified (hexane 100% to 80% hexanes in ethyl acetate) to afford diketone 37 as a pale yellow solid (0.46 g, 0.97 mmol, 89%); mp: 237-241° C.; Rf: 0.33 (hexanes:ethyl acetate, 4:1, v/v); [α]D 20 −22.2° [0.09% in CHCl3] IR (neat) 2977.36, 2948.37, 2929.25, 2894.92, 1737.84, 1710.55, 1655.69, 1621.96, 1470.41, 1458.15, 1428.66, 1417.83, 1382.15, 1373.73, 1354.75, 1296.51, 1257.83, 1184.39, 1168.27, 1138.89, 1099.14, 1090.54, 1035.79, 1030.28, cm−1; 1H NMR (500 MHz, CDCl3) 5.73 (s, 1H), 4.18 (m, 1H), 4.07 (m, 1H), 3.96 (m, 1H), 3.86 (m, 1H), 3.60 (m, 1H), 2.57 (m, 3H), 2.43 (d, J=8, 2 Hz, 1H), 2.31 (m, 2H), 2.01 (m, 2H), 1.80 (m, 3H), 1.72-1.56 (m, 4H), 1.23 (s, 3H), 1.19-1.09 (m, 4H), 0.88 (s, 9H), 0.06 (s, 6H); 13C NMR (500 MHz, CDCl3) 208.80, 199.01, 166.09, 126.04, 116.20, 71.04, 65.99, 65.51, 57.91, 49.83, 44.58, 44.21, 42.62, 38.27, 36.10, 34.56, 31.58, 25.94, 23.28, 18.25, 17.07, 15.48, −4.49; HRMS (m/z) calculated for C27H43O5Si [M+H]+, 475.2874; found, 475.2874 (T 0.07 ppm).

7α,12α-Dihydroxy-DHEA-3β-tert-butyldimethylsilyl ether 17-ethylene ketal (Compound 38): LSelectride (15 ml of 1.0 M solution in THF, 15 mmol, 16 eq) was added to a solution of diketone 37 (0.4613 g, 0.9717 mmol, 1 eq) in THF (30 ml) dropwise at −78° C. under an atmosphere of N2.

The reaction was stirred for 12 h and then quenched by adding water (20 ml) to reaction solution at 78° C. The mixture was warmed to room temperature and then extracted with ethyl acetate (3×50 ml). The ethyl acetate extract was concentrated under reduced pressure and purified by silica gel column chromatography (silica gel, 100% hexanes to 50% hexanes in ethyl acetate) to afford diol 38 as a white solid (0.20 g, 0.42 mmol, 42%); mp: 174-178° C.; Rf: 0.11[α]D 20+3.5° [0.14% in CHCl3] (hexanes:ethyl acetate, 4:1, v/v); IR (neat) 3578.41, 3416.56, 3357.55, 3207.67, 2953.08, 2953.08, 2930.93, 2883.81, 2854.33, 2260.15, 1670.03, 1629.45, 1470.72, 1416.44, 1307.65, 1282.04, 1229.08, 1193.51, 1166.41, 1118.48, 1101.42, 1042.51, 1007.59 cm−1; 1H NMR (500 MHz, CDCl3) 5.59 (dd, J=5, 2 Hz, 1H), 4.77 (d, J=2 Hz, 1H), 4.03-3.98 (m, 2H), 3.97-3.84 (m, 2H), 3.53 (m, 1H), 2.63 (td, J=11, 7 Hz, 1H), 2.33-2.26 (m, 1H), 2.24-2.18 (m, 1H), 1.97-1.89 (m, 2H), 1.88-1.83 (m, 1H), 1.82-1.65 (m, 6H), 1.63-1.57 (m, 2H), 1.56-1.42 (m, 2H), 1.41-1.29 (m, 2H), 1.26-1.17 (m, 1H), 1.17-1.09 (td, J=13, 4 Hz, 1H), 0.97 (s, 4H), 0.92 (t, J=7 Hz, 1H), 0.88 (s, 9H), 0.86 (s, 3H) 0.05 (s, 6H); 13C NMR (500 MHz, CDCl3) 147.14, 123.59, 121.56, 72.21, 71.46, 65.01, 64.87, 63.51, 47.39, 42.73, 38.48, 37.36, 37.05, 36.85, 36.33, 34.87 31.91, 27.80, 26.03, 22.71, 18.33, 18.18, 15.53, −4.44, −4.46; HRMS (m/z) calculated for C27H46O5SiNa [M+Na]+, 501.3007; found, 501.2999 (T 1.64 ppm).

7α-,12α-Dihydroxy DHEA (Compound 19B): To the diol 38 (0.20 g, 0.42 mmol, 1 eq) in THF (50 ml) was added dilute HCl (2.0 M, 10 ml in 40 ml of water, 20 mmol, 48 eq) and was stirred for 12 h. The solution was quenched with saturated NaHCO3 and extracted with CH2Cl2 (50 ml). The CH2Cl2 layer was concentrated under reduced pressure and then purified by silica gel column chromatography (100% ethyl acetate to 20% methanol in ethyl acetate) to afford 7α-,12α-dihydroxy DHEA (19B) as a white solid (55 mg, 0.17 mmol, 41%) and 7β-,12α-dihydroxy DHEA (20B) as a white solid (5 mg, 0.015 mmol, 3.57%)*; mp of Compound 19B: 182-185° C.; Rf of Compound 19B: 0.64 (ethyl acetate:methanol, 4:1, v/v) and 0.58 (ethyl acetate:methanol, 95:5, v/v); Rf of Compound 20B: 0.65 (ethyl acetate: methanol, 95:5, v/v); [α]D 20 of Compound 19B: −14.28° [0.07% in CHCl3]; IR of 19B: (neat) 3529.25, 3400.97, 3327.91, 3247.75, 2956.64, 2930.31, 2916.06, 2901.19, 2856.06, 1727.94, 1682.69, 1660.17, 1646.95, 1563.35, 1442.02, 1400.44, 1376.85, 1338.38, 1272.60, 1225.54, 1190.00, 1170.52, 1054.59, 1038.17, 1022.50, 1000.76 cm−1; 1H NMR (500 MHz, CDCl3) 5.67 (d, J=6 Hz, 1H), 4.14 (apparent s, 1H), 3.98 (apparent s, 1H) 3.58 (m, 1H), 2.58-2.51 (apparent td, J=11, 5 Hz, 1H), 2.50-2.42 (m, 1H), 2.40-2.39 (m, 1H), 2.33-2.26 (m, 1H), 2.20-2.11 (m, 2H), 2.05-1.99 (d, J=18 Hz, 2H), 1.90-1.84 (m, 2H), 1.83-1.76 (m, 2H), 1.75-1.68 (m, 2H), 1.66-1.63 (m, 3H), 1.62-1.47 (m, 13H), 1.25 (s, 3H), 1.20-1.11 (td, J=14, 3, 1H), 0.99 (s, 3H), 0.89 (s, 3H); 13C NMR (500 MHz, CDCl3) 146.49, 123.92, 71.30, 69.45, 64.48, 52.71, 42.07, 37.93, 37.30, 37.16, 36.92, 36.90, 36.16 31.40, 27.11, 21.19, 18.24, 13.74; HRMS (m/z) calculated for C19H28O4Na [M+Na]+, 343.1880; found, 343.1881 (T −0.31 ppm). *The minor 7β-hydroxy product (Compound 20B, 7β-,12α-dihydroxy DHEA) presumably arose from the LSelectride step in the reduction of diketone 38 to diol 37, (see above) 12β-Acetoxy-DHEA-3β-tert-butyldimethylsilyl ether 17-ethylene ketal (Compound 39): To a solution alcohol (1.25 g, 2.70 mmol, 1 eq) in acetic anhydride (15 ml, 157 mmol, 58 eq) was added pyridine (1.00 ml, 12.4 mmol, 4.59 eq). The reaction was stirred at room temperature for 24 h. The reaction mixture was diluted with water (50 ml) and extracted with ethyl acetate (3×50 ml). The ethyl acetate layer was concentrated under reduced pressure to produce a crude brown oil which was further purified by silica gel column chromatography (100% hexanes to 80% hexanes in ethyl acetate) to afford acetate 39 as a yellow oil (0.64 g, 1.26 mmol, 47%); Rf: 0.59 (hexanes:ethyl acetate, 4:1, v/v); [α]D 20 −12.6° [0.2% in CHCl3]; IR (neat) 2951.91, 2928.59, 2892.49, 1732.37, 1669.40, 1471.11, 1462.39, 1371.33, 1361.30, 1306.50, 1277.95, 1244.36, 1184.86, 1163.59, 1088.61, 1035.07, 1021.88, 1004.07 cm−1; 1H NMR (500 MHz, CDCl3) 5.29 (apparent d, J=5 Hz, 1H), 5.17 (dd, J=11, 5, Hz, 1H), 3.90-3.78 (m, 3H), 3.66-3.59 (m, 1H), 3.49-3.42 (m, 1H), 2.26-2.12 (m, 2H), 2.00 (s, 3H), 1.98-1.89 (m, 2H), 1.85 (dt, J=12, 5 Hz, 1H), 1.80-1.73 (m, 2H), 1.73-1.64 (m, 3H), 1.55-1.22 (m, 6H), 1.14-1.00 (m, 2H), 0.99 (s, 3H), 0.97 (s, 3H) 0.86 (s, 9H), 0.03 (s, 6H); 13C NMR (500 MHz, CDCl3) δ 170.51, 141.45, 120.85, 118.73, 73.88, 72.45, 64.92, 64.36, 49.80, 48.95, 48.30, 42.78, 37.38, 36.82, 34.75, 32.01, 31.36, 30.84, 26.74, 26.04, 22.13, 21.64, 19.44, 18.34, 9.90, −4.47; HRMS (m/z) calculated for C29H48O5SiNa [M+Na]+, 527.3163; found, 527.3161 (T 0.48 ppm).

12β-Acetoxy-7-oxo-DHEA-3β-tert-butyldimethylsilyl ether 17-ethylene ketal (Compound 40): Chromium trioxide (1.9 g, 19 mmol, 15 eq) was stirred in CH2Cl2 (50 ml) at −78° C. for 15 minutes. 3,5-dimethylpyrazole (1.8 g, 18.7 mmol, 15 eq) was added to the reaction and stirred for another 20 min. The acetate 39 (0.64 g, 1.26 mmol, 1 eq) in CH2Cl2 (10 ml) was added to the reaction mixture and stirred for 24 h. The mixture was concentrated under reduced pressure to obtain a crude black mixture which was bound to silica gel and dry loaded onto an already packed silica gel column and purified (hexanes 100% to 80% hexanes in ethyl acetate) to afford ketone 40 as a yellow solid (0.2664 g, 0.5140 mmol, 40%); mp: 164-167° C.; Rf: 0.22 (hexanes:ethyl acetate, 4:1, v/v); [α]D 20+7° [0.14% in CHCl3]; IR (neat) 2952.03, 2929.47, 2856.95, 1731.88, 1666.73, 1634.24, 1471.28, 1384.89, 1373.47, 1245.27, 1137.82, 1093.40, 1032.28, 1022.03, 1004.85 cm−1; 1H NMR (500 MHz, CDCl3) 5.67 (s, 1H), 5.09 (dd, J=11, 5, Hz, 1H), 3.90-3.78 (m, 3H), 3.65-3.55 (m, 2H), 2.53-2.34 (m, 3H), 2.22 (dd, J=15, 12 Hz, 1H), 2.02 (s, 3H), 1.95-1.89 (m, 2H), 1.88-1.77 (m, 4H), 1.71-1.63 (dt, J=13, 5 Hz, 1H), 1.60 (apparent s, 3H), 1.57-1.47 (m, 2H), 1.25-1.15 (m, 5H), 1.00 (s, 3H), 0.88 (s, 9H), 0.05 (s, 6H); 13C NMR (500 MHz, CDCl3) δ 200.76, 170.49, 166.19, 125.91, 117.95, 72.86, 71.23, 64.90, 64.29, 48.56, 48.53, 44.53, 44.38, 44.14, 42.64, 38.51, 36.49, 34.76, 31.70, 26.70, 25.95, 24.46, 21.58, 18.26, 9.98, −4.50, −4.55; HRMS (m/z) calculated for C29H47O6Si [M+H]+, 519.3136; found, 519.3136 (T 0.1 ppm).

12β-Acetoxy-7β-hydroxy-DHEA-3β-tert-butyldimethylsilyl ether 17-ethylene ketal (Compound 41): To a stirring solution of ketone 40 (1.5 g, 2.89 mmol, 1 eq) in methanol (50 ml) at 0° C. was added sodium borohydride powder (4.00 g, 105 mmol, 36 eq). The reaction was stirred from 0° C. to room temperature for 6 h. The solution was diluted with water (50 ml) and transferred to a separatory funnel, which was extracted with ethyl acetate (3×50 ml). The ethyl acetate layer was concentrated under reduced pressure to form crude white solid which was purified by silica gel column chromatography (100% hexanes to 70% ethyl acetate) to afford an epimeric mixture of 7α- and 7β-hydroxy products as a colorless solid (1.2 g, 2.3 mmol, 80%), which were unresolvable from TLC analysis. Based on the integration of the 5-proton in the 1H NMR spectrum, the mixture of the 7α-hydroxy and 7β-hydroxy products were in a 1:4 ratio. This ratio was determined by integrating the 5-protons of the 7α-hydroxy epimer and the 7β-hydroxy epimer (41) in the 1H NMR spectrum, which appeared at δ 5.56 ppm and 5.21 ppm, respectively.

The upfield chemical shift (δ 5.21 ppm) was assigned as the 7β-hydroxy epimer as we have done in a previous study [19]; mp: 124-129° C.; Rf: 0.45 (hexanes:ethyl acetate, 7:3, v/v); [α]D 20-17.8° [0.14% in CHCl3]; IR (neat) 3466.11, 2951.81, 2930.96, 2854.78, 1731.91, 1715.78, 1671.87, 1471.24, 1462.55, 1358.18, 1371.99, 1361.26, 1245.93, 1191.37, 1136.13, 1091.75, 1070.26, 1027.82, 1004.27 cm−1; 1H NMR (500 MHz, CDCl3) δ 5.21 (s, 1H), 5.12 (dd, J=12, 5, Hz, 1H), 3.89-3.78 (m, 3H), 3.65-3.60 (m, 1H), 3.52-3.44 (m, 1H), 2.30-2.15 (m, 2H), 2.00 (s, 3H), 1.98-1.90 (m, 2H), 1.89-1.78 (m, 2H), 1.77-1.57 (m, 5H), 1.55-1.31 (m, 5H), 1.25-1.17 (dt, J=12, 6 Hz, 1H), 1.16-1.01 (m, 4H), 0.99 (s, 3H), 0.97 (s, 1H), 0.87 (s, 9H), 0.04 (s, 6H); 13C NMR (500 MHz, CDCl3) δ 146.78, 144.07, 125.39, 123.37, 118.62, 118.25, 73.57, 73.35, 73.03, 72.13, 64.90, 64.45, 64.36, 64.32, 49.36, 48.54, 46.93, 43.33, 42.56, 42.26, 41.64, 40.12, 37.65, 37.10, 37.06, 36.81, 34.88, 34.72, 31.96, 31.77, 26.58, 26.01, 24.30, 21.61, 19.15, 18.31, 9.88, −4.47, −4.49; HRMS (m/z) calculated for C29H48O6SiNa [M+Na]+, 543.3112; found, 543.3108 (T 0.87 ppm).

12β-Acetoxy-DHEA-3β,7β-di-tert-butyldimethylsilyl ether 17-ethylene ketal (Compound 42): To the 7α*/7β-epimeric mixture of alcohol 41 (vide supra) (1.2 g, 2.3 mmol, 1 eq) in acetonitrile (50 ml) was added tert-butyldimethylsilyl chloride (3.11 g, 20.6 mmol, 9 eq) and imidazole (2.5 g, 36 mmol, 15 eq). The reaction was refluxed at 90° C. for 12 h. The reaction was diluted with water (50 ml) and extracted with ethyl acetate (150 ml). The organic layer was concentrated under reduced pressure and purified by silica gel column chromatography (hexanes 90% to 80% hexanes in ethyl acetate) to afford the TBDMS ether 42 as a white solid (0.94 g, 1.42 mmol, 60%); mp: 121-125° C.; Rf. 0.63 (hexanes:ethyl acetate, 7:3, v/v); [α]D 20 −10.86° [0.23% in CHCl3]; IR (neat) 2950.94, 2927.70, 2855.45, 1721.92, 1678.02, 1471.03, 1462.09, 1385.44, 1376.50, 1361.74, 1249.56, 1174.04, 1159.85, 1092.94, 1078.57, 1049.42, 1032.25, 1002.64 cm−1; 1H NMR (500 MHz, CDCl3) δ 5.20 (s, 1H), 5.09 (dd, J=12, 5, Hz, 1H), 3.95 (apparent d, J=8 Hz, 1H) 3.89-3.75 (m, 3H), 3.65-3.59 (m, 1H), 3.50-3.41 (m, 1H), 2.34-2.08 (m, 2H), 2.00 (s, 3H), 1.97-1.81 (m, 3H), 1.79-1.41 (m, 7H), 1.40-1.23 (m, 2H), 1.20-1.13 (td, J=11, 5 Hz, 1H), 1.10-1.01 (m, 3H), 0.97 (s, 2H), 0.94 (s, 2H), 0.90 (s, 2H), 0.88-0.83 (m, 17H), 0.08-0.01 (m, 12H); 13C NMR (500 MHz, CDCl3) δ 170.55, 144.68, 142.63, 126.09, 124.49, 118.68, 118.38, 74.41, 74.05, 73.47, 72.49, 72.11, 64.93, 64.85, 64.44, 64.29, 49.51, 48.61, 47.86, 47.10, 43.05, 43.02, 42.41, 41.22, 39.87, 37.57, 37.53, 37.28, 37.17, 36.63, 35.00, 34.88, 32.01, 31.90, 26.63, 26.48, 26.35, 26.07, 26.04, 26.01, 25.77, 24.69, 22.12, 21.68, 21.62, 18.96, 18.41, 18.34, 18.29, 9.91, 9.73, −2.46, −3.21, −3.23, −3.44, −4.27, −4.45, −4.46, −4.59; HRMS (m/z) calculated for C35H62O6Si2Na [M+Na]+, 657.3977; found, 657.3985 (T −1.17 ppm). *The minor 7α-OTBDMS epimer product was observed through 1H NMR spectroscopy (δ 5.45 (d, J=6 Hz, 1H), which corresponds to the 5 proton), however over the sequence of the next four synthetic steps toward 7β-,12α-dihydroxy-DHEA (Compound 20B), the amount of the 7α-hydroxy epimer decreases relative to the 7β-hydroxy epimer.

12β-Hydroxy-DHEA-3β,7β-di-tert-butyldimethylsilyl ether 17-ethylene ketal (Compound 43): Potassium carbonate (2.0 g, 14 mmol, 10 eq) was added to acetate 41 (0.90 g, 1.41 mmol, 1 eq) in methanol (50 ml). The reaction was refluxed at 60° C. for 6 h. The solution was cooled to room temperature and diluted with water (50 ml) and extracted with ethyl acetate (150 ml). The ethyl acetate extract was concentrated under reduced pressure and purified by silica gel column chromatography (hexanes 100% to 80% hexanes in ethyl acetate) to afford the 12β alcohol 43 as a white solid (0.643 g, 1.08 mmol, 75%); mp: 126-130° C.; Rf. 0.375 (hexanes:ethyl acetate, 4:1, v/v); [α]D 20+7.5° [0.2% in CHCl3] IR (neat), 3592.56, 3516.69, 2950.77, 2928.91, 2884.30, 2854.88, 1470.80, 1462.41, 1436.18, 1385.81, 1360.65, 1276.37, 1248.73, 1160.60, 1128.81, 1092.21, 1069.31, 1051.75, 1035.04, 1000.13 cm−1; 1H NMR (500 MHz, CDCl3) δ 5.21 (s, 1H), 4.04-3.90 (m, 5H), 3.89-3.82 (m, 1H), 3.47 (m, 1H), 2.33-2.20 (m, 1H), 2.19-2.08 (m, 1H), 1.94-1.83 (m, 2H), 1.83-1.63 (m, 7H), 1.57-1.44 (m, 3H), 1.44-1.31 (m, 2H), 1.16-1.08 (m, 1H), 1.08-1.02 (s, 3H), 1.02-0.94 (m, 2H), 0.92 (s, 2H), 0.87 (s, 9H), 0.87 (s, 7H), 0.84 (s, 2H), 0.05 (m, 12H)); 13C NMR (500 MHz, CDCl3) δ 144.88, 142.79, 126.10, 124.47, 119.16, 118.94, 74.70, 77.58, 77.23, 71.33, 70.05, 65.04, 64.56, 64.15, 49.02, 48.89, 48.34, 47.32, 43.05, 42.46, 41.47, 39.91, 37.60, 37.55, 37.35, 37.25, 36.69, 34.02, 33.84, 32.13, 32.07, 29.20, 26.38, 26.02, 25.10, 22.47, 19.07, 18.43, 18.35, 9.02, 8.80, −2.47, −3.08, −3.22, −4.30,−4.43, −4.58; HRMS (m/z) calculated for C33H60O5Si2Na [M+Na]+, 615.3871; found, 615.3855 (T 2.75 ppm). The minor 7α-OTBDMS epimer was observed by 1H NMR spectroscopy (δ 5.46 (d, J=6 Hz, 1H), see experimental for Compound 42).

12-Oxo-DHEA-3β,7β-di-tert-butyldimethylsilyl ether 17-ethylene ketal (Compound 44): Pyridinium chlorochromate (0.25 g, 1.16 mmol, 2.16 eq) was added to a solution of the alcohol (0.319 g, 0.538 mmol, 1 eq) in CH2Cl2 (50 ml). The solution was stirred at room temperature for 8 h. The reaction mixture was washed with 5% NaOH (aqueous, 3×50 ml, w/v) using a separatory funnel and then concentrated under reduced pressure to obtain a crude yellow solid residue. The crude residue was purified by silica gel column chromatography (100% hexanes to 90% hexanes in ethyl acetate) to afford the ketone 44 as a white solid (0.157 g, 0.266 mmol, 49%); mp: 71-75° C.; Rf. 0.83 (hexanes:ethyl acetate, 4:1, v/v); [α]D20 −38.4° [0.05% in CHCl3]; IR (neat) δ 2951.39, 2928.74, 2891.79, 2854.65, 1713.00, 1470.80, 1462.63, 1385.07, 1360.19, 1275.17, 1249.39, 1163.10, 1091.89, 1073.71, 1061.62, 1034.85, 1004.05 cm−1; 1H NMR (500 MHz, CDCl3) δ 5.26 (s, 1H), 4.24-4.13 (m, 1H), 4.11-4.04 (m, 2H); 4.02-3.91 (m, 1H), 3.88-3.81 (m, 1H), 3.51-3.44 (m, 1H), 2.45-2.36 (m, 1H), 2.31-2.19 (m, 3H), 2.11-2.02 (m, 1H), 2.02-1.88 (m, 2H), 1.86-1.63 (m, 5H), 1.62 (s, 1H), 1.58-1.44 (m, 2H), 1.11 (s, 3H), 1.08 (s, 3H), 1.06-0.92 (m, 3H), 0.88 (apparent d, 18H), 0.84 (s, 1H), 0.11-0.02 (m, 12H); 13C NMR (500 MHz, CDCl3) δ 210.60, 142.47, 126.07, 116.61, 74.10, 71.93, 65.98, 65.52, 57.88, 49.57, 48.73, 42.40, 39.82, 38.43, 36.88, 36.78, 34.69, 31.91, 26.39, 26.01, 23.29, 18.59, 18.33, 18.28, 15.34, −2.44, −3.21, −4.43, −4.45; HRMS (m/z) calculated for C33H58O5Si2Na [M+Na]+, 613.3715; found, 613.3721 (T −0.97 ppm). The minor 7α-OTBDMS epimer was observed by 1H NMR spectroscopy (δ 5.51 (d, J=6 Hz, 1H), see experimental for Compound 42).

12α-Hydroxy-DHEA-3β,7β-di-tert-butyldimethylsilyl ether 17-ethylene ketal (Compound 45): To a stirring solution of ketone 44 (0.1573 g, 0.266 mmol, 1 eq) in THF (50 ml) at −78° C. under an atmosphere of N2, L-Selectride (8 ml of a 1.0 M solution in THF) was added via a syringe dropwise. The reaction was stirred for 12 h and then quenched with the slow addition of water (20 ml) at −78° C. The resulting solution was extracted with ethyl acetate (150 ml) and the ethyl acetate extract was concentrated under reduced pressure, purified by silica gel column chromatography (hexanes 100% to 80% hexanes in ethyl acetate) to afford the 12a alcohol 45 as a white solid (0.103 g, 0.174 mmol, 65%); mp: 118-121° C.; Rf. 0.45 (Hexanes: Ethyl acetate, 4:1, v/v); [α]D 20 0° [0.10% in CHCl3] IR (neat) δ 3501.97, 3459.13, 3214.33, 2949.55, 2927.31, 2895.49, 2854.47, 1672.44, 1470.20, 1461.30, 1385.02, 1360.37, 1280.85, 1249.53, 1180.10, 1074.60, 1053.57, 1024.36, 1004.78 cm−1; 1H NMR (500 MHz, CDCl3) δ 5.22 (s, 1H), 4.72 (s, 1H), 4.08 (apparent d, J=6 Hz, 1H); 4.02-3.97 (m, 1H), 3.97-3.86 (m, 4H), 3.51-3.42 (m, 1H), 2.29-2.16 (m, 2H), 2.15-2.09 (m, 1H), 2.06-1.97 (m, 1H), 1.93-1.85 (m, 1H), 1.80-1.69 (m, 3H), 1.68-1.46 (m, 7H), 1.35-1.19 (m, 1H), 1.10-0.99 (m, 4H), 0.88 (apparent d, 19H), 0.84 (s, 3H), 0.11-0.03 (m, 12H); 13C NMR (500 MHz, CDCl3) δ 143.01, 126.27, 121.32, 75.33, 72.43, 71.60, 64.81, 63.50, 48.12, 42.60, 42.25, 41.66, 41.26, 37.12, 36.55, 35.05, 32.18, 27.98, 26.41, 26.05, 25.48, 18.94, 18.33, 18.28, 15.88, −2.63, −3.28, −4.40, −4.42; HRMS (m/z) calculated for C33H60O5Si2Na [M+Na]+, 615.3871; found, 615.3870 (T 0.24 ppm). The minor 7α-OTBDMS epimer was observed by 1H NMR spectroscopy (δ 5.48 (d, J=6 Hz, 1H), see experimental for Compound 42).

7β-,12α-dihydroxy-DHEA (Compound 20B): To the 12α-alcohol 45 (0.278 g, 0.468 mmol, 1 eq) in THF (50 ml) was added dilute HCl (2M, 10 ml in 40 ml of water, 20 mmol, 43 eq). The reaction was stirred for 24 h and then quenched with saturated NaHCO3 (aqueous). The resulting solution was extracted with CH2Cl2 (100 ml) and the organic layer was concentrated under reduced pressure to give a crude colorless oil. The crude oil was purified by silica gel column chromatography (ethyl acetate 100% to 20% methanol in ethyl acetate) to afford two triol products, 7β-hydroxy as a white solid (20B, 60 mg, 0.187 mmol, 40%) as the major product Rf. 0.64 (ethyl acetate:methanol, 4:1 v/v) and the minor product, 7α-hydroxy (19B, 15 mg, 0.046 mmol, 9%) Rf. 0.58 (ethyl acetate: methanol, 4:1 v/v) as a white solid, 20B: mp: 188-192° C.; [α]D 20 −31.3° [0.02% in CHCl3]; 3542.23, 3434.50, 3239.20, 2990.33, 2947.19, 2931.57, 2857.25, 1730.46, 1688.83, 1680.83, 1465.06, 1439.21, 1391.66, 1305.75, 1261.74, 1255.16, 1236.10, 1219.66, 1196.92, 1131.53, 1082.62, 1107.25, 1059.93, 1059.93, 1054.78, 1043.50, 1005.66 cm−1; 1H NMR (500 MHz, CDCl3) 5.33 (s, 1H), 4.13 (s, 1H), 4.03 (apparent d, J=7 Hz, 1H) 3.60-3.51 (m, 1H), 2.46 (dd, J=19, 9 Hz, 1H), 2.37-2.32 (m, 1H), 2.30-2.22 (m, 1H), 2.22-2.16 (m, 1H), 2.11 (dt, J=19, 9 Hz, 1H), 1.93-1.73 (m, 5H), 1.69-1.46 (m, 8H), 1.27-1.23 (m, 1H), 1.15-1.07 (td, J=14, 5 3H), 1.05 (s, 3H), 0.89 (s, 3H); 13C NMR (500 MHz, CDCl3) δ 143.79, 125.71, 72.79, 71.37, 69.26, 53.35, 42.84, 42.76, 41.81, 40.37, 36.84, 36.46, 36.43, 31.59, 27.39, 23.45, 19.14, 13.39; HRMS (m/z) calculated for C19H28O4Na [M+Na]+, 343.1880; found, 343.1883 (T −0.93 ppm).

SUPPORTING INFORMATION NMR and IR data $^1$H and $^{13}$C NMR, HRMS, and IR spectra of Compound 29, as shown in FIGS. 24-27.

$^1$H and $^{13}$C NMR, HRMS, and IR spectra of Compound 30, as shown in FIGS. 28-31.

$^1$H and $^{13}$C NMR, HRMS, and IR spectra of Compound 31, as shown in FIGS. 32-35.

$^1$H and $^{13}$C NMR, HRMS, and IR spectra of Compound 32, as shown in FIGS. 36-39.

$^1$H and $^{13}$C NMR, HRMS, and IR spectra of Compound 33, as shown in FIGS. 40-43.

$^1$H and $^{13}$C NMR, HRMS, and IR spectra of Compound 34, as shown in FIGS. 44-47.

$^1$H and $^{13}$C NMR, HRMS, and IR spectra of Compound 17B, as shown in FIGS. 48-51.

$^1$H and $^{13}$C NMR, HRMS, and IR spectra of Compound 35, as shown in FIGS. 52-55.

$^1$H and $^{13}$C NMR, HRMS, and IR spectra of Compound 36, as shown in FIGS. 56-59.

$^1$H NMR, HRMS, and IR spectra of Compound 18B, as shown in FIGS. 60-63.

$^1$H and $^{13}$C NMR, HRMS, and IR spectra of Compound 37, as shown in FIGS. 64-67.

$^1$H and $^{13}$C NMR, HRMS, and IR spectra of Compound 38, as shown in FIGS. 68-71.

$^1$H and $^{13}$C NMR, HRMS, and IR spectra of Compound 19B, as shown in FIGS. 72-75.

$^1$H and $^{13}$C NMR, HRMS, and IR spectra of Compound 39, as shown in FIGS. 76-79.

$^1$H and $^{13}$C NMR, HRMS, and IR spectra of Compound 40, as shown in FIGS. 80-83.

$^1$H and $^{13}$C NMR, HRMS, and IR spectra of Compound 41, as shown in FIGS. 84-87.

$^1$H and $^{13}$C NMR, HRMS, and IR spectra of Compound 42, as shown in FIGS. 88-91.

$^1$H and $^{13}$C NMR, HRMS, and IR spectra of Compound 43, as shown in FIGS. 92-96.

Figure 97:
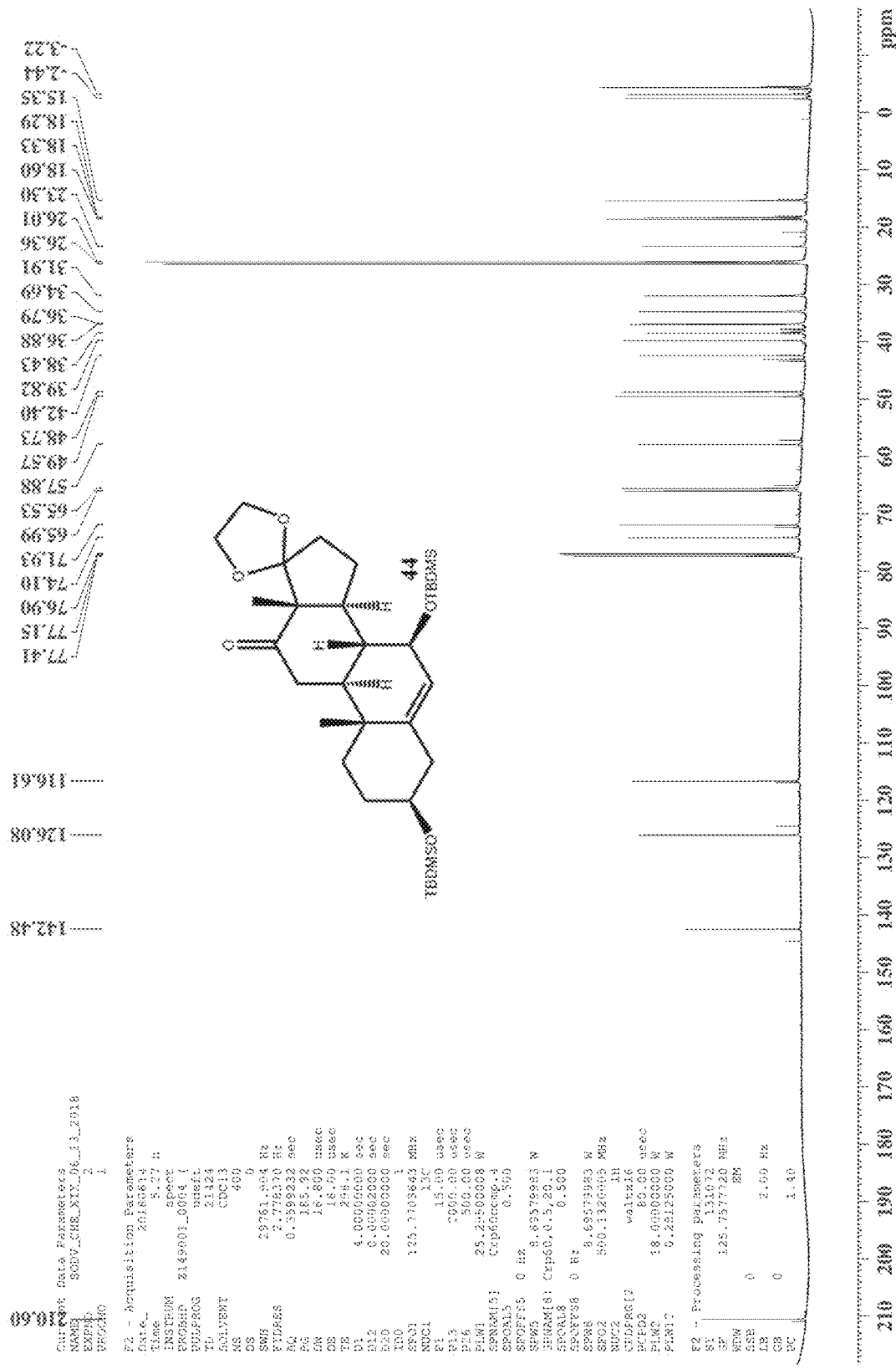
FIGS. 97-99 show $^1$H and $^{13}$C NMR, HRMS, and IR spectra of Compound 44.
Figure 98:
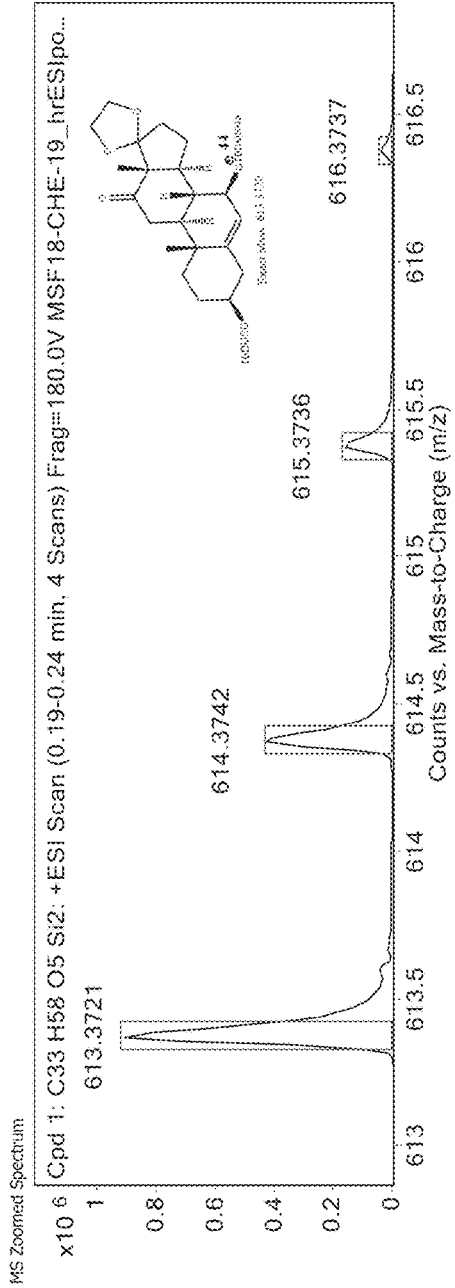
Figure 99:
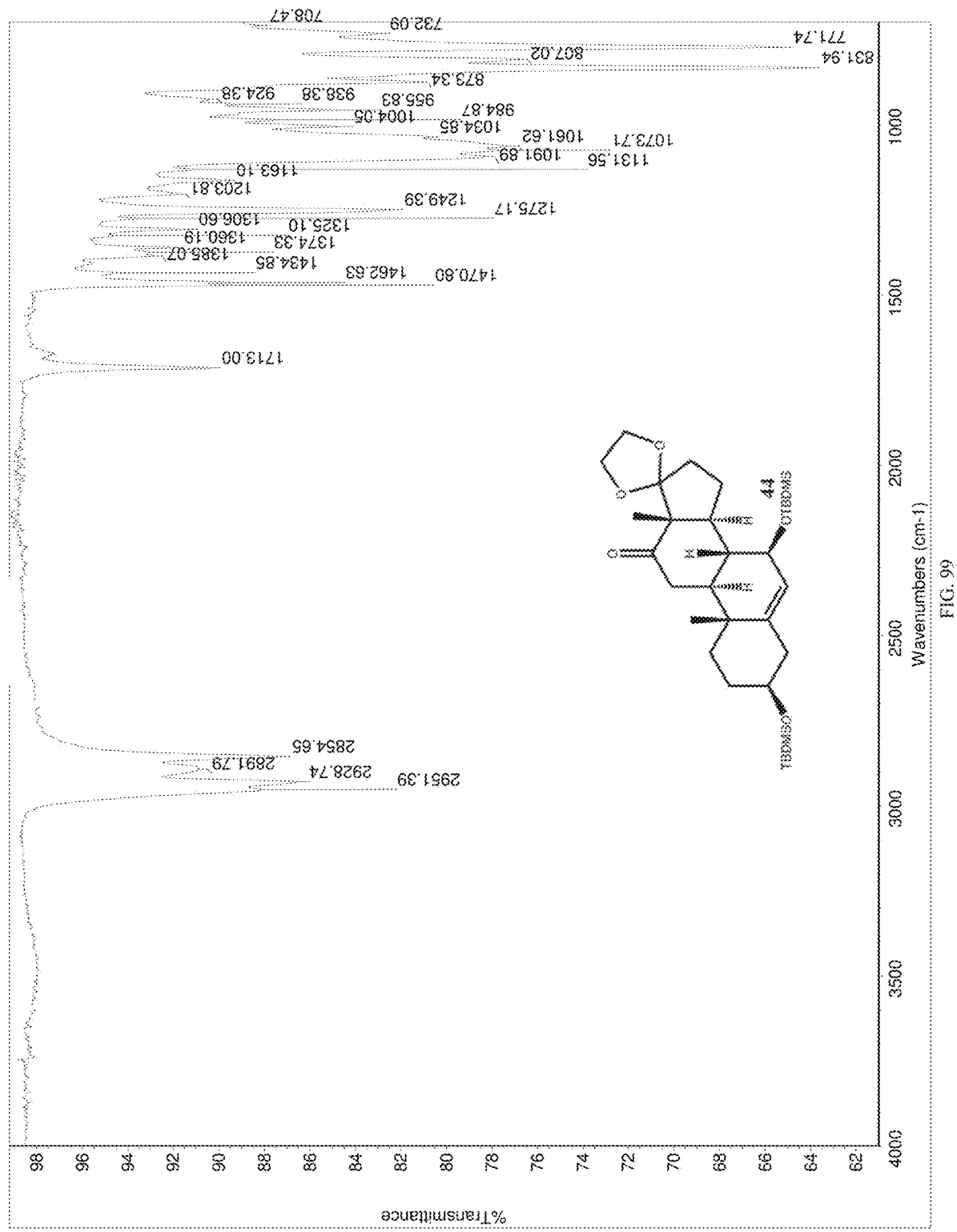
Figure 100:
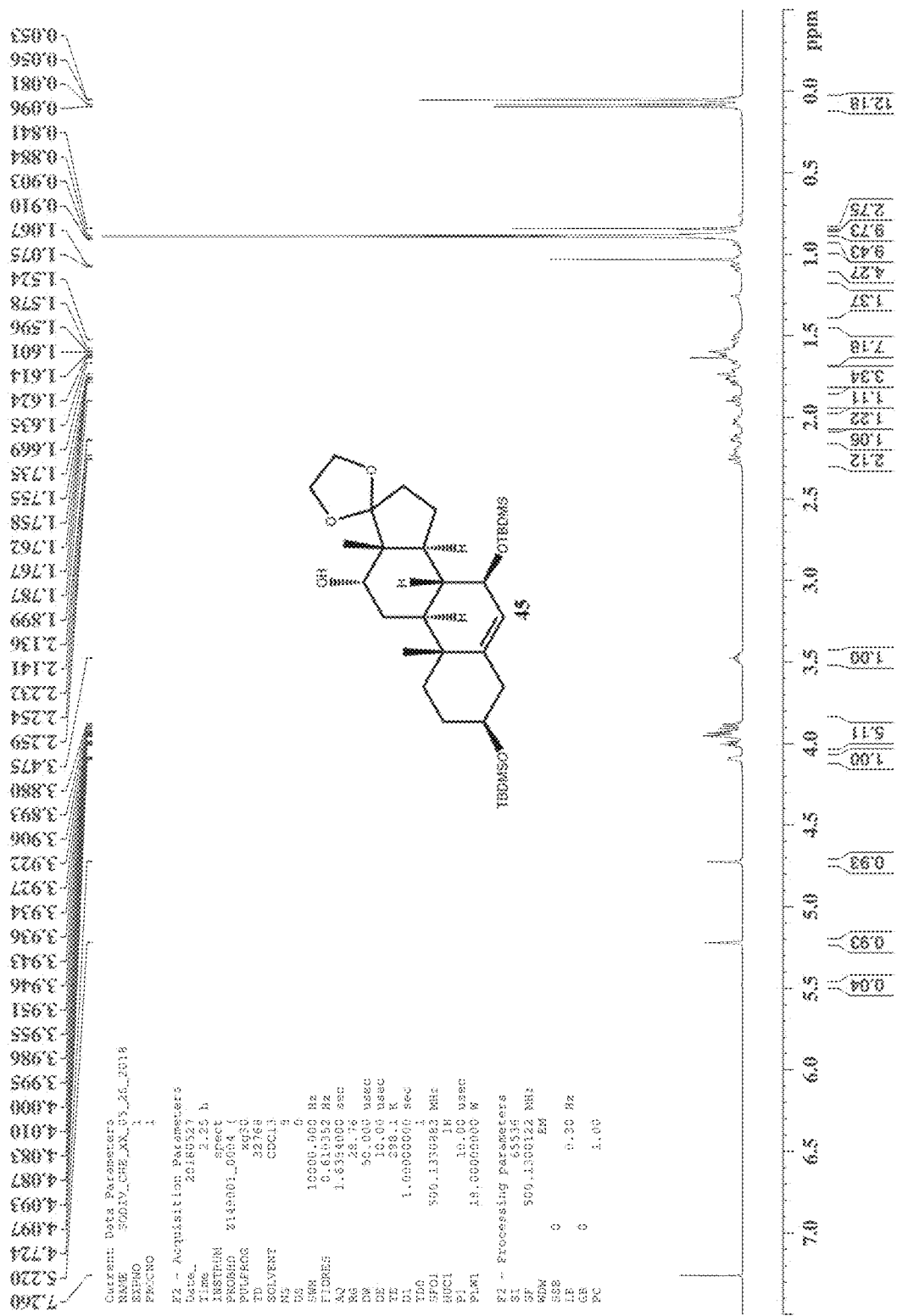
FIGS. 100-103 show $^1$H NMR, HRMS, and IR spectra of Compound 45.
Figure 101:
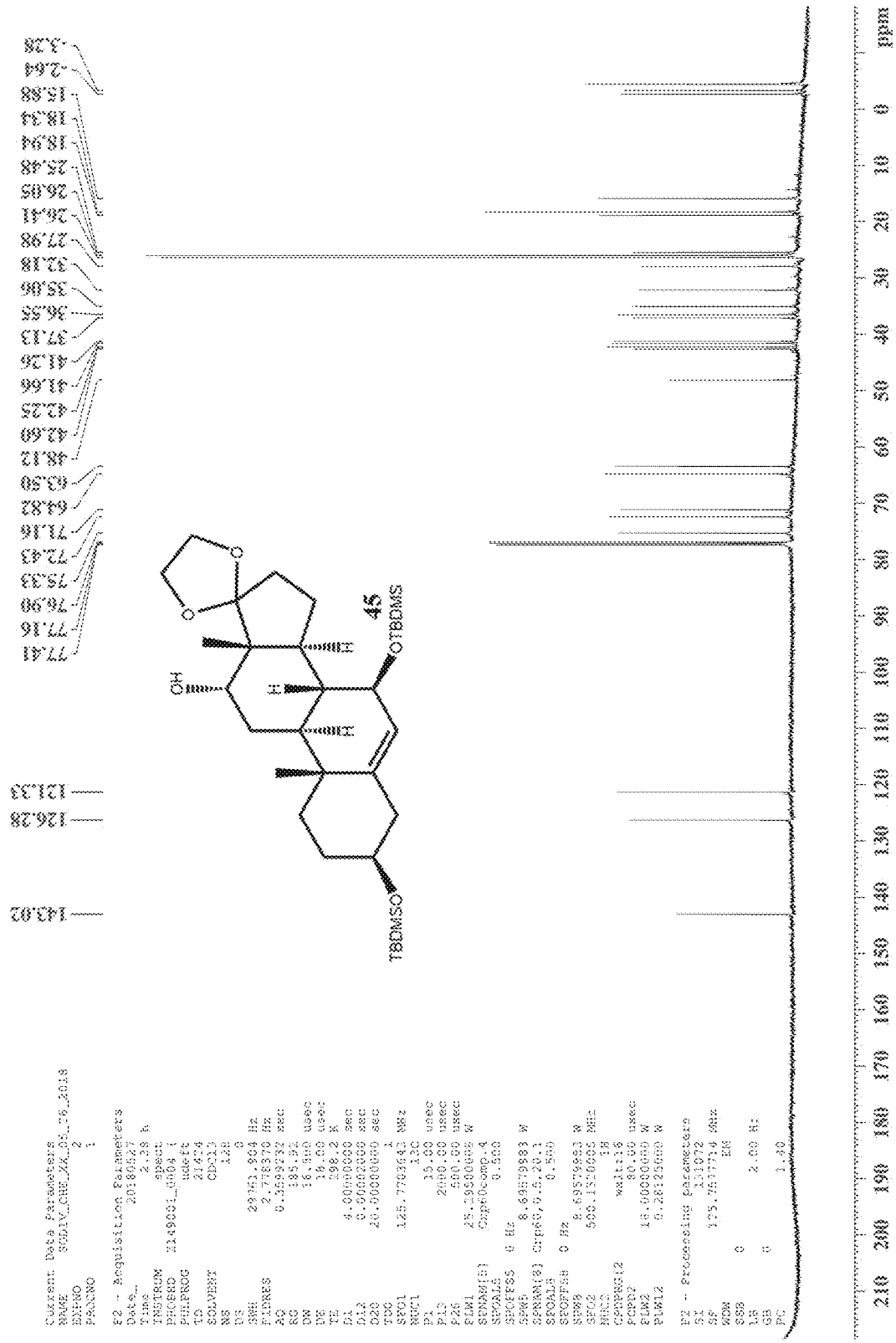
Figure 102:
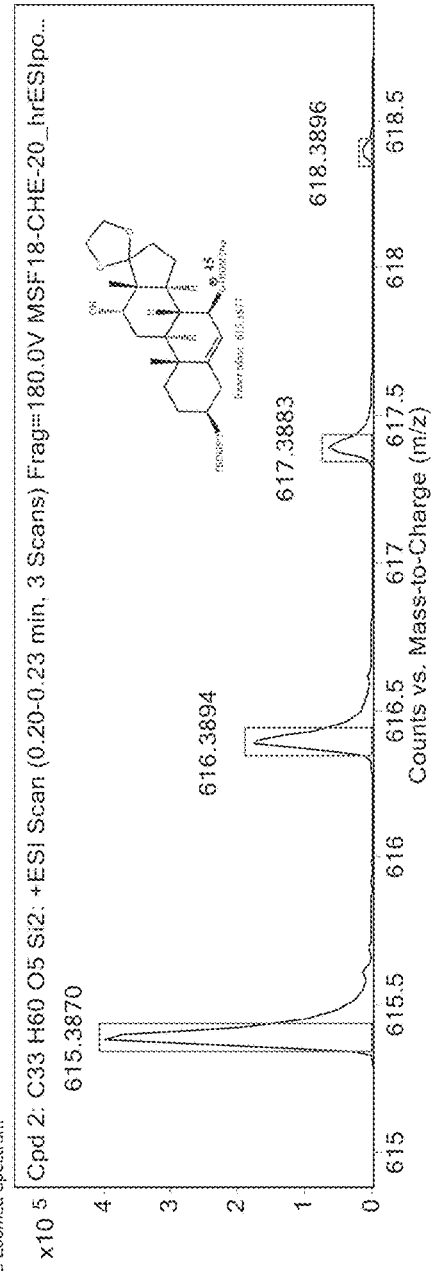
Figure 103:
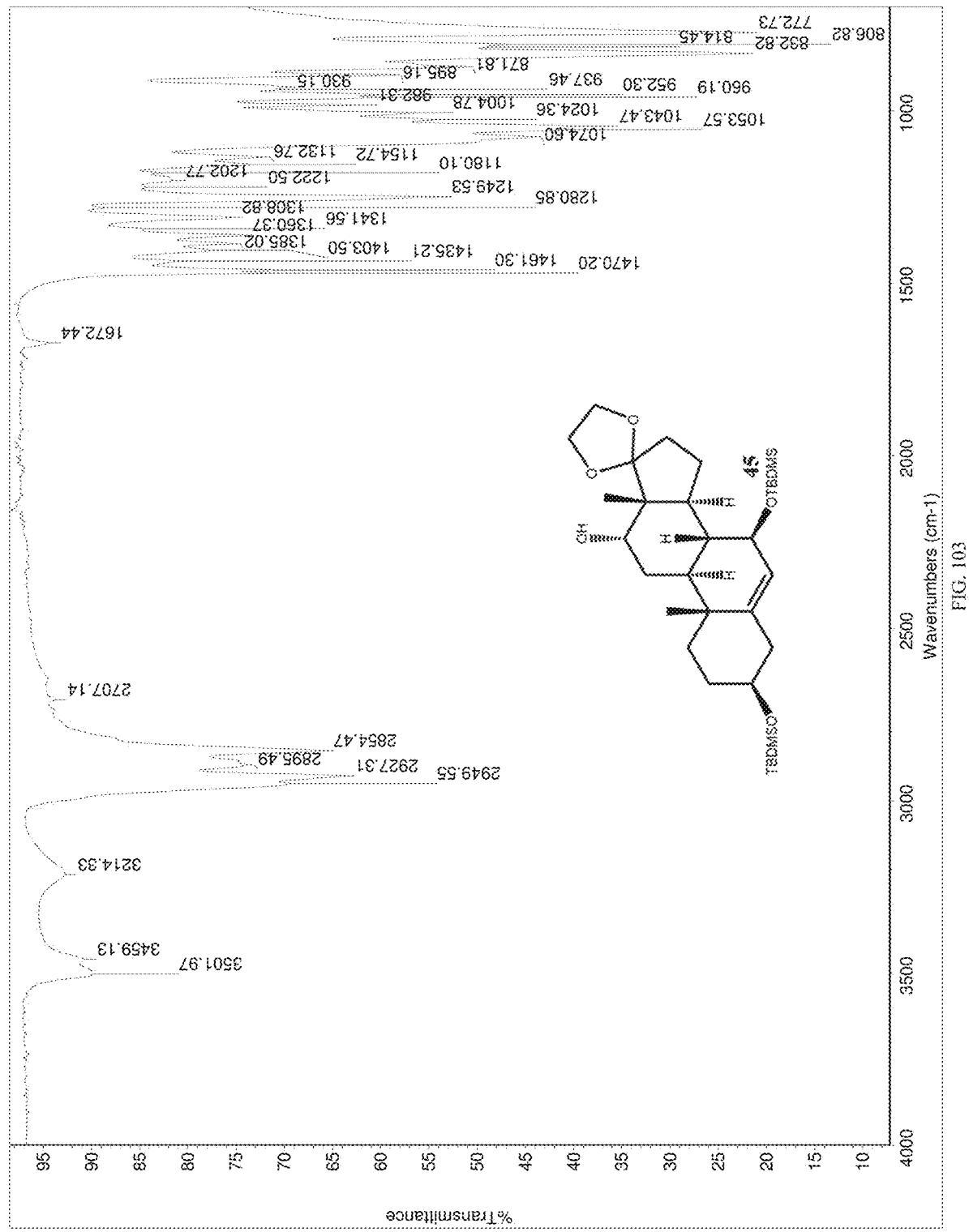
Figure 104:
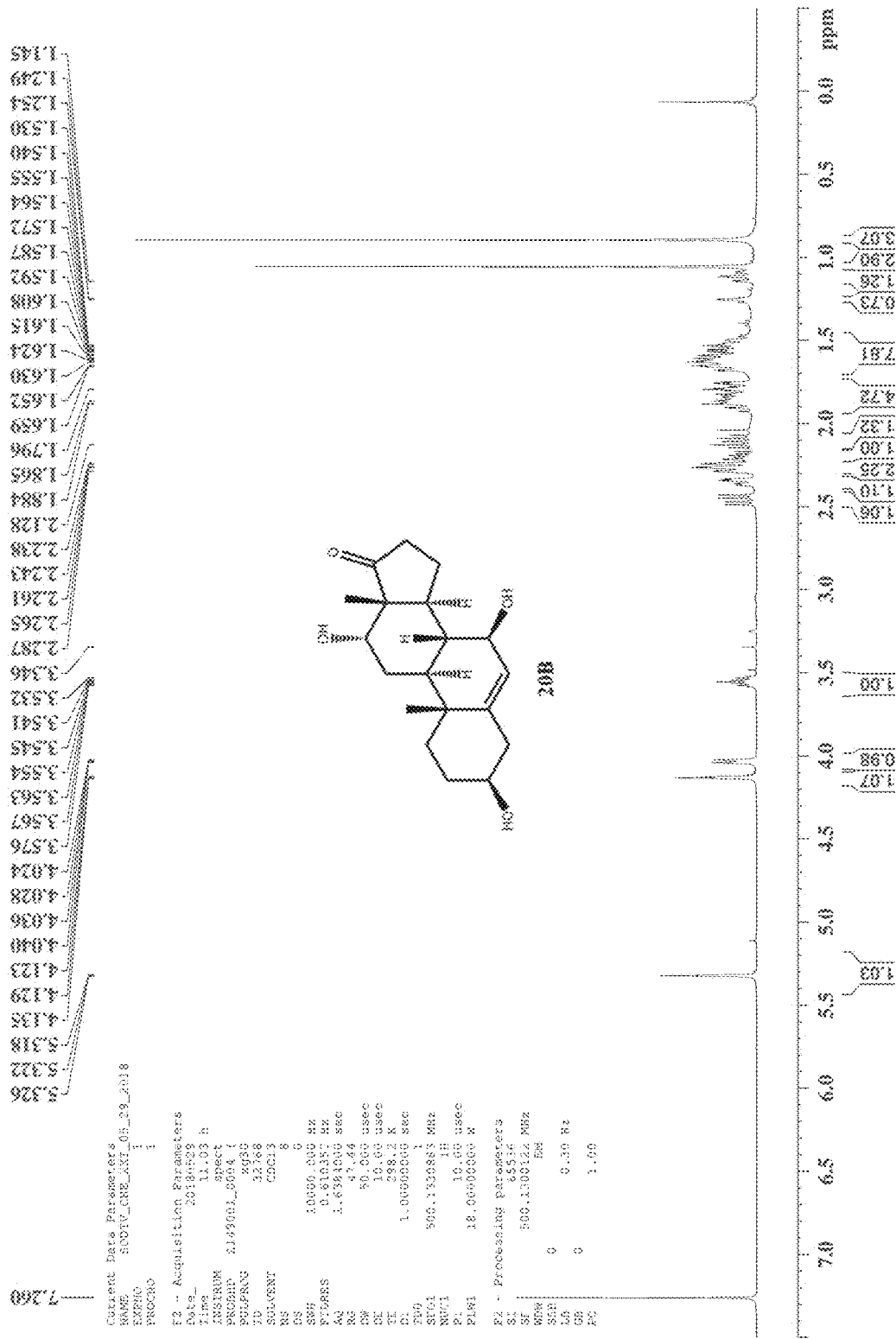
FIGS. 104-107 show $^1$H NMR, HRMS, and IR spectra of Compound 20B.
Figure 105:
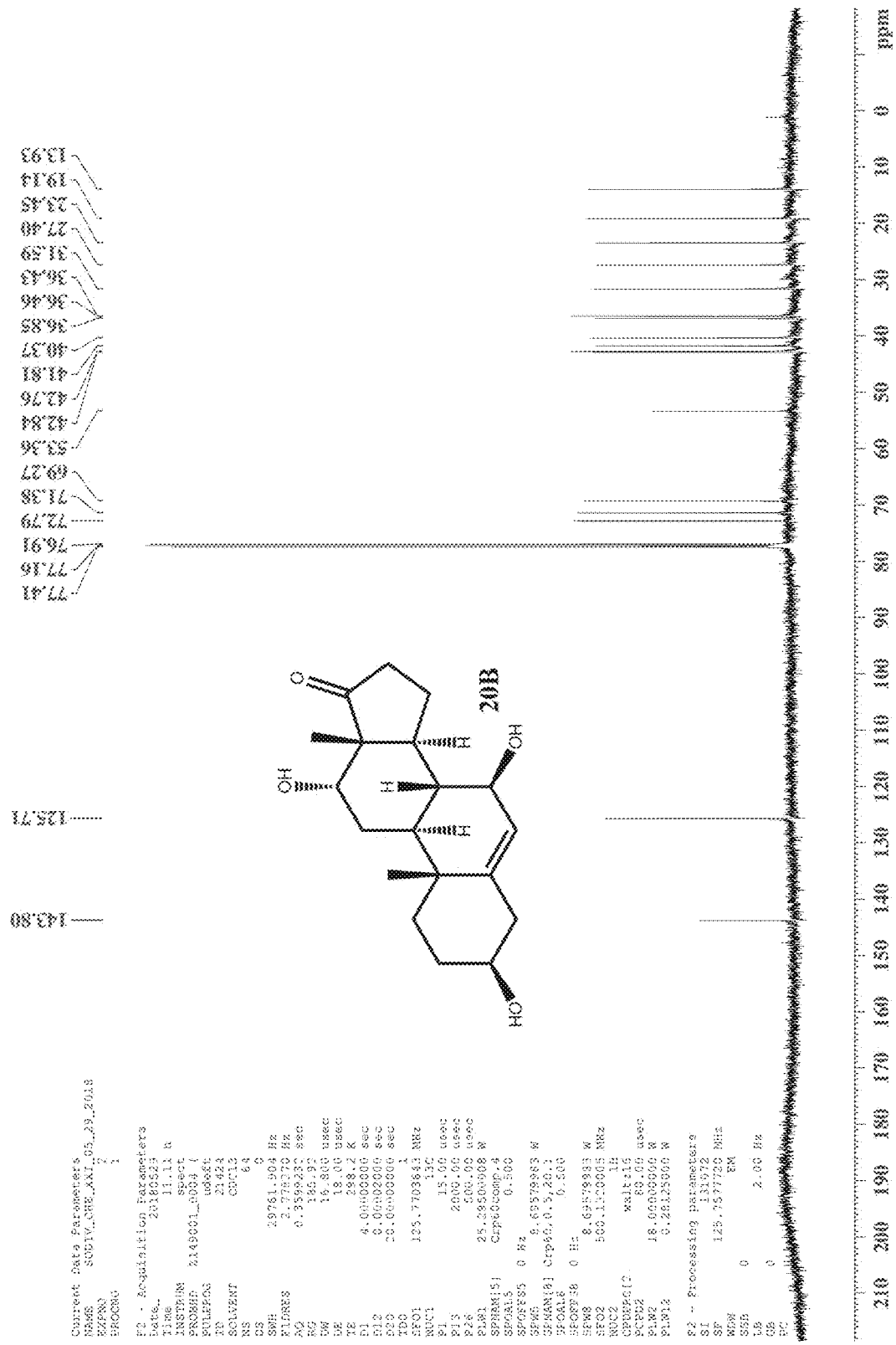
Figure 106:
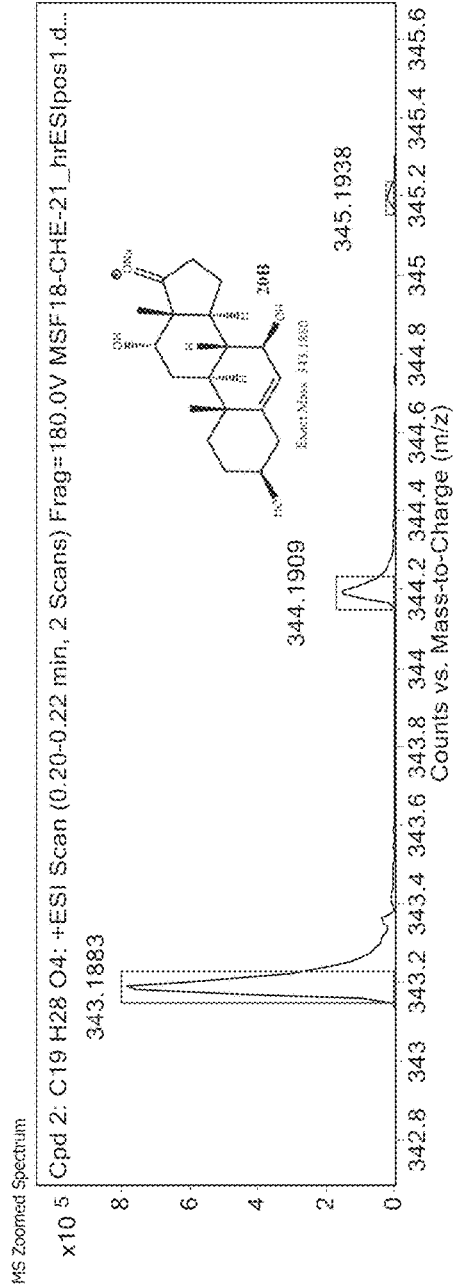
Figure 107:
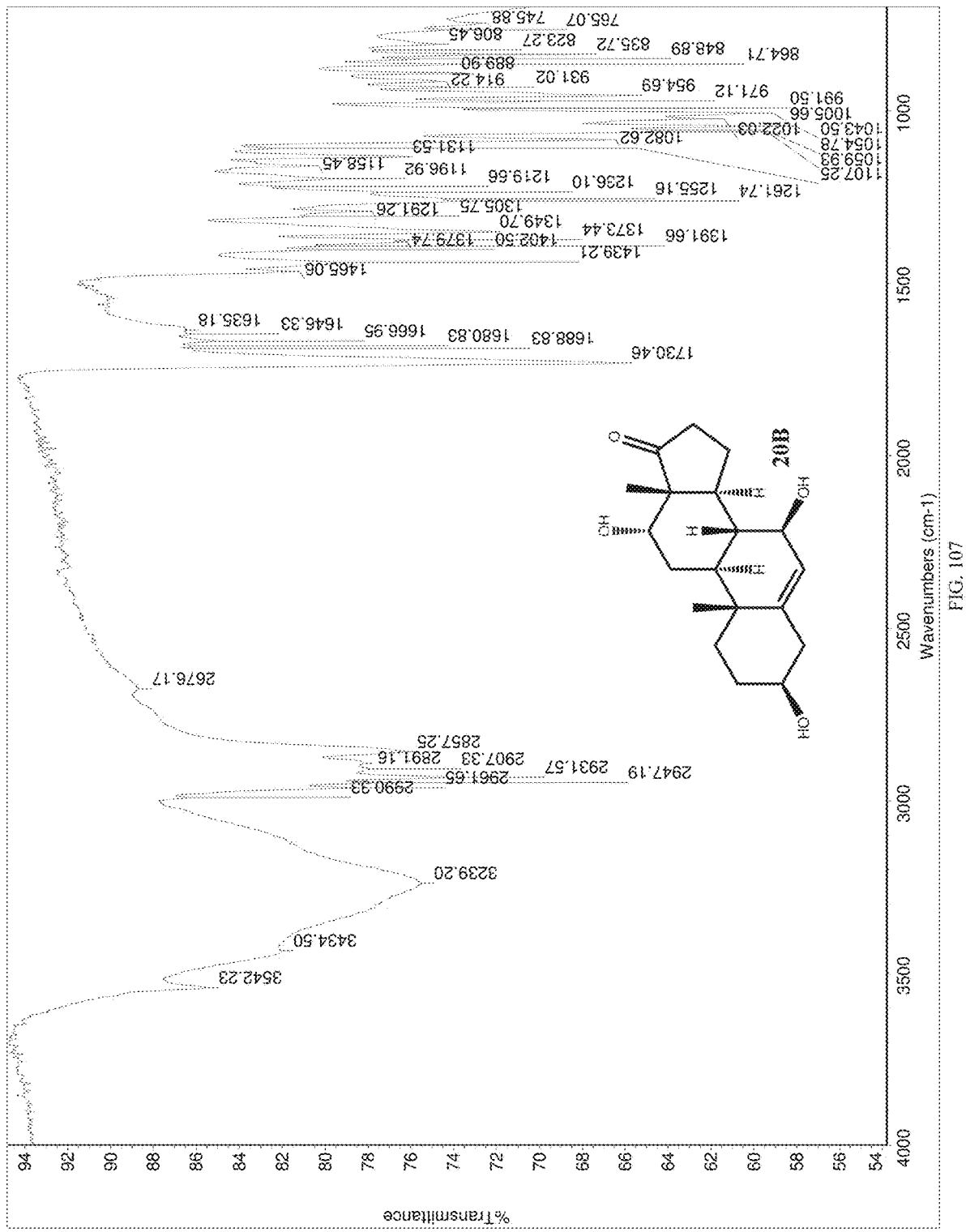

$^1$H and $^{13}$C NMR, HRMS, and IR spectra of Compound 44, as shown in FIGS. 97-99.

$^1$H NMR, HRMS, and IR spectra of Compound 45, as shown in FIGS. 100-103.

$^1$H NMR, HRMS, and IR spectra of Compound 20B, as shown in FIGS. 104-107.

As to the manner of usage and operation of the present invention, the same should be apparent from the above description. Accordingly, no further discussion relating to the manner of usage and operation will be provided.

While a preferred embodiment of the system has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent to one skilled in the art, and all equivalent relationships to those illustrated in the drawings and described in the specification are intended to be encompassed by the present invention.

Throughout this specification, unless the context requires otherwise, the word "comprise" or variations such as "comprises" or "comprising" or the term "includes" or variations, thereof, or the term "having" or variations thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modifications that fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A compound having a general formula (I) or a pharmaceutically acceptable salt thereof:

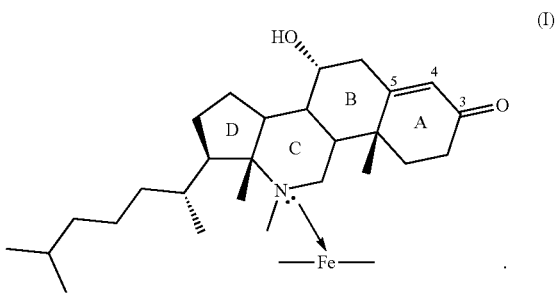

(heme of P450 8B1)
14

2. A compound having a general formula (II) or a pharmaceutically acceptable salt thereof:

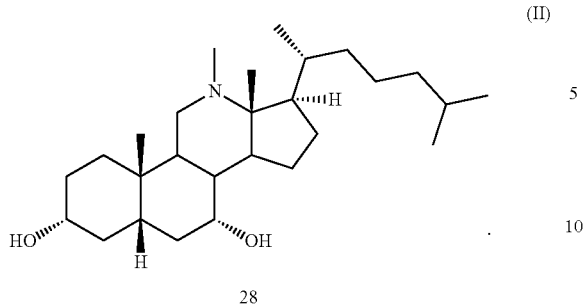

3. The general formula of claim 1, wherein the general formula is reductively animated to produce at least one derivative.

4. The at least one derivative of claim 3, wherein the derivative is a 12-dimethylamino derivative.

5. The at least one derivative of claim 3, wherein the derivative is a substrate of P450 8B1.

6. A pharmaceutical composition comprising the compound of claim 1.

7. The general formula of claim 2, wherein the general formula is reductively animated to produce at least one derivative.

8. The at least one derivative of claim 7, wherein the derivative is a 12-dimethylamino derivative.

9. The at least one derivative of claim 7, wherein the derivative is a substrate of P450 8B1.

10. A pharmaceutical composition comprising the compound of claim 2.

* * * * *